(12) United States Patent
Sternlicht et al.

(10) Patent No.: US 8,802,839 B2
(45) Date of Patent: Aug. 12, 2014

(54) CONNECTIVE TISSUE GROWTH FACTOR ANTISENSE OLIGONUCLEOTIDES

(75) Inventors: Mark D. Sternlicht, San Francisco, CA (US); Todd W. Seeley, Oakland, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 13/546,799

(22) Filed: Jul. 11, 2012

(65) Prior Publication Data

US 2013/0178510 A1    Jul. 11, 2013

Related U.S. Application Data

(60) Provisional application No. 61/508,264, filed on Jul. 15, 2011.

(51) Int. Cl.
*C07H 21/04* (2006.01)
*C12N 15/113* (2010.01)

(52) U.S. Cl.
USPC ........................................ 536/24.5; 514/44 A

(58) Field of Classification Search
None
See application file for complete search history.

(56) References Cited

U.S. PATENT DOCUMENTS

| | | | |
|---|---|---|---|
| 6,358,741 B1 | 3/2002 | Schmidt et al. | |
| 6,965,025 B2 | 11/2005 | Gaarde et al. | |
| 7,462,602 B2 | 12/2008 | Schultz et al. | |
| 7,622,454 B2 * | 11/2009 | Shepard et al. | 514/44 R |
| 7,709,630 B2 | 5/2010 | Gaarde et al. | |
| 8,252,762 B2 | 8/2012 | Dean et al. | |
| 2008/0108583 A1 * | 5/2008 | Feinstein | 514/44 |
| 2013/0045479 A1 | 2/2013 | Inazawa et al. | |

FOREIGN PATENT DOCUMENTS

| | | |
|---|---|---|
| WO | WO 2003/053340 A2 | 7/2003 |
| WO | WO 2010/027830 A2 | 3/2010 |
| WO | WO 2010/027831 A1 | 3/2010 |
| WO | WO 2010/027832 A1 | 3/2010 |
| WO | WO 2010/042281 A2 | 4/2010 |
| WO | WO 2011119887 A1 * | 9/2011 |

OTHER PUBLICATIONS

Pages 1-84, 526-536 and 1179-1186 of WO 2008/050329, May 2008 (104 pages total).*

Chiou, M-J., et al., "The Physiological Role of CTGF/CCN2 in Zebrafish Notochound Development and Biological Analysis of the Proximal Promoter Region," Biochem. & Biophys. Res. Comm. (2006) 349:750-758.

Daniels, J.T., et al., "Mediation of Transforming Growth Factor-β1-Stimulated Matrix Contraction by Fibroblasts: A Role for Connective Tissue Growth Factor in Contractile Scarring," Amer. J. of Path. (2003) 163: 2043-2052.

Dun, et al., Accession No. AZ781130 on database rst. seq. Feb. 16, 2001.

Guha, M. et al., "Specific Down-Regulation of Connective Tissue Growth Factor Attenuates Progression of Nephropathy in Mouse Models of Type 1 and Type 2 Diabetes," FASEB J. (2007) 21:3355-3368.

Hillier, et al., Accession No. R06912 on Database rst. seq. Apr. 5, 1995.

Hishikawa, K., et al., "Connective Tissue Growth Facotor Induces Apoptosis in Human Breast Cancer Cell Line MCF-7," J. Biological Chem. (1999) 274:37461-37466.

Hishikawa, K., et al., "Transforming Growth Factor-β1 Induces Apoptosis Via Connective Tissue Growth Factor in Human Aortic Smooth Muscle Cells," Eur. J. Pharm. (1999) 385:287-290.

Shimo, T., et al., Inhibition of Endogenous Expression of Connective Tissue Growth Factor by Its Antisense Oligonucleotide and Antisense RNA Suppresses Proliferation and Migration of Vascular Endothelial Cells, J. Biochem (1998) 124: 130-140.

Sisco, M., et al., "Antisense Inhibition of Connective Tissue Growth Factor (CTGF/CCN2) mRNA Limits Hypertrophic Scarring Without Affecting Wound Healing In Vivo," Wound Rep Reg. (2008) 16:661-673.

Uchio, K., et al., "Down-regulation of Connective Tissue Growth Factor and Type 1 Collagen mRNA Expression by Connective Tissue Growth Factor Antisense Oligonucleotide During Experimental Liver Fibrosis" Wound Rep Reg (2004) 12: 60-66.

Yamanaka, O., et al., "Connective Tissue Growth Factor Modulates Extracellular Matrix Production in Human Subconjunctival Fibroblasts and Their Proliferation and Migration in Vitro," Jpn. J. Oph. (2008) 52:8-15.

Yokoi, H., et al., "Reduction in Connective Tissue Growth Factor by Antisense Treatment Ameliorates Renal Tubuloimerstitial Fibrosis," J. Am. Soc. Nephrol. (2004) 15:1430-1440.

* cited by examiner

*Primary Examiner* — Tracy Vivlemore

(74) *Attorney, Agent, or Firm* — Leanne C. Price, Esq.; Paul Borchardt

(57) ABSTRACT

The present invention relates to antisense oligonucleotides that target human CTGF mRNA and inhibit CTGF mRNA expression. Additionally, regions of human CTGF mRNA that are exceptionally sensitive to antisense inhibition are disclosed. Pharmaceutical compositions comprising the antisense oligonucleotides are further disclosed. These compositions are useful for treating disorders and conditions that are associated with or influenced by CTGF expression.

14 Claims, 10 Drawing Sheets

```
   1 aaactcacac aacaactctt ccccgctgag aggagacagc cagtgcgact ccaccctcca
  61 gctcgacggc agccgcccg gccgacagcc ccgagacgac agcccggcgc gtcccggtcc
 121 ccacctccga ccaccgccag cgctccaggc cccgccgctc ccgctcgcc gccaccgcgc
 181 cctccgctcc gcccgcagtg ccaaccatga ccgccgccag tatgggcccc gtccgcgtcg
 241 ccttcgtggt cctcctcgcc ctctgcagcc ggccggccgt cggccagaac tgcagcgggc
 301 cgtgccggtg cccggacgag ccggcgccgc gctgcccggc gggcgtgagc ctcgtgctgg
 361 acggctgcgg ctgctgccgc gtctgcgcca agcagctggg cgagctgtgc accgagcgcg
 421 accctgcga cccgcacaag ggcctcttct gtgacttcgg ctcccggcc aaccgcaaga
 481 tcggcgtgtg caccgccaaa gatggtgctc cctgcatctt cggtggtacg gtgtaccgca
 541 gcggagagtc cttccagagc agctgcaagt accagtgcac gtgcctggac ggggcggtgg
 601 gctgcatgcc cctgtgcagc atggacgttc gtctgccag ccctgactgc cccttccga
 661 ggagggtcaa gctgccgg aaatgctgcg aggagtgggt gtgtgacgag cccaaggacc
 721 aaaccgtggt tgggcctgcc ctcgcggctt accgactgga agacacgttt ggcccagacc
 781 caactatgat tagagccaac tgcctggtcc agaccacaga gtggagcgcc tgttccaaga
 841 cctgtgggat gggcatctcc acccgggtta ccaatgacaa cgcctcctgc aggctagaga
 901 agcagagccg cctgtgcatg gtcaggcctt gcgaagctga cctggaagag aacattaaga
 961 agggcaaaaa gtgcatccgt actcccaaaa tctccaagcc tatcaagttt gagctttctg
1021 gctgcaccag catgaagaca taccgagcta aattctgtgg agtatgtacc gacggccgat
1081 gctgcacccc ccacagaacc accaccctgc cggtggagtt caagtgccct gacggcgagg
1141 tcatgaagaa gaacatgatg ttcatcaaga cctgtgcctg ccattacaac tgtccggag
1201 acaatgacat ctttgaatcg ctgtactaca ggaagatgta cggagacatg gcatgaagcc
1261 agagagtgaa agacattaac tcattagact ggaacttgaa ctgattcaca tctcattttt
1321 ccgtaaaaat gatttcagta gcacaagtta tttaaatctg ttttctaac tgggggaaaa
1381 gattcccacc caattcaaaa cattgtgcca tgtcaaacaa atagtctatc aacccagac
1441 actggtttga agaatgttaa gacttgacag tggaactaca ttagtacaca gcaccagaat
1501 gtatattaag gtgtggcttt aggagcagtg ggagggtacc agcagaaagg ttagtatcat
1561 cagatagcat cttatacgag taatatgcct gctatttgaa gtgtaattga gaaggaaaat
1621 tttagcgtgc tcactgacct gcctgtagcc ccagtgacag ctaggatgtg cattctccag
1681 ccatcaagag actgagtcaa gttgttcctt aagtcagaac agcagactca gctctgacat
1741 tctgattcga atgacactgt tcaggaatcg gaatcctgtc gattagactg gacagcttgt
1801 ggcaagtgaa tttgcctgta acaagccaga ttttttaaaa tttatattgt aaatattgtg
1861 tgtgtgtgtg tgtgtgtata tatatatata tgtacagtta tctaagttaa tttaaagttg
1921 tttgtgcctt tttatttttg tttttaatgc tttgatattt caatgttagc ctcaatttct
1981 gaacaccata ggtagaatgt aaagcttgtc tgatcgttca aagcatgaaa tggatactta
2041 tatgaaatt ctgctcagat agaatgacag tccgtcaaaa cagattgttt gcaaagggga
2101 ggcatcagtg tccttggcag gctgatttct aggtaggaaa tgtggtagcc tcactttaa
2161 tgaacaaatg gcctttatta aaaactgagt gactctatat agctgatcag ttttttcacc
2221 tggaagcatt tgtttctact ttgatatgac tgttttcgg acagtttatt tgttgagagt
2281 gtgaccaaaa gttacatgtt tgcacctttc tagttgaaaa taaagtgtat attttttcta
2341 taaaaaaaa aaaaaaaa
```

FIG. 1

SEQUENCE LISTING

<160> NUMBER OF SEQ ID NOS: 340

<210> SEQ ID NO 1
<211> LENGTH: 2358
<212> TYPE: DNA
<213> ORGANISM: Homo sapiens

<400> SEQUENCE: 1

```
aaactcacac aacaactctt ccccgctgag aggagacagc cagtgcgact ccaccctcca      60
gctcgacggc agccgccccg gccgacagcc ccgagacgac agcccggcgc gtcccggtcc     120
ccacctccga ccaccgccag cgctccaggc cccgccgctc ccgctcgcc gccaccgcgc      180 cctccgctcc gcccgcagtg ccaaccatga ccgccgccag tatgggcccc gtccgcgtcg     240
ccttcgtggt cctcctcgcc ctctgcagcc ggccggccgt cggccagaac tgcagcgggc     300
cgtgccggtg cccggacgag ccggcgccgc gctgcccggc gggcgtgagc ctcgtgctgg     360
acggctgcgg ctgctgccgc gtctgcgcca agcagctggg cgagctgtgc accgagcgcg     420
accctgcgca cccgcacaag ggcctcttct gtgacttcgg ctccccggcc aaccgcaaga     480
tcggcgtgtg caccgccaaa gatggtgctc cctgcatctt cggtggtacg gtgtaccgca     540
```

```
gcggagagtc cttccagagc agctgcaagt accagtgcac gtgcctggac ggggcggtgg      600
gctgcatgcc cctgtgcagc atggacgttc gtctgcccag ccctgactgc cccttcccga      660
ggagggtcaa gctgcccggg aaatgctgcg aggagtgggt gtgtgacgag cccaaggacc      720
aaaccgtggt tgggcctgcc ctcgcggctt accgactgga agacacgttt ggcccagacc      780
caactatgat tagagccaac tgcctggtcc agaccacaga gtggagcgcc tgttccaaga      840
cctgtgggat gggcatctcc acccgggtta ccaatgacaa cgcctcctgc aggctagaga      900
agcagagccg cctgtgcatg gtcaggcctt gcgaagctga cctggaagag aacattaaga      960
agggcaaaaa gtgcatccgt actcccaaaa tctccaagcc tatcaagttt gagctttctg     1020
gctgcaccag catgaagaca taccgagcta aattctgtgg agtatgtacc gacggccgat     1080
gctgcacccc ccacagaacc accaccctgc cggtggagtt caagtgccct gacggcgagg     1140
tcatgaagaa gaacatgatg ttcatcaaga cctgtgcctg ccattacaac tgtcccggag     1200
acaatgacat ctttgaatcg ctgtactaca ggaagatgta cggagacatg gcatgaagcc     1260
agagagtgag agacattaac tcattagact ggaacttgaa ctgattcaca tctcattttt     1320
ccgtaaaaat gatttcagta gcacaagtta tttaaatctg ttttttctaac tgggggaaaa     1380 gattcccacc caattcaaaa cattgtgcca tgtcaaacaa atagtctatc aaccccagac     1440
actggtttga agaatgttaa gacttgacag tggaactaca ttagtacaca gcaccagaat     1500
gtatattaag gtgtggcttt aggagcagtg ggagggtacc agcagaaagg ttagtatcat     1560
cagatagcat cttatacgag taatatgcct gctatttgaa gtgtaattga aaggaaaat     1620 tttagcgtgc tcactgacct gcctgtagcc ccagtgacag ctaggatgtg cattctccag     1680
ccatcaagag actgagtcaa gttgttcctt aagtcagaac agcagactca gctctgacat     1740
tctgattcga atgacactgt tcaggaatcg gaatcctgtc gattagactg gacagcttgt     1800
ggcaagtgaa tttgcctgta acaagccaga tttttaaaa tttatattgt aaatattgtg     1860
tgtgtgtgtg tgtgtgtata tatatatata tgtacagtta tctaagttaa tttaaagttg     1920
tttgtgcctt tttattttg tttttaatgc tttgatattt caatgttagc ctcaatttct     1980
gaacaccata ggtagaatgt aaagcttgtc tgatcgttca aagcatgaaa tggatactta     2040
tatgaaaatt ctgctcagat agaatgacag tccgtcaaaa cagattgttt gcaaagggga     2100
ggcatcagtg tccttggcag gctgatttct aggtaggaaa tgtggtagcc tcacttttaa     2160
tgaacaaatg gcctttatta aaaactgagt gactctatat agctgatcag tttttttcacc     2220 tggaagcatt tgtttctact ttgatatgac tgttttttcgg acagttatt tgttgagagt     2280 gtgaccaaaa gttacatgtt tgcacctttc tagttgaaaa taaagtgtat attttttcta     2340
taaaaaaaaa aaaaaaaa                                                   2358
```

<210> SEQ ID NO 2
<211> LENGTH: 20
<212> TYPE: DNA
<213> ORGANISM: Homo sapiens

<400> SEQUENCE: 2

```
ggggaagagt tgttgtgtga                                                    20
```

<210> SEQ ID NO 3
<211> LENGTH: 20
<212> TYPE: DNA
<213> ORGANISM: Homo sapiens

<400> SEQUENCE: 3

-continued gtcgcactgg ctgtctcctc                                      20

<210> SEQ ID NO 4
<211> LENGTH: 20
<212> TYPE: DNA
<213> ORGANISM: Homo sapiens

<400> SEQUENCE: 4
agctggaggg tggagtcgca                                      20

<210> SEQ ID NO 5
<211> LENGTH: 20
<212> TYPE: DNA
<213> ORGANISM: Homo sapiens

<400> SEQUENCE: 5
ggctgccgtc gagctggagg                                      20

<210> SEQ ID NO 6
<211> LENGTH: 20
<212> TYPE: DNA
<213> ORGANISM: Homo sapiens

<400> SEQUENCE: 6
tcggggctgt cggccggggc                                      20

<210> SEQ ID NO 7
<211> LENGTH: 20
<212> TYPE: DNA
<213> ORGANISM: Homo sapiens

<400> SEQUENCE: 7
ggctgtcgtc tcggggctgt                                      20

<210> SEQ ID NO 8
<211> LENGTH: 20
<212> TYPE: DNA
<213> ORGANISM: Homo sapiens

<400> SEQUENCE: 8
ggcggcggtc atggttggca                                      20

<210> SEQ ID NO 9
<211> LENGTH: 20
<212> TYPE: DNA
<213> ORGANISM: Homo sapiens

<400> SEQUENCE: 9
gggcccatac tggcggcggt                                      20

<210> SEQ ID NO 10
<211> LENGTH: 20
<212> TYPE: DNA
<213> ORGANISM: Homo sapiens

<400> SEQUENCE: 10
gcggacgggg cccatactgg                                      20

<210> SEQ ID NO 11
<211> LENGTH: 20
<212> TYPE: DNA
<213> ORGANISM: Homo sapiens

<400> SEQUENCE: 11
gcgacgcgga cggggcccat                                              20

<210> SEQ ID NO 12
<211> LENGTH: 20
<212> TYPE: DNA
<213> ORGANISM: Homo sapiens

<400> SEQUENCE: 12
cgaggaggac cacgaaggcg                                              20

<210> SEQ ID NO 13
<211> LENGTH: 20
<212> TYPE: DNA
<213> ORGANISM: Homo sapiens

<400> SEQUENCE: 13
cagagggcga ggaggaccac                                              20

<210> SEQ ID NO 14
<211> LENGTH: 20
<212> TYPE: DNA
<213> ORGANISM: Homo sapiens

<400> SEQUENCE: 14
ccggctgcag agggcgagga                                              20

<210> SEQ ID NO 15
<211> LENGTH: 20
<212> TYPE: DNA
<213> ORGANISM: Homo sapiens

<400> SEQUENCE: 15
ccgacggccg gccggctgca                                              20

<210> SEQ ID NO 16
<211> LENGTH: 20
<212> TYPE: DNA
<213> ORGANISM: Homo sapiens

<400> SEQUENCE: 16
cccgctgcag ttctggccga                                              20

<210> SEQ ID NO 17
<211> LENGTH: 20
<212> TYPE: DNA
<213> ORGANISM: Homo sapiens

<400> SEQUENCE: 17
acggcccgct gcagttctgg                                              20

<210> SEQ ID NO 18
<211> LENGTH: 20
<212> TYPE: DNA
<213> ORGANISM: Homo sapiens

<400> SEQUENCE: 18
agcgcggcgc cggctcgtcc                                              20

<210> SEQ ID NO 19
<211> LENGTH: 20
<212> TYPE: DNA
<213> ORGANISM: Homo sapiens

```
<400> SEQUENCE: 19
gcacgaggct cacgcccgcc                                              20

<210> SEQ ID NO 20
<211> LENGTH: 20
<212> TYPE: DNA
<213> ORGANISM: Homo sapiens

<400> SEQUENCE: 20
cgcagccgtc cagcacgagg                                              20

<210> SEQ ID NO 21
<211> LENGTH: 20
<212> TYPE: DNA
<213> ORGANISM: Homo sapiens

<400> SEQUENCE: 21
cagccgcagc cgtccagcac                                              20

<210> SEQ ID NO 22
<211> LENGTH: 20
<212> TYPE: DNA
<213> ORGANISM: Homo sapiens

<400> SEQUENCE: 22
cagcagccgc agccgtccag                                              20

<210> SEQ ID NO 23
<211> LENGTH: 20
<212> TYPE: DNA
<213> ORGANISM: Homo sapiens

<400> SEQUENCE: 23
gcagcagccg cagccgtcca                                              20

<210> SEQ ID NO 24
<211> LENGTH: 20
<212> TYPE: DNA
<213> ORGANISM: Homo sapiens

<400> SEQUENCE: 24
ggcgcagacg cggcagcagc                                              20

<210> SEQ ID NO 25
<211> LENGTH: 20
<212> TYPE: DNA
<213> ORGANISM: Homo sapiens

<400> SEQUENCE: 25
cccagctgct tggcgcagac                                              20

<210> SEQ ID NO 26
<211> LENGTH: 20
<212> TYPE: DNA
<213> ORGANISM: Homo sapiens

<400> SEQUENCE: 26
agctcgccca gctgcttggc                                              20

<210> SEQ ID NO 27
<211> LENGTH: 20
<212> TYPE: DNA
```

```
<213> ORGANISM: Homo sapiens

<400> SEQUENCE: 27
ctcggtgcac agctcgccca                                               20

<210> SEQ ID NO 28
<211> LENGTH: 20
<212> TYPE: DNA
<213> ORGANISM: Homo sapiens

<400> SEQUENCE: 28
gcatgggtcg cgctcggtgc                                               20

<210> SEQ ID NO 29
<211> LENGTH: 20
<212> TYPE: DNA
<213> ORGANISM: Homo sapiens

<400> SEQUENCE: 29
cgggtcgcat gggtcgcgct                                               20

<210> SEQ ID NO 30
<211> LENGTH: 20
<212> TYPE: DNA
<213> ORGANISM: Homo sapiens

<400> SEQUENCE: 30
gaagaggccc ttgtgcgggt                                               20

<210> SEQ ID NO 31
<211> LENGTH: 20
<212> TYPE: DNA
<213> ORGANISM: Homo sapiens

<400> SEQUENCE: 31
gtcacagaag aggcccttgt                                               20

<210> SEQ ID NO 32
<211> LENGTH: 20
<212> TYPE: DNA
<213> ORGANISM: Homo sapiens

<400> SEQUENCE: 32
ggggagccga agtcacagaa                                               20

<210> SEQ ID NO 33
<211> LENGTH: 20
<212> TYPE: DNA
<213> ORGANISM: Homo sapiens

<400> SEQUENCE: 33
cttgcggttg gccggggagc                                               20

<210> SEQ ID NO 34
<211> LENGTH: 20
<212> TYPE: DNA
<213> ORGANISM: Homo sapiens

<400> SEQUENCE: 34
cgccgatctt gcggttggcc                                               20

<210> SEQ ID NO 35
<211> LENGTH: 20
```

```
<212> TYPE: DNA
<213> ORGANISM: Homo sapiens

<400> SEQUENCE: 35
ggtgcacacg ccgatcttgc                                              20

<210> SEQ ID NO 36
<211> LENGTH: 20
<212> TYPE: DNA
<213> ORGANISM: Homo sapiens

<400> SEQUENCE: 36
ccatctttgg cggtgcacac                                              20

<210> SEQ ID NO 37
<211> LENGTH: 20
<212> TYPE: DNA
<213> ORGANISM: Homo sapiens

<400> SEQUENCE: 37
gcagggagca ccatctttgg                                              20

<210> SEQ ID NO 38
<211> LENGTH: 20
<212> TYPE: DNA
<213> ORGANISM: Homo sapiens

<400> SEQUENCE: 38
ccaccgaaga tgcagggagc                                              20

<210> SEQ ID NO 39
<211> LENGTH: 20
<212> TYPE: DNA
<213> ORGANISM: Homo sapiens

<400> SEQUENCE: 39
caccgtacca ccgaagatgc                                              20

<210> SEQ ID NO 40
<211> LENGTH: 20
<212> TYPE: DNA
<213> ORGANISM: Homo sapiens

<400> SEQUENCE: 40
tctccgctgc ggtacaccgt                                              20

<210> SEQ ID NO 41
<211> LENGTH: 20
<212> TYPE: DNA
<213> ORGANISM: Homo sapiens

<400> SEQUENCE: 41
tggaaggact ctccgctgcg                                              20

<210> SEQ ID NO 42
<211> LENGTH: 20
<212> TYPE: DNA
<213> ORGANISM: Homo sapiens

<400> SEQUENCE: 42
ggtacttgca gctgctctgg                                              20

<210> SEQ ID NO 43
```

```
<211> LENGTH: 20
<212> TYPE: DNA
<213> ORGANISM: Homo sapiens

<400> SEQUENCE: 43
aggcacgtgc actggtactt                                              20

<210> SEQ ID NO 44
<211> LENGTH: 20
<212> TYPE: DNA
<213> ORGANISM: Homo sapiens

<400> SEQUENCE: 44
caccgccccg tccaggcacg                                              20

<210> SEQ ID NO 45
<211> LENGTH: 20
<212> TYPE: DNA
<213> ORGANISM: Homo sapiens

<400> SEQUENCE: 45
agcccaccgc cccgtccagg                                              20

<210> SEQ ID NO 46
<211> LENGTH: 20
<212> TYPE: DNA
<213> ORGANISM: Homo sapiens

<400> SEQUENCE: 46
catgcagccc accgccccgt                                              20

<210> SEQ ID NO 47
<211> LENGTH: 20
<212> TYPE: DNA
<213> ORGANISM: Homo sapiens

<400> SEQUENCE: 47
ctgcacaggg gcatgcagcc                                              20

<210> SEQ ID NO 48
<211> LENGTH: 20
<212> TYPE: DNA
<213> ORGANISM: Homo sapiens

<400> SEQUENCE: 48
cgtccatgct gcacaggggc                                              20

<210> SEQ ID NO 49
<211> LENGTH: 20
<212> TYPE: DNA
<213> ORGANISM: Homo sapiens

<400> SEQUENCE: 49
acgaacgtcc atgctgcaca                                              20

<210> SEQ ID NO 50
<211> LENGTH: 20
<212> TYPE: DNA
<213> ORGANISM: Homo sapiens

<400> SEQUENCE: 50
agtcagggct gggcagacga                                              20
```

```
<210> SEQ ID NO 51
<211> LENGTH: 20
<212> TYPE: DNA
<213> ORGANISM: Homo sapiens

<400> SEQUENCE: 51
gggaaggggc agtcagggct                                              20

<210> SEQ ID NO 52
<211> LENGTH: 20
<212> TYPE: DNA
<213> ORGANISM: Homo sapiens

<400> SEQUENCE: 52
cctcctcggg aagggcagt                                               20

<210> SEQ ID NO 53
<211> LENGTH: 20
<212> TYPE: DNA
<213> ORGANISM: Homo sapiens

<400> SEQUENCE: 53
ggcagcttga ccctcctcgg                                              20

<210> SEQ ID NO 54
<211> LENGTH: 20
<212> TYPE: DNA
<213> ORGANISM: Homo sapiens

<400> SEQUENCE: 54
cccgggcagc ttgaccctcc                                              20

<210> SEQ ID NO 55
<211> LENGTH: 20
<212> TYPE: DNA
<213> ORGANISM: Homo sapiens

<400> SEQUENCE: 55
actcctcgca gcatttcccg                                              20

<210> SEQ ID NO 56
<211> LENGTH: 20
<212> TYPE: DNA
<213> ORGANISM: Homo sapiens

<400> SEQUENCE: 56
cacacccact cctcgcagca                                              20

<210> SEQ ID NO 57
<211> LENGTH: 20
<212> TYPE: DNA
<213> ORGANISM: Homo sapiens

<400> SEQUENCE: 57
gtcacacacc cactcctcgc                                              20

<210> SEQ ID NO 58
<211> LENGTH: 20
<212> TYPE: DNA
<213> ORGANISM: Homo sapiens

<400> SEQUENCE: 58
gctcgtcaca cacccactcc                                              20
```

<210> SEQ ID NO 59
<211> LENGTH: 20
<212> TYPE: DNA
<213> ORGANISM: Homo sapiens

<400> SEQUENCE: 59
ccacggtttg gtccttgggc                                              20

<210> SEQ ID NO 60
<211> LENGTH: 20
<212> TYPE: DNA
<213> ORGANISM: Homo sapiens

<400> SEQUENCE: 60
ggcaggccca accacggttt                                              20

<210> SEQ ID NO 61
<211> LENGTH: 20
<212> TYPE: DNA
<213> ORGANISM: Homo sapiens

<400> SEQUENCE: 61
gtcggtaagc cgcgagggca                                              20

<210> SEQ ID NO 62
<211> LENGTH: 20
<212> TYPE: DNA
<213> ORGANISM: Homo sapiens

<400> SEQUENCE: 62
gtgtcttcca gtcggtaagc                                              20

<210> SEQ ID NO 63
<211> LENGTH: 20
<212> TYPE: DNA
<213> ORGANISM: Homo sapiens

<400> SEQUENCE: 63
gccaaacgtg tcttccagtc                                              20

<210> SEQ ID NO 64
<211> LENGTH: 20
<212> TYPE: DNA
<213> ORGANISM: Homo sapiens

<400> SEQUENCE: 64
gggtctgggc caaacgtgtc                                              20

<210> SEQ ID NO 65
<211> LENGTH: 20
<212> TYPE: DNA
<213> ORGANISM: Homo sapiens

<400> SEQUENCE: 65
aatcatagtt gggtctgggc                                              20

<210> SEQ ID NO 66
<211> LENGTH: 20
<212> TYPE: DNA
<213> ORGANISM: Homo sapiens

<400> SEQUENCE: 66
ggaccaggca gttggctcta                                              20

```
<210> SEQ ID NO 67
<211> LENGTH: 20
<212> TYPE: DNA
<213> ORGANISM: Homo sapiens

<400> SEQUENCE: 67
cgctccactc tgtggtctgg                                              20

<210> SEQ ID NO 68
<211> LENGTH: 20
<212> TYPE: DNA
<213> ORGANISM: Homo sapiens

<400> SEQUENCE: 68
ggaacaggcg ctccactctg                                              20

<210> SEQ ID NO 69
<211> LENGTH: 20
<212> TYPE: DNA
<213> ORGANISM: Homo sapiens

<400> SEQUENCE: 69
tgcccatccc acaggtcttg                                              20

<210> SEQ ID NO 70
<211> LENGTH: 20
<212> TYPE: DNA
<213> ORGANISM: Homo sapiens

<400> SEQUENCE: 70
ggagatgccc atcccacagg                                              20

<210> SEQ ID NO 71
<211> LENGTH: 20
<212> TYPE: DNA
<213> ORGANISM: Homo sapiens

<400> SEQUENCE: 71
gtcattggta acccgggtgg                                              20

<210> SEQ ID NO 72
<211> LENGTH: 20
<212> TYPE: DNA
<213> ORGANISM: Homo sapiens

<400> SEQUENCE: 72
ggcgttgtca ttggtaaccc                                              20

<210> SEQ ID NO 73
<211> LENGTH: 20
<212> TYPE: DNA
<213> ORGANISM: Homo sapiens

<400> SEQUENCE: 73
caggaggcgt tgtcattggt                                              20

<210> SEQ ID NO 74
<211> LENGTH: 20
<212> TYPE: DNA
<213> ORGANISM: Homo sapiens

<400> SEQUENCE: 74
```

-continued gctctgcttc tctagcctgc                                                    20

<210> SEQ ID NO 75
<211> LENGTH: 20
<212> TYPE: DNA
<213> ORGANISM: Homo sapiens

<400> SEQUENCE: 75
ggcggctctg cttctctagc                                                    20

<210> SEQ ID NO 76
<211> LENGTH: 20
<212> TYPE: DNA
<213> ORGANISM: Homo sapiens

<400> SEQUENCE: 76
gaccatgcac aggcggctct                                                    20

<210> SEQ ID NO 77
<211> LENGTH: 20
<212> TYPE: DNA
<213> ORGANISM: Homo sapiens

<400> SEQUENCE: 77
caaggcctga ccatgcacag                                                    20

<210> SEQ ID NO 78
<211> LENGTH: 20
<212> TYPE: DNA
<213> ORGANISM: Homo sapiens

<400> SEQUENCE: 78
ctcttccagg tcagcttcgc                                                    20

<210> SEQ ID NO 79
<211> LENGTH: 20
<212> TYPE: DNA
<213> ORGANISM: Homo sapiens

<400> SEQUENCE: 79
tgttctcttc caggtcagct                                                    20

<210> SEQ ID NO 80
<211> LENGTH: 20
<212> TYPE: DNA
<213> ORGANISM: Homo sapiens

<400> SEQUENCE: 80
gcccttctta atgttctctt                                                    20

<210> SEQ ID NO 81
<211> LENGTH: 20
<212> TYPE: DNA
<213> ORGANISM: Homo sapiens

<400> SEQUENCE: 81
cggatgcact ttttgccctt                                                    20

<210> SEQ ID NO 82
<211> LENGTH: 20
<212> TYPE: DNA
<213> ORGANISM: Homo sapiens

<400> SEQUENCE: 82

```
gggagtacgg atgcactttt                                              20

<210> SEQ ID NO 83
<211> LENGTH: 20
<212> TYPE: DNA
<213> ORGANISM: Homo sapiens

<400> SEQUENCE: 83
ggcttggaga ttttgggagt                                              20

<210> SEQ ID NO 84
<211> LENGTH: 20
<212> TYPE: DNA
<213> ORGANISM: Homo sapiens

<400> SEQUENCE: 84
acttgatagg cttggagatt                                              20

<210> SEQ ID NO 85
<211> LENGTH: 20
<212> TYPE: DNA
<213> ORGANISM: Homo sapiens

<400> SEQUENCE: 85
gctcaaactt gataggcttg                                              20

<210> SEQ ID NO 86
<211> LENGTH: 20
<212> TYPE: DNA
<213> ORGANISM: Homo sapiens

<400> SEQUENCE: 86
gccagaaagc tcaaacttga                                              20

<210> SEQ ID NO 87
<211> LENGTH: 20
<212> TYPE: DNA
<213> ORGANISM: Homo sapiens

<400> SEQUENCE: 87
gcagccagaa agctcaaact                                              20

<210> SEQ ID NO 88
<211> LENGTH: 20
<212> TYPE: DNA
<213> ORGANISM: Homo sapiens

<400> SEQUENCE: 88
tcttcatgct ggtgcagcca                                              20

<210> SEQ ID NO 89
<211> LENGTH: 20
<212> TYPE: DNA
<213> ORGANISM: Homo sapiens

<400> SEQUENCE: 89
gctcggtatg tcttcatgct                                              20

<210> SEQ ID NO 90
<211> LENGTH: 20
<212> TYPE: DNA
<213> ORGANISM: Homo sapiens
```

```
<400> SEQUENCE: 90
gaatttagct cggtatgtct                                              20

<210> SEQ ID NO 91
<211> LENGTH: 20
<212> TYPE: DNA
<213> ORGANISM: Homo sapiens

<400> SEQUENCE: 91
ctccacagaa tttagctcgg                                              20

<210> SEQ ID NO 92
<211> LENGTH: 20
<212> TYPE: DNA
<213> ORGANISM: Homo sapiens

<400> SEQUENCE: 92
gccgtcggta catactccac                                              20

<210> SEQ ID NO 93
<211> LENGTH: 20
<212> TYPE: DNA
<213> ORGANISM: Homo sapiens

<400> SEQUENCE: 93
gtgcagcatc ggccgtcggt                                              20

<210> SEQ ID NO 94
<211> LENGTH: 20
<212> TYPE: DNA
<213> ORGANISM: Homo sapiens

<400> SEQUENCE: 94
ggggtgcagc atcggccgtc                                              20

<210> SEQ ID NO 95
<211> LENGTH: 20
<212> TYPE: DNA
<213> ORGANISM: Homo sapiens

<400> SEQUENCE: 95 tgggggtgc agcatcggcc                                               20

<210> SEQ ID NO 96
<211> LENGTH: 20
<212> TYPE: DNA
<213> ORGANISM: Homo sapiens

<400> SEQUENCE: 96
ggttctgtgg ggggtgcagc                                              20

<210> SEQ ID NO 97
<211> LENGTH: 20
<212> TYPE: DNA
<213> ORGANISM: Homo sapiens

<400> SEQUENCE: 97
gggtggtggt tctgtggggg                                              20

<210> SEQ ID NO 98
<211> LENGTH: 20
<212> TYPE: DNA
<213> ORGANISM: Homo sapiens
```

<400> SEQUENCE: 98
cggcagggtg gtggttctgt                                               20

<210> SEQ ID NO 99
<211> LENGTH: 20
<212> TYPE: DNA
<213> ORGANISM: Homo sapiens

<400> SEQUENCE: 99
ggcacttgaa ctccaccggc                                               20

<210> SEQ ID NO 100
<211> LENGTH: 20
<212> TYPE: DNA
<213> ORGANISM: Homo sapiens

<400> SEQUENCE: 100
acctcgccgt cagggcactt                                               20

<210> SEQ ID NO 101
<211> LENGTH: 20
<212> TYPE: DNA
<213> ORGANISM: Homo sapiens

<400> SEQUENCE: 101
cttcttcatg acctcgccgt                                               20

<210> SEQ ID NO 102
<211> LENGTH: 20
<212> TYPE: DNA
<213> ORGANISM: Homo sapiens

<400> SEQUENCE: 102
acatcatgtt cttcttcatg                                               20

<210> SEQ ID NO 103
<211> LENGTH: 20
<212> TYPE: DNA
<213> ORGANISM: Homo sapiens

<400> SEQUENCE: 103
ggcacaggtc ttgatgaaca                                               20

<210> SEQ ID NO 104
<211> LENGTH: 20
<212> TYPE: DNA
<213> ORGANISM: Homo sapiens

<400> SEQUENCE: 104
gtaatggcag gcacaggtct                                               20

<210> SEQ ID NO 105
<211> LENGTH: 20
<212> TYPE: DNA
<213> ORGANISM: Homo sapiens

<400> SEQUENCE: 105
ccgggacagt tgtaatggca                                               20

<210> SEQ ID NO 106
<211> LENGTH: 20
<212> TYPE: DNA

```
<213> ORGANISM: Homo sapiens

<400> SEQUENCE: 106
agatgtcatt gtctccggga                                        20

<210> SEQ ID NO 107
<211> LENGTH: 20
<212> TYPE: DNA
<213> ORGANISM: Homo sapiens

<400> SEQUENCE: 107
acagcgattc aaagatgtca                                        20

<210> SEQ ID NO 108
<211> LENGTH: 20
<212> TYPE: DNA
<213> ORGANISM: Homo sapiens

<400> SEQUENCE: 108
tgtagtacag cgattcaaag                                        20

<210> SEQ ID NO 109
<211> LENGTH: 20
<212> TYPE: DNA
<213> ORGANISM: Homo sapiens

<400> SEQUENCE: 109
gtctccgtac atcttcctgt                                        20

<210> SEQ ID NO 110
<211> LENGTH: 20
<212> TYPE: DNA
<213> ORGANISM: Homo sapiens

<400> SEQUENCE: 110
gccatgtctc cgtacatctt                                        20

<210> SEQ ID NO 111
<211> LENGTH: 20
<212> TYPE: DNA
<213> ORGANISM: Homo sapiens

<400> SEQUENCE: 111
gcttcatgcc atgtctccgt                                        20

<210> SEQ ID NO 112
<211> LENGTH: 20
<212> TYPE: DNA
<213> ORGANISM: Homo sapiens

<400> SEQUENCE: 112
cactctctgg cttcatgcca                                        20

<210> SEQ ID NO 113
<211> LENGTH: 20
<212> TYPE: DNA
<213> ORGANISM: Homo sapiens

<400> SEQUENCE: 113
gtctctcact ctctggcttc                                        20

<210> SEQ ID NO 114
<211> LENGTH: 20
```

```
<212> TYPE: DNA
<213> ORGANISM: Homo sapiens

<400> SEQUENCE: 114
gttaatgtct ctcactctct                                           20

<210> SEQ ID NO 115
<211> LENGTH: 20
<212> TYPE: DNA
<213> ORGANISM: Homo sapiens

<400> SEQUENCE: 115
atcagttcaa gttccagtct                                           20

<210> SEQ ID NO 116
<211> LENGTH: 20
<212> TYPE: DNA
<213> ORGANISM: Homo sapiens

<400> SEQUENCE: 116
acggaaaaat gagatgtgaa                                           20

<210> SEQ ID NO 117
<211> LENGTH: 20
<212> TYPE: DNA
<213> ORGANISM: Homo sapiens

<400> SEQUENCE: 117
actgaaatca tttttacgga                                           20

<210> SEQ ID NO 118
<211> LENGTH: 20
<212> TYPE: DNA
<213> ORGANISM: Homo sapiens

<400> SEQUENCE: 118
acttgtgcta ctgaaatcat                                           20

<210> SEQ ID NO 119
<211> LENGTH: 20
<212> TYPE: DNA
<213> ORGANISM: Homo sapiens

<400> SEQUENCE: 119
cccccagtta gaaaaacaga                                           20

<210> SEQ ID NO 120
<211> LENGTH: 20
<212> TYPE: DNA
<213> ORGANISM: Homo sapiens

<400> SEQUENCE: 120
gaatcttttc ccccagttag                                           20

<210> SEQ ID NO 121
<211> LENGTH: 20
<212> TYPE: DNA
<213> ORGANISM: Homo sapiens

<400> SEQUENCE: 121
atgttttgaa ttgggtggga                                           20

<210> SEQ ID NO 122
```

```
<211> LENGTH: 20
<212> TYPE: DNA
<213> ORGANISM: Homo sapiens

<400> SEQUENCE: 122
ctatttgttt gacatggcac                                              20

<210> SEQ ID NO 123
<211> LENGTH: 20
<212> TYPE: DNA
<213> ORGANISM: Homo sapiens

<400> SEQUENCE: 123
ggggttgata gactatttgt                                              20

<210> SEQ ID NO 124
<211> LENGTH: 20
<212> TYPE: DNA
<213> ORGANISM: Homo sapiens

<400> SEQUENCE: 124
cagtgtctgg ggttgataga                                              20

<210> SEQ ID NO 125
<211> LENGTH: 20
<212> TYPE: DNA
<213> ORGANISM: Homo sapiens

<400> SEQUENCE: 125
cattcttcaa accagtgtct                                              20

<210> SEQ ID NO 126
<211> LENGTH: 20
<212> TYPE: DNA
<213> ORGANISM: Homo sapiens

<400> SEQUENCE: 126
tccactgtca agtcttaaca                                              20

<210> SEQ ID NO 127
<211> LENGTH: 20
<212> TYPE: DNA
<213> ORGANISM: Homo sapiens

<400> SEQUENCE: 127
gtagttccac tgtcaagtct                                              20

<210> SEQ ID NO 128
<211> LENGTH: 20
<212> TYPE: DNA
<213> ORGANISM: Homo sapiens

<400> SEQUENCE: 128
acattctggt gctgtgtact                                              20

<210> SEQ ID NO 129
<211> LENGTH: 20
<212> TYPE: DNA
<213> ORGANISM: Homo sapiens

<400> SEQUENCE: 129
gccacacctt aatatacatt                                              20
```

```
<210> SEQ ID NO 130
<211> LENGTH: 20
<212> TYPE: DNA
<213> ORGANISM: Homo sapiens

<400> SEQUENCE: 130
tcccactgct cctaaagcca                                               20

<210> SEQ ID NO 131
<211> LENGTH: 20
<212> TYPE: DNA
<213> ORGANISM: Homo sapiens

<400> SEQUENCE: 131
gtaccctccc actgctccta                                               20

<210> SEQ ID NO 132
<211> LENGTH: 20
<212> TYPE: DNA
<213> ORGANISM: Homo sapiens

<400> SEQUENCE: 132
tctgctggta ccctcccact                                               20

<210> SEQ ID NO 133
<211> LENGTH: 20
<212> TYPE: DNA
<213> ORGANISM: Homo sapiens

<400> SEQUENCE: 133
cctttctgct ggtaccctcc                                               20

<210> SEQ ID NO 134
<211> LENGTH: 20
<212> TYPE: DNA
<213> ORGANISM: Homo sapiens

<400> SEQUENCE: 134
gctatctgat gatactaacc                                               20

<210> SEQ ID NO 135
<211> LENGTH: 20
<212> TYPE: DNA
<213> ORGANISM: Homo sapiens

<400> SEQUENCE: 135
agcaggcata ttactcgtat                                               20

<210> SEQ ID NO 136
<211> LENGTH: 20
<212> TYPE: DNA
<213> ORGANISM: Homo sapiens

<400> SEQUENCE: 136
acacttcaaa tagcaggcat                                               20

<210> SEQ ID NO 137
<211> LENGTH: 20
<212> TYPE: DNA
<213> ORGANISM: Homo sapiens

<400> SEQUENCE: 137
tccttctcaa ttacacttca                                               20
```

```
<210> SEQ ID NO 138
<211> LENGTH: 20
<212> TYPE: DNA
<213> ORGANISM: Homo sapiens

<400> SEQUENCE: 138
ggtcagtgag cacgctaaaa                                              20

<210> SEQ ID NO 139
<211> LENGTH: 20
<212> TYPE: DNA
<213> ORGANISM: Homo sapiens

<400> SEQUENCE: 139
ggggctacag gcaggtcagt                                              20

<210> SEQ ID NO 140
<211> LENGTH: 20
<212> TYPE: DNA
<213> ORGANISM: Homo sapiens

<400> SEQUENCE: 140
tcctagctgt cactggggct                                              20

<210> SEQ ID NO 141
<211> LENGTH: 20
<212> TYPE: DNA
<213> ORGANISM: Homo sapiens

<400> SEQUENCE: 141
tgcacatcct agctgtcact                                              20

<210> SEQ ID NO 142
<211> LENGTH: 20
<212> TYPE: DNA
<213> ORGANISM: Homo sapiens

<400> SEQUENCE: 142
tcttgatggc tggagaatgc                                              20

<210> SEQ ID NO 143
<211> LENGTH: 20
<212> TYPE: DNA
<213> ORGANISM: Homo sapiens

<400> SEQUENCE: 143
ttgactcagt ctcttgatgg                                              20

<210> SEQ ID NO 144
<211> LENGTH: 20
<212> TYPE: DNA
<213> ORGANISM: Homo sapiens

<400> SEQUENCE: 144
ctgagtctgc tgttctgact                                              20

<210> SEQ ID NO 145
<211> LENGTH: 20
<212> TYPE: DNA
<213> ORGANISM: Homo sapiens

<400> SEQUENCE: 145
cagtgtcatt cgaatcagaa                                              20
```

<210> SEQ ID NO 146
<211> LENGTH: 20
<212> TYPE: DNA
<213> ORGANISM: Homo sapiens

<400> SEQUENCE: 146
ccgattcctg aacagtgtca                                          20

<210> SEQ ID NO 147
<211> LENGTH: 20
<212> TYPE: DNA
<213> ORGANISM: Homo sapiens

<400> SEQUENCE: 147
tcgacaggat tccgattcct                                          20

<210> SEQ ID NO 148
<211> LENGTH: 20
<212> TYPE: DNA
<213> ORGANISM: Homo sapiens

<400> SEQUENCE: 148
ccacaagctg tccagtctaa                                          20

<210> SEQ ID NO 149
<211> LENGTH: 20
<212> TYPE: DNA
<213> ORGANISM: Homo sapiens

<400> SEQUENCE: 149
tgccacaagc tgtccagtct                                          20

<210> SEQ ID NO 150
<211> LENGTH: 20
<212> TYPE: DNA
<213> ORGANISM: Homo sapiens

<400> SEQUENCE: 150
cacttgccac aagctgtcca                                          20

<210> SEQ ID NO 151
<211> LENGTH: 20
<212> TYPE: DNA
<213> ORGANISM: Homo sapiens

<400> SEQUENCE: 151
gttacaggca aattcacttg                                          20

<210> SEQ ID NO 152
<211> LENGTH: 20
<212> TYPE: DNA
<213> ORGANISM: Homo sapiens

<400> SEQUENCE: 152
attaacttag ataactgtac                                          20

<210> SEQ ID NO 153
<211> LENGTH: 20
<212> TYPE: DNA
<213> ORGANISM: Homo sapiens

<400> SEQUENCE: 153
ggcacaaaca actttaaatt                                              20

<210> SEQ ID NO 154
<211> LENGTH: 20
<212> TYPE: DNA
<213> ORGANISM: Homo sapiens

<400> SEQUENCE: 154
cagaaattga ggctaacatt                                              20

<210> SEQ ID NO 155
<211> LENGTH: 20
<212> TYPE: DNA
<213> ORGANISM: Homo sapiens

<400> SEQUENCE: 155
cattctacct atggtgttca                                              20

<210> SEQ ID NO 156
<211> LENGTH: 20
<212> TYPE: DNA
<213> ORGANISM: Homo sapiens

<400> SEQUENCE: 156
gctttacatt ctacctatgg                                              20

<210> SEQ ID NO 157
<211> LENGTH: 20
<212> TYPE: DNA
<213> ORGANISM: Homo sapiens

<400> SEQUENCE: 157
acgatcagac aagctttaca                                              20

<210> SEQ ID NO 158
<211> LENGTH: 20
<212> TYPE: DNA
<213> ORGANISM: Homo sapiens

<400> SEQUENCE: 158
gtatccattt catgctttga                                              20

<210> SEQ ID NO 159
<211> LENGTH: 20
<212> TYPE: DNA
<213> ORGANISM: Homo sapiens

<400> SEQUENCE: 159
ccatataagt atccatttca                                              20

<210> SEQ ID NO 160
<211> LENGTH: 20
<212> TYPE: DNA
<213> ORGANISM: Homo sapiens

<400> SEQUENCE: 160
actgtcattc tatctgagca                                              20

<210> SEQ ID NO 161
<211> LENGTH: 20
<212> TYPE: DNA
<213> ORGANISM: Homo sapiens

<400> SEQUENCE: 161
acggactgtc attctatctg                                              20

<210> SEQ ID NO 162
<211> LENGTH: 20
<212> TYPE: DNA
<213> ORGANISM: Homo sapiens

<400> SEQUENCE: 162
atgcctcccc tttgcaaaca                                              20

<210> SEQ ID NO 163
<211> LENGTH: 20
<212> TYPE: DNA
<213> ORGANISM: Homo sapiens

<400> SEQUENCE: 163
cactgatgcc tccctttgc                                               20

<210> SEQ ID NO 164
<211> LENGTH: 20
<212> TYPE: DNA
<213> ORGANISM: Homo sapiens

<400> SEQUENCE: 164
acctagaaat cagcctgcca                                              20

<210> SEQ ID NO 165
<211> LENGTH: 20
<212> TYPE: DNA
<213> ORGANISM: Homo sapiens

<400> SEQUENCE: 165
ggctaccaca tttcctacct                                              20

<210> SEQ ID NO 166
<211> LENGTH: 20
<212> TYPE: DNA
<213> ORGANISM: Homo sapiens

<400> SEQUENCE: 166
gccatttgtt cattaaaagt                                              20

<210> SEQ ID NO 167
<211> LENGTH: 20
<212> TYPE: DNA
<213> ORGANISM: Homo sapiens

<400> SEQUENCE: 167
agtcactcag tttttaataa                                              20

<210> SEQ ID NO 168
<211> LENGTH: 20
<212> TYPE: DNA
<213> ORGANISM: Homo sapiens

<400> SEQUENCE: 168
gctatataga gtcactcagt                                              20

<210> SEQ ID NO 169
<211> LENGTH: 20
<212> TYPE: DNA
<213> ORGANISM: Homo sapiens

```
<400> SEQUENCE: 169
gcttccaggt gaaaaaactg                                               20

<210> SEQ ID NO 170
<211> LENGTH: 20
<212> TYPE: DNA
<213> ORGANISM: Homo sapiens

<400> SEQUENCE: 170
aacaaatgct tccaggtgaa                                               20

<210> SEQ ID NO 171
<211> LENGTH: 20
<212> TYPE: DNA
<213> ORGANISM: Homo sapiens

<400> SEQUENCE: 171
agtagaaaca aatgcttcca                                               20

<210> SEQ ID NO 172
<211> LENGTH: 20
<212> TYPE: DNA
<213> ORGANISM: Homo sapiens

<400> SEQUENCE: 172
gtccgaaaaa cagtcatatc                                               20

<210> SEQ ID NO 173
<211> LENGTH: 20
<212> TYPE: DNA
<213> ORGANISM: Homo sapiens

<400> SEQUENCE: 173
ctcaacaaat aaactgtccg                                               20

<210> SEQ ID NO 174
<211> LENGTH: 20
<212> TYPE: DNA
<213> ORGANISM: Homo sapiens

<400> SEQUENCE: 174
atacacttta ttttcaacta                                               20

<210> SEQ ID NO 175
<211> LENGTH: 20
<212> TYPE: DNA
<213> ORGANISM: Homo sapiens

<400> SEQUENCE: 175
gcacgtgcac tggtacttgc                                               20

<210> SEQ ID NO 176
<211> LENGTH: 20
<212> TYPE: DNA
<213> ORGANISM: Homo sapiens

<400> SEQUENCE: 176
ccaggcacgt gcactggtac                                               20

<210> SEQ ID NO 177
<211> LENGTH: 20
<212> TYPE: DNA
<213> ORGANISM: Homo sapiens
```

<400> SEQUENCE: 177
caggcccaac cacggtttgg                                           20

<210> SEQ ID NO 178
<211> LENGTH: 20
<212> TYPE: DNA
<213> ORGANISM: Homo sapiens

<400> SEQUENCE: 178
agggcaggcc caaccacggt                                           20

<210> SEQ ID NO 179
<211> LENGTH: 20
<212> TYPE: DNA
<213> ORGANISM: Homo sapiens

<400> SEQUENCE: 179
gtcttccagt cggtaagccg                                           20

<210> SEQ ID NO 180
<211> LENGTH: 20
<212> TYPE: DNA
<213> ORGANISM: Homo sapiens

<400> SEQUENCE: 180
acgtgtcttc cagtcggtaa                                           20

<210> SEQ ID NO 181
<211> LENGTH: 20
<212> TYPE: DNA
<213> ORGANISM: Homo sapiens

<400> SEQUENCE: 181
caggcagttg gctctaatca                                           20

<210> SEQ ID NO 182
<211> LENGTH: 20
<212> TYPE: DNA
<213> ORGANISM: Homo sapiens

<400> SEQUENCE: 182
accaggcagt tggctctaat                                           20

<210> SEQ ID NO 183
<211> LENGTH: 20
<212> TYPE: DNA
<213> ORGANISM: Homo sapiens

<400> SEQUENCE: 183
ctggaccagg cagttggctc                                           20

<210> SEQ ID NO 184
<211> LENGTH: 20
<212> TYPE: DNA
<213> ORGANISM: Homo sapiens

<400> SEQUENCE: 184
gtctggacca ggcagttggc                                           20

<210> SEQ ID NO 185
<211> LENGTH: 20
<212> TYPE: DNA

```
<213> ORGANISM: Homo sapiens

<400> SEQUENCE: 185
ttggtaaccc gggtggagat                                              20

<210> SEQ ID NO 186
<211> LENGTH: 20
<212> TYPE: DNA
<213> ORGANISM: Homo sapiens

<400> SEQUENCE: 186
cattggtaac ccgggtggag                                              20

<210> SEQ ID NO 187
<211> LENGTH: 20
<212> TYPE: DNA
<213> ORGANISM: Homo sapiens

<400> SEQUENCE: 187
ttgtcattgg taacccgggt                                              20

<210> SEQ ID NO 188
<211> LENGTH: 20
<212> TYPE: DNA
<213> ORGANISM: Homo sapiens

<400> SEQUENCE: 188
cgttgtcatt ggtaacccgg                                              20

<210> SEQ ID NO 189
<211> LENGTH: 20
<212> TYPE: DNA
<213> ORGANISM: Homo sapiens

<400> SEQUENCE: 189
gcctgaccat gcacaggcgg                                              20

<210> SEQ ID NO 190
<211> LENGTH: 20
<212> TYPE: DNA
<213> ORGANISM: Homo sapiens

<400> SEQUENCE: 190
aggcctgacc atgcacaggc                                              20

<210> SEQ ID NO 191
<211> LENGTH: 20
<212> TYPE: DNA
<213> ORGANISM: Homo sapiens

<400> SEQUENCE: 191
cgcaaggcct gaccatgcac                                              20

<210> SEQ ID NO 192
<211> LENGTH: 20
<212> TYPE: DNA
<213> ORGANISM: Homo sapiens

<400> SEQUENCE: 192
ttcgcaaggc ctgaccatgc                                              20

<210> SEQ ID NO 193
<211> LENGTH: 20
```

```
<212> TYPE: DNA
<213> ORGANISM: Homo sapiens

<400> SEQUENCE: 193 tgcactttt gcccttctta                                              20

<210> SEQ ID NO 194
<211> LENGTH: 20
<212> TYPE: DNA
<213> ORGANISM: Homo sapiens

<400> SEQUENCE: 194
gatgcacttt ttgcccttct                                             20

<210> SEQ ID NO 195
<211> LENGTH: 20
<212> TYPE: DNA
<213> ORGANISM: Homo sapiens

<400> SEQUENCE: 195
tacggatgca cttttttgccc                                            20

<210> SEQ ID NO 196
<211> LENGTH: 20
<212> TYPE: DNA
<213> ORGANISM: Homo sapiens

<400> SEQUENCE: 196
gagtacggat gcacttttg                                              20

<210> SEQ ID NO 197
<211> LENGTH: 20
<212> TYPE: DNA
<213> ORGANISM: Homo sapiens

<400> SEQUENCE: 197
ttgggagtac ggatgcactt                                             20

<210> SEQ ID NO 198
<211> LENGTH: 20
<212> TYPE: DNA
<213> ORGANISM: Homo sapiens

<400> SEQUENCE: 198
ttttgggagt acggatgcac                                             20

<210> SEQ ID NO 199
<211> LENGTH: 20
<212> TYPE: DNA
<213> ORGANISM: Homo sapiens

<400> SEQUENCE: 199
ttgataggct tggagatttt                                             20

<210> SEQ ID NO 200
<211> LENGTH: 20
<212> TYPE: DNA
<213> ORGANISM: Homo sapiens

<400> SEQUENCE: 200
aaacttgata ggcttggaga                                             20

<210> SEQ ID NO 201
```

```
<211> LENGTH: 20
<212> TYPE: DNA
<213> ORGANISM: Homo sapiens

<400> SEQUENCE: 201
agccagaaag ctcaaacttg                                         20

<210> SEQ ID NO 202
<211> LENGTH: 20
<212> TYPE: DNA
<213> ORGANISM: Homo sapiens

<400> SEQUENCE: 202
gtgcagccag aaagctcaaa                                         20

<210> SEQ ID NO 203
<211> LENGTH: 20
<212> TYPE: DNA
<213> ORGANISM: Homo sapiens

<400> SEQUENCE: 203
catgctggtg cagccagaaa                                         20

<210> SEQ ID NO 204
<211> LENGTH: 20
<212> TYPE: DNA
<213> ORGANISM: Homo sapiens

<400> SEQUENCE: 204
ttcatgctgg tgcagccaga                                         20

<210> SEQ ID NO 205
<211> LENGTH: 20
<212> TYPE: DNA
<213> ORGANISM: Homo sapiens

<400> SEQUENCE: 205
tgtcttcatg ctggtgcagc                                         20

<210> SEQ ID NO 206
<211> LENGTH: 20
<212> TYPE: DNA
<213> ORGANISM: Homo sapiens

<400> SEQUENCE: 206
tatgtcttca tgctggtgca                                         20

<210> SEQ ID NO 207
<211> LENGTH: 20
<212> TYPE: DNA
<213> ORGANISM: Homo sapiens

<400> SEQUENCE: 207
atttagctcg gtatgtcttc                                         20

<210> SEQ ID NO 208
<211> LENGTH: 20
<212> TYPE: DNA
<213> ORGANISM: Homo sapiens

<400> SEQUENCE: 208
acagaattta gctcggtatg                                         20
```

```
<210> SEQ ID NO 209
<211> LENGTH: 20
<212> TYPE: DNA
<213> ORGANISM: Homo sapiens

<400> SEQUENCE: 209
tactccacag aatttagctc                                              20

<210> SEQ ID NO 210
<211> LENGTH: 20
<212> TYPE: DNA
<213> ORGANISM: Homo sapiens

<400> SEQUENCE: 210
cgtcggtaca tactccacag                                              20

<210> SEQ ID NO 211
<211> LENGTH: 20
<212> TYPE: DNA
<213> ORGANISM: Homo sapiens

<400> SEQUENCE: 211
cggccgtcgg tacatactcc                                              20

<210> SEQ ID NO 212
<211> LENGTH: 20
<212> TYPE: DNA
<213> ORGANISM: Homo sapiens

<400> SEQUENCE: 212
atcggccgtc ggtacatact                                              20

<210> SEQ ID NO 213
<211> LENGTH: 20
<212> TYPE: DNA
<213> ORGANISM: Homo sapiens

<400> SEQUENCE: 213
agcatcggcc gtcggtacat                                              20

<210> SEQ ID NO 214
<211> LENGTH: 20
<212> TYPE: DNA
<213> ORGANISM: Homo sapiens

<400> SEQUENCE: 214
gcagcatcgg ccgtcggtac                                              20

<210> SEQ ID NO 215
<211> LENGTH: 20
<212> TYPE: DNA
<213> ORGANISM: Homo sapiens

<400> SEQUENCE: 215
gggtgcagca tcggccgtcg                                              20

<210> SEQ ID NO 216
<211> LENGTH: 20
<212> TYPE: DNA
<213> ORGANISM: Homo sapiens

<400> SEQUENCE: 216
cttgaactcc accggcaggg                                              20
```

```
<210> SEQ ID NO 217
<211> LENGTH: 20
<212> TYPE: DNA
<213> ORGANISM: Homo sapiens

<400> SEQUENCE: 217
cacttgaact ccaccggcag                                          20

<210> SEQ ID NO 218
<211> LENGTH: 20
<212> TYPE: DNA
<213> ORGANISM: Homo sapiens

<400> SEQUENCE: 218
agggcacttg aactccaccg                                          20

<210> SEQ ID NO 219
<211> LENGTH: 20
<212> TYPE: DNA
<213> ORGANISM: Homo sapiens

<400> SEQUENCE: 219
tcagggcact tgaactccac                                          20

<210> SEQ ID NO 220
<211> LENGTH: 20
<212> TYPE: DNA
<213> ORGANISM: Homo sapiens

<400> SEQUENCE: 220
cgccgtcagg gcacttgaac                                          20

<210> SEQ ID NO 221
<211> LENGTH: 20
<212> TYPE: DNA
<213> ORGANISM: Homo sapiens

<400> SEQUENCE: 221
ctcgccgtca gggcacttga                                          20

<210> SEQ ID NO 222
<211> LENGTH: 20
<212> TYPE: DNA
<213> ORGANISM: Homo sapiens

<400> SEQUENCE: 222
tgacctcgcc gtcagggcac                                          20

<210> SEQ ID NO 223
<211> LENGTH: 20
<212> TYPE: DNA
<213> ORGANISM: Homo sapiens

<400> SEQUENCE: 223
catgacctcg ccgtcagggc                                          20

<210> SEQ ID NO 224
<211> LENGTH: 20
<212> TYPE: DNA
<213> ORGANISM: Homo sapiens

<400> SEQUENCE: 224
cacaggtctt gatgaacatc                                          20
```

```
<210> SEQ ID NO 225
<211> LENGTH: 20
<212> TYPE: DNA
<213> ORGANISM: Homo sapiens

<400> SEQUENCE: 225
caggcacagg tcttgatgaa                                               20

<210> SEQ ID NO 226
<211> LENGTH: 20
<212> TYPE: DNA
<213> ORGANISM: Homo sapiens

<400> SEQUENCE: 226
aatggcaggc acaggtcttg                                               20

<210> SEQ ID NO 227
<211> LENGTH: 20
<212> TYPE: DNA
<213> ORGANISM: Homo sapiens

<400> SEQUENCE: 227
ttgtaatggc aggcacaggt                                               20

<210> SEQ ID NO 228
<211> LENGTH: 20
<212> TYPE: DNA
<213> ORGANISM: Homo sapiens

<400> SEQUENCE: 228
gacagttgta atggcaggca                                               20

<210> SEQ ID NO 229
<211> LENGTH: 20
<212> TYPE: DNA
<213> ORGANISM: Homo sapiens

<400> SEQUENCE: 229
gggacagttg taatggcagg                                               20

<210> SEQ ID NO 230
<211> LENGTH: 20
<212> TYPE: DNA
<213> ORGANISM: Homo sapiens

<400> SEQUENCE: 230
ctccgggaca gttgtaatgg                                               20

<210> SEQ ID NO 231
<211> LENGTH: 20
<212> TYPE: DNA
<213> ORGANISM: Homo sapiens

<400> SEQUENCE: 231
gtctccggga cagttgtaat                                               20

<210> SEQ ID NO 232
<211> LENGTH: 20
<212> TYPE: DNA
<213> ORGANISM: Homo sapiens

<400> SEQUENCE: 232
```

```
atgtcattgt ctccgggaca                                              20

<210> SEQ ID NO 233
<211> LENGTH: 20
<212> TYPE: DNA
<213> ORGANISM: Homo sapiens

<400> SEQUENCE: 233
aaagatgtca ttgtctccgg                                              20

<210> SEQ ID NO 234
<211> LENGTH: 20
<212> TYPE: DNA
<213> ORGANISM: Homo sapiens

<400> SEQUENCE: 234
ttcatgccat gtctccgtac                                              20

<210> SEQ ID NO 235
<211> LENGTH: 20
<212> TYPE: DNA
<213> ORGANISM: Homo sapiens

<400> SEQUENCE: 235
tggcttcatg ccatgtctcc                                              20

<210> SEQ ID NO 236
<211> LENGTH: 20
<212> TYPE: DNA
<213> ORGANISM: Homo sapiens

<400> SEQUENCE: 236
accctcccac tgctcctaaa                                              20

<210> SEQ ID NO 237
<211> LENGTH: 20
<212> TYPE: DNA
<213> ORGANISM: Homo sapiens

<400> SEQUENCE: 237
gctggtaccc tcccactgct                                              20

<210> SEQ ID NO 238
<211> LENGTH: 20
<212> TYPE: DNA
<213> ORGANISM: Homo sapiens

<400> SEQUENCE: 238
tttctgctgg taccctccca                                              20

<210> SEQ ID NO 239
<211> LENGTH: 20
<212> TYPE: DNA
<213> ORGANISM: Homo sapiens

<400> SEQUENCE: 239
ctacaggcag gtcagtgagc                                              20

<210> SEQ ID NO 240
<211> LENGTH: 20
<212> TYPE: DNA
<213> ORGANISM: Homo sapiens

<400> SEQUENCE: 240
```

```
ggctacaggc aggtcagtga                                              20

<210> SEQ ID NO 241
<211> LENGTH: 20
<212> TYPE: DNA
<213> ORGANISM: Homo sapiens

<400> SEQUENCE: 241
ctggggctac aggcaggtca                                              20

<210> SEQ ID NO 242
<211> LENGTH: 20
<212> TYPE: DNA
<213> ORGANISM: Homo sapiens

<400> SEQUENCE: 242
cactggggct acaggcaggt                                              20

<210> SEQ ID NO 243
<211> LENGTH: 20
<212> TYPE: DNA
<213> ORGANISM: Homo sapiens

<400> SEQUENCE: 243
cacatcctag ctgtcactgg                                              20

<210> SEQ ID NO 244
<211> LENGTH: 20
<212> TYPE: DNA
<213> ORGANISM: Homo sapiens

<400> SEQUENCE: 244
aatgcacatc ctagctgtca                                              20

<210> SEQ ID NO 245
<211> LENGTH: 20
<212> TYPE: DNA
<213> ORGANISM: Homo sapiens

<400> SEQUENCE: 245
gacaggattc cgattcctga                                              20

<210> SEQ ID NO 246
<211> LENGTH: 20
<212> TYPE: DNA
<213> ORGANISM: Homo sapiens

<400> SEQUENCE: 246
aatcgacagg attccgattc                                              20

<210> SEQ ID NO 247
<211> LENGTH: 20
<212> TYPE: DNA
<213> ORGANISM: Homo sapiens

<400> SEQUENCE: 247
aagctgtcca gtctaatcga                                              20

<210> SEQ ID NO 248
<211> LENGTH: 20
<212> TYPE: DNA
<213> ORGANISM: Homo sapiens
```

```
<400> SEQUENCE: 248
acaagctgtc cagtctaatc                                               20

<210> SEQ ID NO 249
<211> LENGTH: 20
<212> TYPE: DNA
<213> ORGANISM: Homo sapiens

<400> SEQUENCE: 249
cttgccacaa gctgtccagt                                               20

<210> SEQ ID NO 250
<211> LENGTH: 20
<212> TYPE: DNA
<213> ORGANISM: Homo sapiens

<400> SEQUENCE: 250
ttcacttgcc acaagctgtc                                               20

<210> SEQ ID NO 251
<211> LENGTH: 20
<212> TYPE: DNA
<213> ORGANISM: Homo sapiens

<400> SEQUENCE: 251
aattcacttg ccacaagctg                                               20

<210> SEQ ID NO 252
<211> LENGTH: 20
<212> TYPE: DNA
<213> ORGANISM: Homo sapiens

<400> SEQUENCE: 252
tggtctggac caggcagttg                                               20

<210> SEQ ID NO 253
<211> LENGTH: 20
<212> TYPE: DNA
<213> ORGANISM: Homo sapiens

<400> SEQUENCE: 253
ttgcccttct taatgttctc                                               20

<210> SEQ ID NO 254
<211> LENGTH: 20
<212> TYPE: DNA
<213> ORGANISM: Homo sapiens

<400> SEQUENCE: 254
ttttgccctt cttaatgttc                                               20

<210> SEQ ID NO 255
<211> LENGTH: 20
<212> TYPE: DNA
<213> ORGANISM: Homo sapiens

<400> SEQUENCE: 255 cttttttgccc ttcttaatgt                                              20

<210> SEQ ID NO 256
<211> LENGTH: 20
<212> TYPE: DNA
<213> ORGANISM: Homo sapiens
```

```
<400> SEQUENCE: 256 cacttttgc ccttcttaat                                              20

<210> SEQ ID NO 257
<211> LENGTH: 20
<212> TYPE: DNA
<213> ORGANISM: Homo sapiens

<400> SEQUENCE: 257
ggagattttg ggagtacgga                                             20

<210> SEQ ID NO 258
<211> LENGTH: 20
<212> TYPE: DNA
<213> ORGANISM: Homo sapiens

<400> SEQUENCE: 258
cttggagatt ttgggagtac                                             20

<210> SEQ ID NO 259
<211> LENGTH: 20
<212> TYPE: DNA
<213> ORGANISM: Homo sapiens

<400> SEQUENCE: 259
taggcttgga gattttggga                                             20

<210> SEQ ID NO 260
<211> LENGTH: 20
<212> TYPE: DNA
<213> ORGANISM: Homo sapiens

<400> SEQUENCE: 260
tcaaacttga taggcttgga                                             20

<210> SEQ ID NO 261
<211> LENGTH: 20
<212> TYPE: DNA
<213> ORGANISM: Homo sapiens

<400> SEQUENCE: 261
ctggtgcagc cagaaagctc                                             20

<210> SEQ ID NO 262
<211> LENGTH: 20
<212> TYPE: DNA
<213> ORGANISM: Homo sapiens

<400> SEQUENCE: 262
tgctggtgca gccagaaagc                                             20

<210> SEQ ID NO 263
<211> LENGTH: 20
<212> TYPE: DNA
<213> ORGANISM: Homo sapiens

<400> SEQUENCE: 263
ggtatgtctt catgctggtg                                             20

<210> SEQ ID NO 264
<211> LENGTH: 20
<212> TYPE: DNA
```

```
<213> ORGANISM: Homo sapiens

<400> SEQUENCE: 264
tcggtatgtc ttcatgctgg                                              20

<210> SEQ ID NO 265
<211> LENGTH: 20
<212> TYPE: DNA
<213> ORGANISM: Homo sapiens

<400> SEQUENCE: 265
ttagctcggt atgtcttcat                                              20

<210> SEQ ID NO 266
<211> LENGTH: 20
<212> TYPE: DNA
<213> ORGANISM: Homo sapiens

<400> SEQUENCE: 266
ccacagaatt tagctcggta                                              20

<210> SEQ ID NO 267
<211> LENGTH: 20
<212> TYPE: DNA
<213> ORGANISM: Homo sapiens

<400> SEQUENCE: 267
ccgtcagggc acttgaactc                                              20

<210> SEQ ID NO 268
<211> LENGTH: 20
<212> TYPE: DNA
<213> ORGANISM: Homo sapiens

<400> SEQUENCE: 268
ttcatgacct cgccgtcagg                                              20

<210> SEQ ID NO 269
<211> LENGTH: 20
<212> TYPE: DNA
<213> ORGANISM: Homo sapiens

<400> SEQUENCE: 269
tcttcatgac ctcgccgtca                                              20

<210> SEQ ID NO 270
<211> LENGTH: 20
<212> TYPE: DNA
<213> ORGANISM: Homo sapiens

<400> SEQUENCE: 270
ttcttcttca tgacctcgcc                                              20

<210> SEQ ID NO 271
<211> LENGTH: 20
<212> TYPE: DNA
<213> ORGANISM: Homo sapiens

<400> SEQUENCE: 271
tggcaggcac aggtcttgat                                              20

<210> SEQ ID NO 272
<211> LENGTH: 20
```

```
<212> TYPE: DNA
<213> ORGANISM: Homo sapiens

<400> SEQUENCE: 272
agttgtaatg gcaggcacag                                              20

<210> SEQ ID NO 273
<211> LENGTH: 20
<212> TYPE: DNA
<213> ORGANISM: Homo sapiens

<400> SEQUENCE: 273
ttgtctccgg gacagttgta                                              20

<210> SEQ ID NO 274
<211> LENGTH: 20
<212> TYPE: DNA
<213> ORGANISM: Homo sapiens

<400> SEQUENCE: 274
cattgtctcc gggacagttg                                              20

<210> SEQ ID NO 275
<211> LENGTH: 20
<212> TYPE: DNA
<213> ORGANISM: Homo sapiens

<400> SEQUENCE: 275
gtcattgtct ccgggacagt                                              20

<210> SEQ ID NO 276
<211> LENGTH: 20
<212> TYPE: DNA
<213> ORGANISM: Homo sapiens

<400> SEQUENCE: 276
tcaaagatgt cattgtctcc                                              20

<210> SEQ ID NO 277
<211> LENGTH: 20
<212> TYPE: DNA
<213> ORGANISM: Homo sapiens

<400> SEQUENCE: 277
attcaaagat gtcattgtct                                              20

<210> SEQ ID NO 278
<211> LENGTH: 20
<212> TYPE: DNA
<213> ORGANISM: Homo sapiens

<400> SEQUENCE: 278
cgattcaaag atgtcattgt                                              20

<210> SEQ ID NO 279
<211> LENGTH: 20
<212> TYPE: DNA
<213> ORGANISM: Homo sapiens

<400> SEQUENCE: 279
agcgattcaa agatgtcatt                                              20

<210> SEQ ID NO 280
```

-continued

```
<211> LENGTH: 20
<212> TYPE: DNA
<213> ORGANISM: Homo sapiens

<400> SEQUENCE: 280
tagtacagcg attcaaagat                                                 20

<210> SEQ ID NO 281
<211> LENGTH: 20
<212> TYPE: DNA
<213> ORGANISM: Homo sapiens

<400> SEQUENCE: 281
cctgtagtac agcgattcaa                                                 20

<210> SEQ ID NO 282
<211> LENGTH: 20
<212> TYPE: DNA
<213> ORGANISM: Homo sapiens

<400> SEQUENCE: 282
catgccatgt ctccgtacat                                                 20

<210> SEQ ID NO 283
<211> LENGTH: 20
<212> TYPE: DNA
<213> ORGANISM: Homo sapiens

<400> SEQUENCE: 283
tctggcttca tgccatgtct                                                 20

<210> SEQ ID NO 284
<211> LENGTH: 20
<212> TYPE: DNA
<213> ORGANISM: Homo sapiens

<400> SEQUENCE: 284
tctctggctt catgccatgt                                                 20

<210> SEQ ID NO 285
<211> LENGTH: 20
<212> TYPE: DNA
<213> ORGANISM: Homo sapiens

<400> SEQUENCE: 285
ttgtgctact gaaatcattt                                                 20

<210> SEQ ID NO 286
<211> LENGTH: 20
<212> TYPE: DNA
<213> ORGANISM: Homo sapiens

<400> SEQUENCE: 286
taacttgtgc tactgaaatc                                                 20

<210> SEQ ID NO 287
<211> LENGTH: 20
<212> TYPE: DNA
<213> ORGANISM: Homo sapiens

<400> SEQUENCE: 287
cctcccactg ctcctaaagc                                                 20
```

```
<210> SEQ ID NO 288
<211> LENGTH: 20
<212> TYPE: DNA
<213> ORGANISM: Homo sapiens

<400> SEQUENCE: 288
tggtaccctc ccactgctcc                                           20

<210> SEQ ID NO 289
<211> LENGTH: 20
<212> TYPE: DNA
<213> ORGANISM: Homo sapiens

<400> SEQUENCE: 289
aacctttctg ctggtaccct                                           20

<210> SEQ ID NO 290
<211> LENGTH: 20
<212> TYPE: DNA
<213> ORGANISM: Homo sapiens

<400> SEQUENCE: 290
cagtgagcac gctaaaattt                                           20

<210> SEQ ID NO 291
<211> LENGTH: 20
<212> TYPE: DNA
<213> ORGANISM: Homo sapiens

<400> SEQUENCE: 291
gcaggtcagt gagcacgcta                                           20

<210> SEQ ID NO 292
<211> LENGTH: 20
<212> TYPE: DNA
<213> ORGANISM: Homo sapiens

<400> SEQUENCE: 292
aggcaggtca gtgagcacgc                                           20

<210> SEQ ID NO 293
<211> LENGTH: 20
<212> TYPE: DNA
<213> ORGANISM: Homo sapiens

<400> SEQUENCE: 293
acaggcaggt cagtgagcac                                           20

<210> SEQ ID NO 294
<211> LENGTH: 20
<212> TYPE: DNA
<213> ORGANISM: Homo sapiens

<400> SEQUENCE: 294
gtcactgggg ctacaggcag                                           20

<210> SEQ ID NO 295
<211> LENGTH: 20
<212> TYPE: DNA
<213> ORGANISM: Homo sapiens

<400> SEQUENCE: 295
ctgtcactgg ggctacaggc                                           20
```

```
<210> SEQ ID NO 296
<211> LENGTH: 20
<212> TYPE: DNA
<213> ORGANISM: Homo sapiens

<400> SEQUENCE: 296
agctgtcact ggggctacag                                               20

<210> SEQ ID NO 297
<211> LENGTH: 20
<212> TYPE: DNA
<213> ORGANISM: Homo sapiens

<400> SEQUENCE: 297
ctagctgtca ctggggctac                                               20

<210> SEQ ID NO 298
<211> LENGTH: 20
<212> TYPE: DNA
<213> ORGANISM: Homo sapiens

<400> SEQUENCE: 298
catcctagct gtcactgggg                                               20

<210> SEQ ID NO 299
<211> LENGTH: 20
<212> TYPE: DNA
<213> ORGANISM: Homo sapiens

<400> SEQUENCE: 299
gattcctgaa cagtgtcatt                                               20

<210> SEQ ID NO 300
<211> LENGTH: 20
<212> TYPE: DNA
<213> ORGANISM: Homo sapiens

<400> SEQUENCE: 300
attccgattc ctgaacagtg                                               20

<210> SEQ ID NO 301
<211> LENGTH: 20
<212> TYPE: DNA
<213> ORGANISM: Homo sapiens

<400> SEQUENCE: 301
ggattccgat tcctgaacag                                               20

<210> SEQ ID NO 302
<211> LENGTH: 20
<212> TYPE: DNA
<213> ORGANISM: Homo sapiens

<400> SEQUENCE: 302
caggattccg attcctgaac                                               20

<210> SEQ ID NO 303
<211> LENGTH: 20
<212> TYPE: DNA
<213> ORGANISM: Homo sapiens

<400> SEQUENCE: 303
ctaatcgaca ggattccgat                                               20
```

```
<210> SEQ ID NO 304
<211> LENGTH: 20
<212> TYPE: DNA
<213> ORGANISM: Homo sapiens

<400> SEQUENCE: 304
gtctaatcga caggattccg                                              20

<210> SEQ ID NO 305
<211> LENGTH: 20
<212> TYPE: DNA
<213> ORGANISM: Homo sapiens

<400> SEQUENCE: 305
cagtctaatc gacaggattc                                              20

<210> SEQ ID NO 306
<211> LENGTH: 20
<212> TYPE: DNA
<213> ORGANISM: Homo sapiens

<400> SEQUENCE: 306
tccagtctaa tcgacaggat                                              20

<210> SEQ ID NO 307
<211> LENGTH: 20
<212> TYPE: DNA
<213> ORGANISM: Homo sapiens

<400> SEQUENCE: 307
tgtccagtct aatcgacagg                                              20

<210> SEQ ID NO 308
<211> LENGTH: 20
<212> TYPE: DNA
<213> ORGANISM: Homo sapiens

<400> SEQUENCE: 308
gctgtccagt ctaatcgaca                                              20

<210> SEQ ID NO 309
<211> LENGTH: 20
<212> TYPE: DNA
<213> ORGANISM: Homo sapiens

<400> SEQUENCE: 309
caaattcact tgccacaagc                                              20

<210> SEQ ID NO 310
<211> LENGTH: 20
<212> TYPE: DNA
<213> ORGANISM: Homo sapiens

<400> SEQUENCE: 310
ggcaaattca cttgccacaa                                              20

<210> SEQ ID NO 311
<211> LENGTH: 20
<212> TYPE: DNA
<213> ORGANISM: Homo sapiens

<400> SEQUENCE: 311
```

```
caggcaaatt cacttgccac                                              20

<210> SEQ ID NO 312
<211> LENGTH: 20
<212> TYPE: DNA
<213> ORGANISM: Homo sapiens

<400> SEQUENCE: 312
tacaggcaaa ttcacttgcc                                              20

<210> SEQ ID NO 313
<211> LENGTH: 20
<212> TYPE: DNA
<213> ORGANISM: Homo sapiens

<400> SEQUENCE: 313
ttaacttaga taactgtaca                                              20

<210> SEQ ID NO 314
<211> LENGTH: 20
<212> TYPE: DNA
<213> ORGANISM: Homo sapiens

<400> SEQUENCE: 314
caaatgcttc caggtgaaaa                                              20

<210> SEQ ID NO 315
<211> LENGTH: 20
<212> TYPE: DNA
<213> ORGANISM: Homo sapiens

<400> SEQUENCE: 315
gaaacaaatg cttccaggtg                                              20

<210> SEQ ID NO 316
<211> LENGTH: 20
<212> TYPE: DNA
<213> ORGANISM: Homo sapiens

<400> SEQUENCE: 316
ggtcacactc tcaacaaata                                              20

<210> SEQ ID NO 317
<211> LENGTH: 20
<212> TYPE: DNA
<213> ORGANISM: Homo sapiens

<400> SEQUENCE: 317
aaacatgtaa cttttggtca                                              20

<210> SEQ ID NO 318
<211> LENGTH: 22
<212> TYPE: DNA
<213> ORGANISM: Homo sapiens

<400> SEQUENCE: 318
aagtaccagt gcacgtgcct gg                                           22

<210> SEQ ID NO 319
<211> LENGTH: 26
<212> TYPE: DNA
<213> ORGANISM: Homo sapiens

<400> SEQUENCE: 319
```

```
attagagcca actgcctggt ccagac                                           26

<210> SEQ ID NO 320
<211> LENGTH: 22
<212> TYPE: DNA
<213> ORGANISM: Homo sapiens

<400> SEQUENCE: 320
ccacccgggt taccaatgac aa                                               22

<210> SEQ ID NO 321
<211> LENGTH: 43
<212> TYPE: DNA
<213> ORGANISM: Homo sapiens

<400> SEQUENCE: 321
aagagaacat taagaagggc aaaaagtgca tccgtactcc caa                        43

<210> SEQ ID NO 322
<211> LENGTH: 22
<212> TYPE: DNA
<213> ORGANISM: Homo sapiens

<400> SEQUENCE: 322
actcccaaaa tctccaagcc ta                                               22

<210> SEQ ID NO 323
<211> LENGTH: 22
<212> TYPE: DNA
<213> ORGANISM: Homo sapiens

<400> SEQUENCE: 323
aatctccaag cctatcaagt tt                                               22

<210> SEQ ID NO 324
<211> LENGTH: 39
<212> TYPE: DNA
<213> ORGANISM: Homo sapiens

<400> SEQUENCE: 324
agtttgagct ttctggctgc accagcatga agacatacc                             39

<210> SEQ ID NO 325
<211> LENGTH: 24
<212> TYPE: DNA
<213> ORGANISM: Homo sapiens

<400> SEQUENCE: 325
atgaagacat accgagctaa attc                                             24

<210> SEQ ID NO 326
<211> LENGTH: 29
<212> TYPE: DNA
<213> ORGANISM: Homo sapiens

<400> SEQUENCE: 326
agtatgtacc gacggccgat gctgcaccc                                        29

<210> SEQ ID NO 327
<211> LENGTH: 39
<212> TYPE: DNA
<213> ORGANISM: Homo sapiens
```

<400> SEQUENCE: 327
ctgccggtgg agttcaagtg ccctgacggc gaggtcatg                              39

<210> SEQ ID NO 328
<211> LENGTH: 22
<212> TYPE: DNA
<213> ORGANISM: Homo sapiens

<400> SEQUENCE: 328
acggcgaggt catgaagaag aa                                               22

<210> SEQ ID NO 329
<211> LENGTH: 31
<212> TYPE: DNA
<213> ORGANISM: Homo sapiens

<400> SEQUENCE: 329
atcaagacct gtgcctgcca ttacaactgt c                                     31

<210> SEQ ID NO 330
<211> LENGTH: 38
<212> TYPE: DNA
<213> ORGANISM: Homo sapiens

<400> SEQUENCE: 330
tgccattaca actgtcccgg agacaatgac atctttga                              38

<210> SEQ ID NO 331
<211> LENGTH: 22
<212> TYPE: DNA
<213> ORGANISM: Homo sapiens

<400> SEQUENCE: 331
ctttgaatcg ctgtactaca gg                                               22

<210> SEQ ID NO 332
<211> LENGTH: 30
<212> TYPE: DNA
<213> ORGANISM: Homo sapiens

<400> SEQUENCE: 332
atgtacggag acatggcatg aagccagaga                                       30

<210> SEQ ID NO 333
<211> LENGTH: 22
<212> TYPE: DNA
<213> ORGANISM: Homo sapiens

<400> SEQUENCE: 333
atgatttcag tagcacaagt ta                                               22

<210> SEQ ID NO 334
<211> LENGTH: 39
<212> TYPE: DNA
<213> ORGANISM: Homo sapiens

<400> SEQUENCE: 334
tggctttagg agcagtggga gggtaccagc agaaaggtt                             39

<210> SEQ ID NO 335
<211> LENGTH: 34
<212> TYPE: DNA
<213> ORGANISM: Homo sapiens

```
<400> SEQUENCE: 335
tagcgtgctc actgacctgc ctgtagcccc agtg                              34

<210> SEQ ID NO 336
<211> LENGTH: 22
<212> TYPE: DNA
<213> ORGANISM: Homo sapiens

<400> SEQUENCE: 336
ccagtgacag ctaggatgtg ca                                           22

<210> SEQ ID NO 337
<211> LENGTH: 25
<212> TYPE: DNA
<213> ORGANISM: Homo sapiens

<400> SEQUENCE: 337
aatgacactg ttcaggaatc ggaat                                        25

<210> SEQ ID NO 338
<211> LENGTH: 28
<212> TYPE: DNA
<213> ORGANISM: Homo sapiens

<400> SEQUENCE: 338
gttcaggaat cggaatcctg tcgattag                                     28

<210> SEQ ID NO 339
<211> LENGTH: 38
<212> TYPE: DNA
<213> ORGANISM: Homo sapiens

<400> SEQUENCE: 339
gaatcctgtc gattagactg gacagcttgt ggcaagtg                          38

<210> SEQ ID NO 340
<211> LENGTH: 28
<212> TYPE: DNA
<213> ORGANISM: Homo sapiens

<400> SEQUENCE: 340
cagcttgtgg caagtgaatt tgcctgta                                     28
```

CONNECTIVE TISSUE GROWTH FACTOR ANTISENSE OLIGONUCLEOTIDES

This application claims the benefit of U.S. Provisional Application Ser. No. 61/508,264, filed on 15 Jul. 2011.

FIELD OF THE INVENTION

The present invention provides compounds, compositions and methods for modulating the expression of human connective tissue growth factor (CTGF). In particular, this invention relates to antisense oligonucleotides (ASOs) capable of modulating human CTGF mRNA expression that are useful for treating disorders and conditions involving dysregulated CTGF expression or that are influenced by the normal expression of CTGF.

BACKGROUND OF THE INVENTION

CTGF is a 36 kD cysteine-rich, heparin binding, secreted glycoprotein originally isolated from the culture media of human umbilical vein endothelial cells. See e.g., Bradham et al. *J Cell Biol*. (1991) 114; 1285-1294; Grotendorst and Bradham, U.S. Pat. No. 5,408,040. CTGF promotes the proliferation and chemotaxis of various cell types in culture. Additionally, CTGF increases steady-state transcription of α1(I) collagen, α5 integrin, and fibronectin mRNAs. See e.g., Frazier et al. *J Invest Dermatol*. (1996) 107:406-411; Shi-wen et al. *Exp Cell Res*. (2000) 259:213-224; Klagsburn *Exp Cell Res*. (1977) 105:99-108; Gupta et al. *Kidney Int*. (2000) 58:1389-1399; Wahab et al. *Biochem J*. (2001) 359(Pt 1):77-87; Uzel et al. *J Periodontol*. (2001) 72:921-931; and Riser and Cortes *Ren Fail*. (2001) 23:459-470.

Through the promotion of cellular chemotaxis and proliferation along with an increase in expression of extracellular matrix (ECM) components, CTGF plays a role in regulating skeletal development, wound healing, ECM remodeling, fibrosis, tumorigenesis and angiogenesis. For example, elevated CTGF expression has been observed in cirrhotic liver, pulmonary fibrosis, inflammatory bowel disease, sclerotic skin and keloids, desmoplasia and atherosclerotic plaques. Abraham et al. *J Biol Chem*. (2000) 275:15220-15225; Dammeier et al. *Int. J Biochem Cell Biol*. (1998) 30:909-922; diMola et al. *Ann Surg*. (1999) 230(1):63-71; Igarashi et al. *J Invest Dermatol*. (1996) 106:729-733; Ito et al. *Kidney Int*. (1998) 53:853-861; Williams et al. *J. Hepatol*. (2000) 32:754-761; Clarkson et al. *Curr Opin Nephrol. Hypertens*. (1999) 8:543-548; Hinton et al. *Eye*. (2002): 16:422-428; Gupta et al. *Kidney Int*. (2000) 58:1389-1399; Riser et al. *J Am Soc Nephrol*. (2000) 11:25-38.

CTGF is also upregulated in glomerulonephritis, IgA nephropathy, focal and segmental glomerulosclerosis and diabetic nephropathy. See, e.g., Riser et al. *J Am Soc Nephrol*. (2000) 11:25-38. An increase in the number of cells expressing CTGF mRNA is also observed at sites of chronic tubulointerstitial damage, with CTGF mRNA levels correlated with the degree of damage. Ito et al. *Kidney Int*. (1998) 53:853-861. Additionally, CTGF expression is increased in the glomeruli and tubulointerstium in a variety of renal diseases in association with scarring and sclerosis of renal parenchyma. Elevated levels of CTGF have also been associated with liver fibrosis, myocardial infarction, and pulmonary fibrosis. For example, in patients with idiopathic pulmonary fibrosis (IPF), CTGF is highly enriched in biopsies and bronchoalveolar lavage cells. (Ujike et al. *Biochem Biophys Res Commun*. (2000) 277:448-454; Abou-Shady et al. *Liver*. (2000) 20:296-304; Williams et al. *J Hepatol*. (2000) 32:754-761; Ohnishi et al. *J Mol Cell Cardiol*. (1998) 30:2411-22; Lasky et al. *Am J Physiol*. (1998) 275: L365-371; Pan et al. *Eur Respir J*. (2001) 17:1220-1227; and Allen et al. *Am J Respir Cell Mol Biol*. (1999) 21:693-700) Thus, CTGF represents a valid therapeutic target in disorders, such as those described above.

Given the prevalence and severity of CTGF-associated diseases and disorders, there is clearly a need for improved methods of treatment that can modulate CTGF expression. Antisense oligonucleotides represent exceptional therapeutic agents based on their target specificity. The present invention discloses antisense oligonucleotide compositions and methods of use for modulating CTGF expression that can meet these therapeutic needs.

SUMMARY OF THE INVENTION

The present invention is directed to synthetic, i.e., non-naturally occurring, antisense oligonucleotides that are complementary to nucleic acids encoding human CTGF and modulate CTGF mRNA expression. The disclosed antisense oligonucleotides are useful for decreasing or inhibiting cellular CTGF mRNA and CTGF protein expression. Additionally, pharmaceutical and other compositions comprising the antisense oligonucleotides of the invention are provided as well as methods of their use for the prevention or treatment of CTGF-associated health conditions or diseases. Regions of the human CTGF mRNA that are hypersensitive to inhibition by antisense oligonucleotides are also disclosed.

In one aspect of the invention, a compound is provided comprising a synthetic oligonucleotide 8 to 50 nucleotides in length where at least a contiguous 8 nucleotide sequence of the oligonucleotide is complementary to a region from nucleotides 567 to 588, 859 to 880, 981 to 1002, 989 to 1010, 1061 to 1089, 1132 to 1153, 1179 to 1216, 1211 to 1232, 1329 to 1350, 1623 to 1656, 1651 to 1672, 1750 to 1774, 1759 to 1786 or 1793 to 1820 of SEQ ID NO: 1.

In one embodiment of the invention, at least an 8 nucleotide contiguous sequence of the oligonucleotide is complementary to a region from nucleotides 567 to 588 of SEQ ID NO: 1.

In a further embodiment, at least an 8 nucleotide contiguous sequence of oligonucleotide is complementary to a region from nucleotides 859 to 880 of SEQ ID NO: 1.

In another embodiment, at least an 8 nucleotide contiguous sequence of the oligonucleotide is complementary to a region from nucleotides 981 to 1002 of SEQ ID NO: 1.

In one embodiment, at least an 8 nucleotide contiguous sequence of the oligonucleotide is complementary to a region from nucleotides 989 to 1010 of SEQ ID NO: 1.

In another embodiment, at least an 8 nucleotide contiguous sequence of the oligonucleotide is complementary to a region from nucleotides 1061 to 1089 of SEQ ID NO: 1.

In a further embodiment, at least an 8 nucleotide contiguous sequence of the oligonucleotide is complementary to a region from nucleotides 1132 to 1153 of SEQ ID NO: 1.

In one embodiment, at least an 8 nucleotide contiguous sequence of the oligonucleotide is complementary to a region from nucleotides 1179 to 1216 of SEQ ID NO: 1.

In another embodiment, at least an 8 nucleotide contiguous sequence of the oligonucleotide is complementary to a region from nucleotides 1211 to 1232 of SEQ ID NO: 1.

In a further embodiment, at least an 8 nucleotide contiguous sequence of the oligonucleotide is complementary to a region from nucleotides 1329 to 1350 of SEQ ID NO: 1.

In a one embodiment, at least an 8 nucleotide contiguous sequence of the oligonucleotide is complementary to a region from nucleotides 1623 to 1656 of SEQ ID NO: 1.

In another embodiment, at least, an 8 nucleotide contiguous sequence of the oligonucleotide is complementary to a region from nucleotides 1651 to 1672 of SEQ ID NO: 1.

In a further embodiment, at least an 8 nucleotide contiguous sequence of the oligonucleotide is complementary to a region from nucleotides 1750 to 1774 of SEQ ID NO: 1.

In a one embodiment, at least an 8 nucleotide contiguous sequence of the oligonucleotide is complementary to a region from nucleotides 1759 to 1786 of SEQ ID NO: 1.

In another embodiment, at least an 8 nucleotide contiguous sequence of the oligonucleotide is complementary to a region from nucleotides 1793 to 1820 of SEQ ID NO: 1.

In one aspect of the invention, compound is provided comprising a synthetic oligonucleotide 8 to 50 nucleotides in length, wherein at least a contiguous 8 nucleotide sequence of the oligonucleotide is complementary to a region selected from the group of regions consisting of SEQ ID NO: 318 to SEQ ID NO: 340.

In a further aspect of the invention, a synthetic oligonucleotide is provided selected from the group consisting of SEQ ID NO: 49, SEQ ID NO: 56, SEQ ID NO: 62, SEQ ID NO: 182, SEQ ID NO: 66, SEQ ID NO: 183, SEQ ID NO: 184, SEQ ID NO: 71, SEQ ID NO: 187, SEQ ID NO: 75, SEQ ID NO: 76, SEQ ID NO: 77, SEQ ID NO: 192, SEQ ID NO: 79, SEQ ID NO: 80, SEQ ID NO: 253, SEQ ID NO: 254, SEQ ID NO: 255, SEQ ID NO: 256, SEQ ID NO: 193, SEQ ID NO: 81, SEQ ID NO: 195, SEQ ID NO: 196, SEQ ID NO: 82, SEQ ID NO: 197, SEQ ID NO: 83, SEQ ID NO: 259, SEQ ID NO: 84, SEQ ID NO: 200, SEQ ID NO: 87, SEQ ID NO: 262, SEQ ID NO: 203, SEQ ID NO: 204, SEQ ID NO: 204, SEQ ID NO: 88, SEQ ID NO: 205, SEQ ID NO: 206, SEQ ID NO: 263, SEQ ID NO: 265, SEQ ID NO: 207, SEQ ID NO: 90, SEQ ID NO: 91, SEQ ID NO: 92, SEQ ID NO: 212, SEQ ID NO: 213, SEQ ID NO: 214, SEQ ID NO: 93; SEQ ID NO: 215, SEQ ID NO: 217, SEQ ID NO: 99, SEQ ID NO: 218, SEQ ID NO: 219, SEQ ID NO: 220, SEQ ID NO: 221, SEQ ID NO: 100, SEQ ID NO: 222, SEQ ID NO: 223, SEQ ID NO: 101, SEQ ID NO: 270, SEQ ID NO: 103, SEQ ID NO: 271, SEQ ID NO: 226, SEQ ID NO: 104, SEQ ID NO: 227, SEQ ID NO: 272, SEQ ID NO: 105, SEQ ID NO: 230, SEQ ID NO: 231, SEQ ID NO: 273, SEQ ID NO: 274, SEQ ID NO: 275, SEQ ID NO: 232, SEQ ID NO: 106, SEQ ID NO: 233, SEQ ID NO: 276, SEQ ID NO: 279, SEQ ID NO: 108, SEQ ID NO: 281, SEQ ID NO: 109, SEQ ID NO: 282, SEQ ID NO: 234, SEQ ID NO: 111, SEQ ID NO: 235, SEQ ID NO: 284, SEQ ID NO: 118, SEQ ID NO: 286, SEQ ID NO: 289, SEQ ID NO: 299, SEQ ID NO: 146, SEQ ID NO: 300, SEQ ID NO: 302, SEQ ID NO: 245, SEQ ID NO: 147, SEQ ID NO: 246, SEQ ID NO: 303, SEQ ID NO: 305, SEQ ID NO: 306, SEQ ID NO: 307, SEQ ID NO: 247, SEQ ID NO: 248, SEQ ID NO: 149, SEQ ID NO: 150, SEQ ID NO: 251, SEQ ID NO: 309, SEQ ID NO: 310, SEQ ID NO: 311, SEQ ID NO: 312 and SEQ ID NO: 170.

In one embodiment, the oligonucleotide has at least one internucleoside linkage, at least one sugar moiety, or at least one nucleobase that is modified. In a further embodiment, the modified internucleoside linkage is a phosphothioate internucleoside linkage. In a still further embodiment, all of the internucleoside linkages of the oligonucleotide are phosphothioate internucleoside linkages.

In another embodiment, at least one modified sugar moiety of the oligonucleotide is a bicyclic sugar. In a further embodiment, the modified sugar comprises a 2'-O,4'-C-methylene bridge.

In one embodiment, at least one modified nucleobase of the oligonucleotide is a 5-methylcytosine.

In one aspect of the invention, a method for reducing the expression of human CTGF mRNA is provided that comprises administering an effective amount of an oligonucleotide of the invention to a subject in need thereof, thereby reducing the expression of human CTGF mRNA.

In another aspect of the invention, a method of treating a CTGF-associated disorder is provided that comprises administering an effective amount of an oligonucleotide of the invention to a subject in need thereof, thereby treating the CTGT-associated disorder. In some embodiments, the CTGF-associated disease, condition or disorder is selected from the group consisting of dermal fibrosis, liver fibrosis, pulmonary fibrosis, renal fibrosis, cardiac fibrosis, ocular fibrosis, scleroderma, surgical scars and adhesions, scars from wounds, scars from burns, restenosis, glomerular sclerosis, osteoarthritis and cancer. In further embodiments, the cancer is selected from the group consisting of acute lymphoblastic leukemia, dermatofibromas, breast cancer, breast carcinoma desmoplasia, angiolipoma, angioleiomyoma, desmoplastic cancer, prostate cancer, ovarian cancer, colorectal cancer, pancreatic cancer, gastrointestinal cancer, and liver cancer.

BRIEF DESCRIPTION OF THE DRAWINGS

FIG. 1 provides the nucleotide sequence of the entire spliced human CTGF mRNA sequence (NCBI Reference Sequence NM_001901; SEQ ID NO: 1), wherein thymidine is substituted for uridine. The 2358-base sequence includes five exons: bases 1-272, 273-495, 406-747, 748-959 and 960-2344, respectively with the coding sequences from bases 207-1256.

FIG. 6A represents nucleotides 1-450 of human CTGF mRNA and illustrates exon 1 and a portion of exon 2. FIG. 6B represents nucleotides 450-900 of human CTGF mRNA and illustrates exon 3 and portions of exon 2 and exon 4. FIG. 6C represents nucleotides 900-1350 of human CTGF mRNA and illustrates exon 5 and portions of exon 4 and the 3' UTR. FIGS. 6D and 6E represent nucleotides 1375-1825 and 1825-2275, respectively, of human CTGF mRNA and illustrate the remaining portions of the 3' UTR.

DETAILED DESCRIPTION OF THE INVENTION

Figure 2:
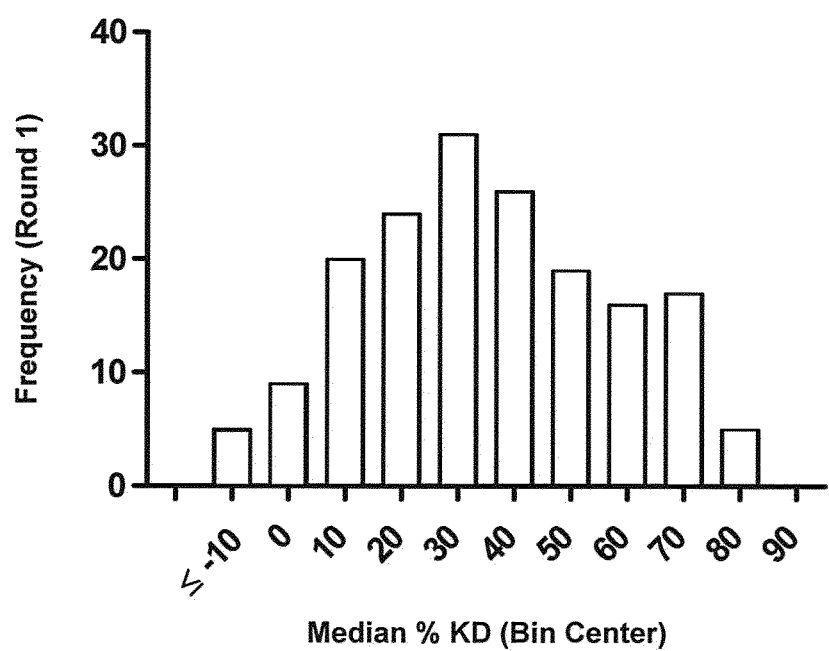
FIG. 2 is a histogram that shows the distribution of Round 1 antisense oligonucleotides based on the percent inhibition of CTGF mRNA expression (knock down) compared to vehicle-treated control. A small shoulder is visible on the right side of the expected bell-shaped curve of a normal (Gaussian) distribution indicating the presence of a larger than expected sub-population of potent antisense oligonucleotides that induce significant reduction in CTGF mRNA expression.

The present invention comprises synthetic antisense oligonucleotides that modulate the expression of human CTGF mRNA. These antisense oligonucleotides include isolated nucleic acids, nucleic acid mimetics, and combinations thereof. Also disclosed are regions of human CTGF mRNA that are hypersensitive to antisense oligonucleotide mediated inhibition of mRNA expression. Antisense oligonucleotides that modulate the expression of CTGF mRNA are useful in situations where modulation of CTGF mRNA expression represents an important intervention point in the treatment of a CTGF-associated disease, condition of disorder. Modulation includes up-regulation or down-regulation of the transcription rate of mRNA, rate or fidelity of splicing of pre-mRNA, total cellular mRNA level, rate of mRNA translation, and/or total cellular, tissue or organ CTGF protein levels. Down-regulation of the expression of CTGF mRNA can result in a decrease in or cessation of cellular growth, a decrease in cellular replication, a decrease in cellular motility, a decrease in cellular metabolism and/or the induction of apoptosis. Additionally, down-regulation of expression of CTGF mRNA can also result in alleviation of symptoms and improvement, cure or prevention of CTCF-associated diseases, conditions or disorders.

Definitions

The terms "nucleic acid" or "polynucleotide" refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, all nucleic acid sequences disclosed herein are expressed in the 5'-3' direction. Additionally, unless otherwise indicated, a particular nucleic acid sequence in addition to explicitly indicating the disclosed sequence also implicitly encompasses conservatively modified variants thereof (e.g., degenerate codon substitutions), alleles, and complementary sequences.

The term "oligonucleotide" and "oligomeric nucleic acid" refer to oligomers or polymers of ribonucleic acid (RNA), deoxyribonucleic acid (DNA), mimetics or analogs of RNA or DNA, or combinations thereof. Oligonucleotides are molecules formed by the covalent linkage of two or more nucleotides or their analogs. Herein, a single nucleotide may also be referred to as a monomer or unit. The oligonucleotides of the invention comprise contiguous nucleotide sequences between 8 to 50 nucleotides in length. In some embodiments, the contiguous nucleotide sequences are at least 8, 9, 10, 11, 12, 13, 14, 15, 16, 17, 18, 19, 20, 21, 22, 23, 24, 25, 26, 28, 30, 32, 34, 36, 38, 40, 42, 44, 46, or 48 nucleotides in length. In other embodiments, the contiguous nucleotide sequences are not more than 10, 11, 12, 13, 14, 15, 16, 17, 18, 19, 20, 21, 22, 23, 24, 25, 26, 28, 30, 32, 34, 36, 38, 40, 42, 44, 46, 48, or 50 nucleotides in length. In further embodiments, the contiguous nucleotide sequences are between 8 and 40, between 8 and 30, between 8 and 24, between 8 and 20, between 10 and 40, between 10 and 30, between 10 and 24, between 10 and 20, between 12 and 40, between 12 and 30, between 12 and 24, between 12 and 20, between 13 and 30, between 13 and 24, between 13 and 20, between 16 and 24, or between 16 and 20 nucleotides in length. Unless otherwise indicated, all oligonucleotide sequences disclosed herein are expressed in the 5'-3' direction.

Oligonucleotides of the invention are linear molecules or are synthesized as linear molecules. Preferably, the oligonucleotides do not form duplexes between sequences within individual molecules, in other words, the oligonucleotides are not substantially self-complementary. In some embodiments, the oligonucleotides are essential not doubled stranded, i.e., not short hairpin RNA. In other embodiments, the oligonucleotides are single stranded. In some embodiments, the oligonucleotides are not small interfering RNAs (siRNAs). In other embodiments, the oligonucleotides of the invention are not ribozymes, external guide sequence (EGS) oligonucleotides (oligozymes), or other short catalytic RNAs.

The terms "small interfering RNA" or "siRNA" refer to single- or double-stranded RNA, molecules that induce the RNA-interference pathway and act in concert with host proteins, e.g., RNA induced silencing complex (RISC) to degrade mRNA in a sequence-dependent fashion.

The terms "complementary" and "complementarity" refer to conventional Watson-Crick base-pairing of nucleic acids. For example, in DNA complementarity, guanine forms a base pair with cytosine and adenine forms a base pair with thymine, whereas in RNA complementarity, guanine forms a base pair with cytosine, but adenine forms a base pair with uracil in place of thymine. An oligonucleotide is complementary to a RNA or DNA sequence when the nucleotides of the oligonucleotide are capable of forming hydrogen bonds with a sufficient number of nucleotides in the corresponding RNA or DNA sequence to allow the oligonucleotide to hybridize with the RNA or DNA sequence. In some embodiments, the antisense oligonucleotides of the invention have perfect complementarity to human CTGF mRNA, i.e., no mismatches.

As used herein, the terms "antisense oligonucleotide" and "ASO" refer to an oligomeric nucleic acid that is capable of hybridizing with its complementary target nucleic acid sequence resulting in the modulation of the normal function of the target nucleic acid sequence. In some embodiments, the modulation of function is the interference in function of DNA, typically resulting in decreased replication and/or transcription of a target DNA. In other embodiments, the modulation of function is the interference in function of RNA, typically resulting in impaired splicing of transcribed RNA (pre-mRNA) to yield mature mRNA species, reduced RNA stability, decreased translocation of the target mRNA to the site of protein translation and impaired translation of protein from mature mRNA. In other embodiments, the modulation of function is the reduction in cellular target mRNA (CTGF) number or cellular content of target mRNA (CTGF). In some embodiments, the modulation of function is the down-regulation or knockdown of gene expression. In other embodiments, the modulation of function is a reduction in protein expression or cellular protein content. In further embodiments, the modulation of function is a phenotypic change associated with the reduction of CTGF including a reversion to a normal phenotype. In some embodiments, the change in phenotype includes a change in a cell's proliferation rate, migration rate, metastatic potential, apoptosis rate, or sensitivity to chemotherapy agents, biologic agents or radiation. In other embodiments, the change in phenotype includes a change in the rate of tissue remodeling or deposition of extracellular matrix. In some embodiments, a reduction in CTGF is associated with the reduction or alleviation of a symptom of a CTGF-associated disease, condition or disorder.

The antisense oligonucleotides provided herein may be defined by a particular nucleotide sequence or SEQ ID NO. As used herein, an antisense oligonucleotide is identical to a sequence disclosed herein if it has the same nucleotide base pairing ability. For example, a RNA sequence that contains uracil in place of thymidine in a disclosed DNA sequence would be considered identical to the DNA sequence since both uracil and thymidine pair with adenine. Shortened and lengthened versions of the antisense oligonucleotides described herein are also contemplated.

The antisense oligonucleotides of the invention effectively inhibit CTGF mRNA expression by at least 10%, 20%, 30%, 40%, 50%, 55% 60%, 65%, 70%, 75%, 80%, 90% or 95% of that seen with vehicle treated controls i.e., cells exposed only to the transfection agent and the PBS vehicle, but not an antisense oligonucleotide. For example, the ASO SEQ ID NO: 246 inhibited CTGF mRNA expression by 65% over that seen with the transfection agent in PBS. In other embodiments, the administration of an antisense oligonucleotide target to a CTGF nucleic acid results in the reduction of CTGF mRNA expression of not more than about 10%, 15%, 20%, 25%, 30%, 35%, 40%, 45%, 50%, 55%, 60%, 65%, 70%, 75%, 80%, 85%, 90% or 95% of that seen with vehicle-treated controls. In still other embodiments, the administration of an antisense oligonucleotide target to a CTGF nucleic acid results in the reduction of CTGF mRNA expression between about 10% and about 90%, about 20% and about 80%, about 30% and about 70%, about 40% and about 60%, about 40% and about 70%, and about 40% and about 80% of the expression level of vehicle treated controls.

The modulation of the CTGF mRNA or protein expression level can be determined using any of the standard molecular biology techniques known to the art. For instance, mRNA levels can be determined using northern blotting or quantitative RT-PCR, while protein levels can be measured using ELISA, SDS-PAGE followed by western blotting or by mass spectrometry.

As used herein, the terms "potent antisense oligonucleotide" or "potent ASO" refer to an antisense oligonucleotide that has a surprisingly strong inhibitory effect on CTGF mRNA expression. Potent antisense oligonucleotides reduce the expression of human CTGF mRNA or protein by at least 50% compared to the expression level of vehicle-treated controls. Potent antisense oligonucleotides of the invention comprise a sequence selected from the group consisting of SEQ ID NO: 43, SEQ ID NO: 176, SEQ ID NO: 49, SEQ ID NO: 56, SEQ ID NO: 60, SEQ ID NO: 62, SEQ ID NO: 182, SEQ ID NO: 66, SEQ ID NO: 183, SEQ ID NO: 184, SEQ ID NO: 71, SEQ ID NO: 187, SEQ ID NO: 75, SEQ ID NO: 76, SEQ ID NO: 77, SEQ ID NO: 192, SEQ ID NO: 79, SEQ ID NO: 80, SEQ ID NO: 253, SEQ ID NO: 254, SEQ ID NO: 255, SEQ ID NO: 256, SEQ ID NO: 193, SEQ ID NO: 81, SEQ ID NO: 195, SEQ ID NO: 196, SEQ ID NO: 82, SEQ ID NO: 197, SEQ ID NO: 83, SEQ ID NO: 259, SEQ ID NO: 84, SEQ ID NO: 200, SEQ ID NO: 87, SEQ ID NO: 262, SEQ ID NO: 203, SEQ ID NO: 204, SEQ ID NO: 204, SEQ ID NO: 88, SEQ ID NO: 205, SEQ ID NO: 206, SEQ ID NO: 263, SEQ ID NO: 265, SEQ ID NO: 207, SEQ ID NO: 90, SEQ ID NO: 91, SEQ ID NO: 92, SEQ ID NO: 212, SEQ ID NO: 213, SEQ ID NO: 214; SEQ ID NO: 93; SEQ ID NO: 215, SEQ ID NO: 217, SEQ ID NO: 99, SEQ ID NO: 218, SEQ ID NO: 219, SEQ ID NO: 220, SEQ ID NO: 221, SEQ ID NO: 100, SEQ ID NO: 222, SEQ ID NO: 223, SEQ ID NO: 101, SEQ ID NO: 270, SEQ ID NO: 103, SEQ ID NO: 271, SEQ ID NO: 226, SEQ ID NO: 104, SEQ ID NO: 227, SEQ ID NO: 272, SEQ ID NO: 105, SEQ ID NO: 230, SEQ ID NO: 231, SEQ ID NO: 273, SEQ ID NO: 274, SEQ ID NO: 275, SEQ ID NO: 232, SEQ ID NO: 106, SEQ ID NO: 233, SEQ ID NO: 276, SEQ ID NO: 279, SEQ ID NO: 108, SEQ ID NO: 281, SEQ ID NO: 109, SEQ ID NO: 282, SEQ ID NO: 234, SEQ ID NO: 111, SEQ ID NO: 235, SEQ ID NO: 284, SEQ ID NO: 118, SEQ ID NO: 286, SEQ ID NO: 130, SEQ ID NO: 287, SEQ ID NO: 236, SEQ ID NO: 288, SEQ ID NO: 237, SEQ ID NO: 132, SEQ ID NO: 238, SEQ ID NO: 133, SEQ ID NO: 289, SEQ ID NO: 135, SEQ ID NO: 291, SEQ ID NO: 292, SEQ ID NO: 293, SEQ ID NO: 239, SEQ ID NO: 240, SEQ ID NO: 139, SEQ ID NO: 241, SEQ ID NO: 242, SEQ ID NO: 296, SEQ ID NO: 243, SEQ ID NO: 141, SEQ ID NO: 289, SEQ ID NO: 299, SEQ ID NO: 146, SEQ ID NO: 300, SEQ ID NO: 302, SEQ ID NO: 245, SEQ ID NO: 147, SEQ ID NO: 246, SEQ ID NO: 303, SEQ ID NO: 305, SEQ ID NO: 306, SEQ ID NO: 307, SEQ ID NO: 247, SEQ ID NO: 248, SEQ ID NO: 149, SEQ ID NO: 150, SEQ ID NO: 251, SEQ ID NO: 309, SEQ ID NO: 310, SEQ ID NO: 311, SEQ ID NO: 312, SEQ ID NO: 163 and SEQ ID NO: 170

In some embodiments, the potent antisense oligonucleotides reduce the expression of human CTGF mRNA or protein by at least 55% compared to the expression level of vehicle-treated controls, i.e., SEQ ID NO: 43, SEQ ID NO: 176, SEQ ID NO: 49, SEQ ID NO: 60, SEQ ID NO: 62, SEQ ID NO: 182, SEQ ID NO: 66, SEQ ID NO: 183, SEQ ID NO: 184, SEQ ID NO: 71, SEQ ID NO: 187, SEQ ID NO: 77, SEQ ID NO: 192, SEQ ID NO: 80, SEQ ID NO: 253, SEQ ID NO: 254, SEQ ID NO: 255, SEQ ID NO: 256, SEQ ID NO: 193, SEQ ID NO: 81, SEQ ID NO: 195, SEQ ID NO: 196, SEQ ID NO: 82, SEQ ID NO: 197, SEQ ID NO: 83, SEQ ID NO: 259, SEQ ID NO: 84, SEQ ID NO: 200, SEQ ID NO: 87, SEQ ID NO: 262, SEQ ID NO: 203, SEQ ID NO: 204, SEQ ID NO: 204, SEQ ID NO: 88, SEQ ID NO: 205, SEQ ID NO: 206, SEQ ID NO: 207, SEQ ID NO: 90, SEQ ID NO: 91, SEQ ID NO: 92, SEQ ID NO: 212, SEQ ID NO: 213, SEQ ID NO: 214, SEQ ID NO: 93, SEQ ID NO: 215, SEQ ID NO: 99, SEQ ID NO: 218, SEQ ID NO: 219, SEQ ID NO: 220, SEQ ID NO: 221, SEQ ID NO: 100, SEQ ID NO: 222, SEQ ID NO: 223, SEQ ID NO: 101, SEQ ID NO: 102, SEQ ID NO: 226, SEQ ID NO: 104, SEQ ID NO: 227, SEQ ID NO: 105, SEQ ID NO: 230, SEQ ID NO: 231, SEQ ID NO: 273, SEQ ID NO: 274, SEQ ID NO: 275, SEQ ID NO: 232, SEQ ID NO: 106, SEQ ID NO: 233, SEQ ID NO: 279, SEQ ID NO: 108, SEQ ID NO: 281, SEQ ID NO: 109, SEQ ID NO: 282, SEQ ID NO: 234, SEQ ID NO: 111, SEQ ID NO: 235, SEQ ID NO: 284, SEQ ID NO: 118, SEQ ID NO: 286, SEQ ID NO: 130, SEQ ID NO: 287, SEQ ID NO: 236, SEQ ID NO: 288, SEQ ID NO: 237, SEQ ID NO: 132, SEQ ID NO: 133, SEQ ID NO: 289, SEQ ID NO: 135, SEQ ID NO: 291, SEQ ID NO: 292, SEQ ID NO: 293, SEQ ID NO: 239, SEQ ID NO: 240, SEQ ID NO: 139, SEQ ID NO: 241, SEQ ID NO: 242, SEQ ID NO: 243, SEQ ID NO: 141, SEQ ID NO: 146, SEQ ID NO: 245, SEQ ID NO: 147, SEQ ID NO: 246, SEQ ID NO: 303, SEQ ID NO: 305, SEQ ID NO: 306, SEQ ID NO: 307, SEQ ID NO: 247, SEQ ID NO: 248, SEQ ID NO: 149, SEQ ID NO: 150, SEQ ID NO: 251, SEQ ID NO: 309, and SEQ ID NO: 170.

In some embodiments, the potent antisense oligonucleotides reduce the expression of human CTGF mRNA or protein by at least 60% compared to the expression level of vehicle-treated controls, i.e., SEQ ID NO: 43, SEQ ID NO: 60; SEQ ID NO: 62, SEQ ID NO: 66, SEQ ID NO: 183, SEQ ID NO: 192, SEQ ID NO: 80, SEQ ID NO: 253, SEQ ID NO: 193, SEQ ID NO: 81, SEQ ID NO: 195, SEQ ID NO: 196, SEQ ID NO: 82, SEQ ID NO: 197, SEQ ID NO: 259, SEQ ID NO: 84, SEQ ID NO: 200, SEQ ID NO: 87, SEQ ID NO: 262, SEQ ID NO: 203, SEQ ID NO: 204, SEQ ID NO: 204, SEQ ID NO: 88, SEQ ID NO: 205, SEQ ID NO: 206, SEQ ID NO: 207, SEQ ID NO: 90, SEQ ID NO: 91, SEQ ID NO: 92, SEQ ID NO: 213, SEQ ID NO: 214, SEQ ID NO: 93, SEQ ID NO: 215, SEQ ID NO: 99, SEQ ID NO: 218, SEQ ID NO: 219, SEQ ID NO: 220, SEQ ID NO: 221, SEQ ID NO: 100, SEQ ID NO: 222, SEQ ID NO: 223, SEQ ID NO: 103, SEQ ID NO: 226, SEQ ID NO: 104, SEQ ID NO: 227, SEQ ID NO: 105, SEQ ID NO: 230, SEQ ID NO: 231, SEQ ID NO: 273, SEQ ID NO: 274, SEQ ID NO: 275, SEQ ID NO: 232; SEQ ID NO: 106, SEQ ID NO: 233, SEQ ID NO: 281, SEQ ID NO: 234, SEQ ID NO: 111, SEQ ID NO: 235, SEQ ID NO: 284, SEQ ID NO: 236, SEQ ID NO: 237, SEQ ID NO: 132, SEQ ID NO: 289, SEQ ID NO: 291, SEQ ID NO: 292, SEQ ID NO: 239, SEQ ID NO: 240, SEQ ID NO: 139, SEQ ID NO: 241, SEQ ID NO: 242, SEQ ID NO: 141, SEQ ID NO: 245, SEQ ID NO: 147, SEQ ID NO: 246, SEQ ID NO: 305, SEQ ID NO: 307, SEQ ID NO: 247, SEQ ID NO: 149, SEQ ID NO: 150 and SEQ ID NO: 251.

In some embodiments, the potent antisense oligonucleotides reduce the expression of human CTGF mRNA or protein by at least 65% compared to the expression level of vehicle-treated controls, i.e., SEQ ID NO: 60, SEQ ID NO: 62, SEQ ID NO: 66, SEQ ID NO: 183, SEQ ID NO: 253, SEQ ID NO: 193, SEQ ID NO: 81, SEQ ID NO: 195, SEQ ID NO: 196, SEQ ID NO: 82, SEQ ID NO: 197, SEQ ID NO: 200, SEQ ID NO: 262, SEQ ID NO: 203, SEQ ID NO: 204, SEQ ID NO: 204, SEQ ID NO: 88, SEQ ID NO: 205; SEQ ID NO: 206, SEQ ID NO: 207, SEQ ID NO: 90, SEQ ID NO: 91, SEQ ID NO: 92, SEQ ID NO: 213, SEQ ID NO: 214, SEQ ID NO: 93, SEQ ID NO: 215, SEQ ID NO: 99, SEQ ID NO: 218, SEQ ID NO: 219, SEQ ID NO: 220, SEQ ID NO: 221, SEQ ID NO: 100, SEQ ID NO: 222, SEQ ID NO: 223, SEQ ID NO: 226, SEQ ID NO: 104, SEQ ID NO: 105, SEQ ID NO: 231, SEQ ID NO: 273, SEQ ID NO: 274, SEQ ID NO: 232, SEQ ID NO: 106, SEQ ID NO: 233, SEQ ID NO: 234, SEQ ID NO: 111, SEQ ID NO: 235, SEQ ID NO: 284, SEQ ID NO: 236, SEQ ID NO: 237, SEQ ID NO: 289, SEQ ID NO: 240, SEQ ID NO: 139, SEQ ID NO: 242, SEQ ID NO: 246, SEQ ID NO: 307, SEQ ID NO: 149 and SEQ ID NO: 150.

In some embodiments, the potent antisense reduce the expression of human CTGF mRNA or protein by at least 70% compared to the expression level of vehicle-treated controls, i.e., SEQ ID NO: 253, SEQ ID NO: 193, SEQ ID NO: 195, SEQ ID NO: 196, SEQ ID NO: 82, SEQ ID NO: 204, SEQ ID NO: 88, SEQ ID NO: 205, SEQ ID NO: 206, SEQ ID NO: 214, SEQ ID NO: 215, SEQ ID NO: 220, SEQ ID NO: 221, SEQ ID NO: 222, SEQ ID NO: 274, SEQ ID NO: 232, SEQ ID NO: 234, SEQ ID NO: 235 and SEQ ID NO: 150.

In some embodiments, the potent antisense oligonucleotides reduce the expression of human CTGF mRNA or protein by at least 75% compared to the expression level of vehicle-treated controls, i.e., SEQ ID NO: 193, SEQ ID NO: 195, SEQ ID NO: 196, SEQ ID NO: 204, SEQ ID NO: 206 and SEQ ID NO: 222.

In some embodiments, the potent antisense oligonucleotides reduce the expression of human CTGF mRNA or protein by at least 80% compared to the expression level of vehicle-treated controls, i.e., SEQ ID NO: 204.

In other embodiments, the potent antisense oligonucleotides of the invention comprise a sequence selected from the group consisting of SEQ ID NO: 43, SEQ ID NO: 176, SEQ ID NO: 49, SEQ ID NO: 56, SEQ ID NO: 60, SEQ ID NO: 62, SEQ ID NO: 182, SEQ ID NO: 66, SEQ ID NO: 183, SEQ ID NO: 184, SEQ ID NO: 71, SEQ ID NO: 187, SEQ ID NO: 75; SEQ ID NO: 76; SEQ ID NO: 77, SEQ ID NO: 192, SEQ ID NO: 79, SEQ ID NO: 80, SEQ ID NO: 253, SEQ ID NO: 254, SEQ ID NO: 255, SEQ ID NO: 256, SEQ ID NO: 193, SEQ ID NO: 194, SEQ ID NO: 81, SEQ ID NO: 195, SEQ ID NO: 196, SEQ ID NO: 82, SEQ ID NO: 197, SEQ ID NO: 83, SEQ ID NO: 259, SEQ ID NO: 84, SEQ ID NO: 200, SEQ ID NO: 87, SEQ ID NO: 202, SEQ ID NO: 261, SEQ ID NO: 262, SEQ ID NO: 203, SEQ ID NO: 204, SEQ ID NO: 204, SEQ ID NO: 88, SEQ ID NO: 205, SEQ ID NO: 206, SEQ ID NO: 263, SEQ ID NO: 265, SEQ ID NO: 207, SEQ ID NO: 90, SEQ ID NO: 91, SEQ ID NO: 92, SEQ ID NO: 212, SEQ ID NO: 213, SEQ ID NO: 214, SEQ ID NO: 93, SEQ ID NO: 215, SEQ ID NO: 217, SEQ ID NO: 99, SEQ ID NO: 218, SEQ ID NO: 219, SEQ ID NO: 267, SEQ ID NO: 220, SEQ ID NO: 221, SEQ ID NO: 100, SEQ ID NO: 222, SEQ ID NO: 223, SEQ ID NO: 101, SEQ ID NO: 270, SEQ ID NO: 103, SEQ ID NO: 271, SEQ ID NO: 226, SEQ ID NO: 104, SEQ ID NO: 227, SEQ ID NO: 272, SEQ ID NO: 228, SEQ ID NO: 105, SEQ ID NO: 230, SEQ ID NO: 231, SEQ ID NO: 273, SEQ ID NO: 274, SEQ ID NO: 275, SEQ ID NO; 232, SEQ ID NO: 106, SEQ ID NO: 233, SEQ ID NO: 276, SEQ ID NO: 279, SEQ ID NO: 108, SEQ ID NO: 281, SEQ ID NO: 109, SEQ ID NO: 282, SEQ ID NO: 234, SEQ ID NO: 111, SEQ ID NO: 235, SEQ ID NO: 283, SEQ ID NO: 284, SEQ ID NO: 118, SEQ ID NO: 286, SEQ ID NO: 130, SEQ ID NO: 287, SEQ ID NO: 236, SEQ ID NO: 131, SEQ ID NO: 288, SEQ ID NO: 237, SEQ ID NO: 132, SEQ ID NO: 238, SEQ ID NO: 133, SEQ ID NO: 289, SEQ ID NO: 135, SEQ ID NO: 290, SEQ ID NO: 291, SEQ ID NO: 292, SEQ ID NO: 293, SEQ ID NO: 239, SEQ ID NO: 240, SEQ ID NO: 139, SEQ ID NO: 241, SEQ ID NO: 242, SEQ ID NO: 296, SEQ ID NO: 243, SEQ ID NO: 141, SEQ ID NO: 299, SEQ ID NO: 146, SEQ ID NO: 300, SEQ ID NO: 302, SEQ ID NO: 245, SEQ ID NO:

147, SEQ ID NO: 246, SEQ ID NO: 303, SEQ ID NO: 305, SEQ ID NO: 306, SEQ ID NO: 307, SEQ ID NO: 308, SEQ ID NO: 247, SEQ ID NO: 248, SEQ ID NO: 148, SEQ ID NO: 149, SEQ ID NO: 249, SEQ ID NO: 150, SEQ ID NO: 251, SEQ ID NO: 309, SEQ ID NO: 310, SEQ ID NO: 311, SEQ ID NO: 312, SEQ ID NO: 163 and SEQ ID NO: 170.

In some embodiments, the potent antisense oligonucleotides of the invention comprise a sequence selected from the group consisting of SEQ ID NO: 43 and SEQ ID NO: 176.

In further embodiments, the potent antisense oligonucleotides of the invention comprise a sequence selected from the group consisting of SEQ ID NO: 182, SEQ ID NO: 66, SEQ ID NO: 183 and SEQ ID NO: 184.

In some embodiments, the potent antisense oligonucleotides of the invention comprise a sequence selected from the group consisting of SEQ ID NO: 71 and SEQ ID NO: 187.

In further embodiments, the potent antisense oligonucleotides of the invention comprise a sequence selected from the group consisting of SEQ ID NO: 75 and SEQ ID NO: 76, In other embodiments, the potent antisense oligonucleotides of the invention comprise of a sequence selected from the group consisting of SEQ ID NO: 79, SEQ ID NO: 80, SEQ ID NO: 253, SEQ ID NO: 254, SEQ ID NO: 255, SEQ ID NO: 256, SEQ ID NO: 193, SEQ ID NO: 194, SEQ ID NO: 81, SEQ ID NO: 195, SEQ ID NO: 196, SEQ ID NO: 82 and SEQ ID NO: 197.

In some embodiments, the potent antisense oligonucleotides of the invention comprise a sequence selected from the group consisting of SEQ ID NO: 83 and SEQ ID NO: 259.

In other embodiments, the potent antisense oligonucleotides of the invention comprise a sequence selected from the group, consisting of SEQ ID NO: 84, and SEQ ID NO: 200.

In further embodiments, potent antisense oligonucleotides of the invention comprise a sequence selected from the group consisting of SEQ ID NO: 87, SEQ ID NO: 202, SEQ ID NO: 261, SEQ ID NO: 203, SEQ ID NO: 204, SEQ ID NO: 88, SEQ ID NO: 205, SEQ ID NO: 206 and SEQ ID NO: 263.

In certain embodiments, the potent antisense oligonucleotides of the invention comprise a sequence selected from the group consisting of SEQ ID NO: 265, SEQ ID NO: 207 and SEQ ID NO: 90.

In some embodiments, the potent antisense oligonucleotides of the invention comprise a sequence selected from the group consisting of SEQ ID NO: 212, SEQ ID NO: 213, SEQ ID NO: 214, SEQ ID NO: 93 and SEQ ID NO: 215.

In other embodiments, the potent antisense oligonucleotides of the invention comprise a sequence selected from the group consisting of SEQ ID NO: 217, SEQ ID NO: 99, SEQ ID NO: 218, SEQ ID NO: 219, SEQ ID NO: 267, SEQ ID NO: 220, SEQ ID NO: 221, SEQ ID NO: 100, SEQ ID NO: 222 and SEQ ID NO: 223.

In further embodiments, the potent antisense oligonucleotides of the invention comprise a sequence selected from the group consisting of SEQ ID NO: 101 and SEQ ID NO: 270.

In some embodiments, the potent antisense oligonucleotides of the invention comprise a sequence selected from the group consisting of SEQ ID NO: 271, SEQ ID NO: 226, SEQ ID NO: 104, SEQ ID NO: 227, SEQ ID NO: 272 and SEQ ID NO: 228.

In certain embodiments, the potent antisense oligonucleotides of the invention comprise a sequence selected from group consisting of SEQ ID NO: 105, SEQ ID NO: 230, SEQ ID NO: 231, SEQ ID NO: 273, SEQ ID NO: 274, SEQ ID NO: 275, SEQ ID NO: 232, SEQ ID NO: 106, SEQ ID NO: 233 and SEQ ID NO: 276.

In further embodiments, the potent antisense oligonucleotides of the invention comprise a sequence selected from the group consisting of SEQ ID NO: 108, SEQ ID NO: 281 and SEQ ID NO: 109.

In other embodiments, the potent antisense oligonucleotides of the invention comprise a sequence select from group consisting of SEQ ID NO: 282, SEQ ID NO: 234, SEQ ID NO: 111, SEQ ID NO: 235, SEQ ID NO: 283 and SEQ ID NO: 284.

In some embodiments, the potent antisense oligonucleotides of the invention comprise, a sequence selected from the group consisting of SEQ ID NO: 118 and SEQ ID NO: 286.

In further embodiments, the potent antisense oligonucleotides of the invention comprise a sequence selected from the group consisting of SEQ ID NO: 130, SEQ ID NO: 287, SEQ ID NO: 236, SEQ ID NO: 131, SEQ ID NO: 288, SEQ ID NO: 237, SEQ ID NO: 132, SEQ ID NO: 238, SEQ ID NO: 133 and SEQ ID NO: 289.

In some embodiments, the potent antisense oligonucleotides of the invention comprise a sequence selected from the group consisting of SEQ ID NO: 291, SEQ ID NO: 292; SEQ ID NO: 293, SEQ ID NO: 239, SEQ ID NO: 240, SEQ ID NO: 139, SEQ ID NO: 241, SEQ ID NO: 242.

In other embodiments, the potent antisense oligonucleotides of the invention comprise a sequence selected from the group consisting of SEQ ID NO: 296, SEQ ID NO: 243 and SEQ ID NO: 141.

In further embodiments, the potent antisense oligonucleotides of the invention comprise a sequence selected from the group consisting of SEQ ID NO: 299, SEQ ID NO: 146 and SEQ ID NO: 300.

In some embodiments, the potent antisense oligonucleotides of the invention comprise a sequence selected from the group consisting of SEQ ID NO: 302, SEQ ID NO: 245, SEQ ID NO: 147, SEQ ID NO: 246 and SEQ ID NO: 303.

In other embodiments, the potent antisense oligonucleotides of the invention comprise a sequence selected from the group consisting of SEQ ID NO: 305, SEQ ID NO: 306, SEQ ID NO: 307, SEQ ID NO: 308, SEQ ID NO: 247, SEQ ID NO: 248, SEQ ID NO: 148, SEQ ID NO: 149, SEQ ID NO: 249 and SEQ ID NO: 150.

In further embodiments, the potent antisense oligonucleotides of the invention comprise a sequence selected from the consisting of SEQ ID NO: 251, SEQ ID NO:309, SEQ ID NO: 310, SEQ ID NO: 311: and SEQ ID NO: 312.

It was further recognized, unexpectedly, that many of the target sequences of the potent antisense oligonucleotides are clustered at specific locations along the CTGF mRNA sequence as described below and shown in FIGS. 6A-6E and Table 2.

As used herein, the terms "modified" and "modification" when used in the context of the constituents of a nucleotide monomer, i.e., sugar, nucleobase and internucleoside linkage (backbone), refer to non-natural, changes to the chemical structure of these naturally occurring constituents or the substitutions of these constituents with non-naturally occurring ones, i.e., mimetics. For example, the "unmodified" or "naturally occurring" sugar ribose (RNA) can be modified by replacing the hydrogen at the 2-position of ribose with a methyl group. See Monia, B. P. et al. *J. Biol. Chem*, 268: 14514-14522, 1993. Similarly, the naturally occurring internucleoside linkage is a 3' to 5' phosphodiester linkage that can be modified by replacing one of the non-bridging phosphate oxygen atoms with a sulfur atom to create a phosphorothioate linkage. See Geiser T. *Ann N Y Acad Sci,* 616: 173-183, 1990.

When used in the context of an oligonucleotide, "modified" or "modification" refers to an oligonucleotide that incorporates one or more modified sugar, nucleobase of internucleoside linkage. Modified oligonucleotide are structurally distinguishable, but functionally interchangeable with naturally occurring of synthetic unmodified oligonucleotides and usually have enhanced properties such as increased resistance to degradation by exonucleases, or increased binding affinity.

It should be understood that the sequences set forth in SEQ ID NO format are independent of any modification to a sugar moiety, an internucleoside linkage, or a nucleobase. Therefore, an antisense oligonucleotide defined by a SEQ ID NO may comprise, independently, one or more modifications to a sugar moiety, an internucleoside linkage, or a nucleobase.

The term "target nucleic acid", as used herein refers to the DNA or RNA encoding human CTGF protein or naturally occurring variants thereof. The term "naturally occurring variant thereof" refers to variants of the human CTGF nucleic acid sequence which exist naturally within the population including any allelic variant, chromosomal translocation or duplication, or alternative splicing of human CTGF mRNA. In some embodiments, the RNA is mature mRNA, while in other embodiments the RNA is pre-mRNA pre-splice RNA. The potent ASOs according to the invention are capable of hybridizing to specific "target sequences" within the target nucleic acid.

As used herein, the term "target sequence" refers to a human CTGF mRNA sequence within the target nucleic acid that is complementary to at least an 8, 9, 10, 11, 12, 13, 14, 15, 16, 17, 18, 19 or 20 contiguous nucleotide portion of an antisense oligonucleotide disclosed herein. In some embodiments, the target sequences have perfect complementarity to an antisense oligonucleotide disclosed herein.

As used herein, the term "hypersensitive region." refers to a region of human CTGF mRNA sequence that is at least 21 nucleotides in length wherein hybridization of a complementary antisense oligonucleotide to a portion of the hypersensitive region results in at least a 50% inhibition of CTGF mRNA expression compared to vehicle-treated control. In some embodiments, the entire length of the antisense oligonucleotide is complementary to a portion of the hypersensitivity region. In other embodiments, at least a contiguous 8 nucleotide sequence of the antisense oligonucleotide is complementary to a portion of the hypersensitive region. Hypersensitive regions of the invention are found within the coding region and the 3' UTR of human CTGF mRNA SEQ ID NO: 1 and can be determined by inspection of Table 2. Additionally, the sequences of the empirically derived hypersensitive regions of human CTGF mRNA are disclosed in Table 3 along with their respective SEQ ID NOs. A hypersensitive region may overlap with one or more other hypersensitive regions.

In some embodiments, the potent antisense oligonucleotides of the inventions are complementary to a hypersensitive region from nucleotides 567 to 588, 789 to 814, 859 to 880, 946 to 988, 981 to 1002, 989 to 1010, 1006 to 1044, 1032 to 1055, 1061 to 1089, 1107 to 1145, 1132 to 1153, 1164 to 1194, 1179 to 1216, 1211 to 1232, 1236 to 1265, 1329 to 1350, 1514 to 1552, 1623 to 1656, 1651 to 1672, 1750 to 1774, 1759 to 1786, 1771 to 1808 or 1793 to 1820 of SEQ ID NO: 1.

In other embodiments, the potent antisense oligonucleotides of the invention are complementary, to a hypersensitive region from nucleotides 567 to 588, 859 to 880, 981 to 1002, 989 to 1010, 1061 to 1089, 1132 to 1153, 1179 to 1216, 1211 to 1232, 1329 to 1350, 1623 to 1656, 1651 to 1672, 1750 to 1774, 1759 to 1786, or 1793 to 1820 of SEQ ID NO: 1.

In further embodiments, the potent antisense oligonucleotides of the invention are complementary to a hypersensitive region from nucleotides 859 to 880, 981 to 1002, 989 to 1010, 1061 to 1089, 1132 to 1153, 1179 to 1216, 1211 to 1232, 1329 to 1350, 1750 to 1774, 1759 to 1786, or 1793 to 1820 of SEQ ID NO: 1.

As can be seen in Table 2, certain sub-regions of the hypersensitive regions of human CTGF mRNA when targeted by antisense oligonucleotide exhibit at least 55%, 60%, 65%, 70%, 75% or 80% inhibition of CTGF mRNA expression. For example, the hypersensitive region from nucleotide 1236 to 1265, SEQ ID NO: 332, has one sub-region that exhibits at least 65% inhibition; the sub-region from nucleotide 1238 to nucleotide 1261.

The terms "disorders" and "diseases" and "conditions" are used inclusively and refer to any condition deviating from normal.

As used herein, "CTGF-associated disorders, conditions and diseases" refer to disorders, conditions and diseases associated with abnormal, dysregulated, especially increased expression of CTGF, or disorders, conditions and diseases that are affected by CTGF in terms of their development, maintenance or progression. Abnormal expression of CTGF is associated with hyperproliferative disorders that affect individual tissues, organs or multiple organs, including, but not limited to, angiolipoma, angioleiomyoma, dermatofibromas, and cancers, including acute lymphoblastic leukemia, multiple myeloma, breast cancer, colorectal cancer, gastric cancer, gastrointestinal cancer, glioma and glioblastoma, head and neck cancer, ovarian cancer, pancreatic cancer, prostate cancer, renal cancer, rhabdomyosarcoma, desmoplasia, fibrosarcoma and metastases thereof.

CTGF-associated disorders also include fibrotic disorders that affect individual tissues, organs or multiple organs, as in the case of systemic sclerosis. Fibrotic disorders include, for example, cardiac fibrosis, including cardiac reactive fibrosis or cardiac remodeling following myocardial infarction or congestive heart failure; atherosclerosis, pulmonary fibrosis, including idiopathic pulmonary fibrosis and asthma, joint fibrosis, fibrosis associated with dialysis including peritoneal dialysis; kidney fibrosis; liver fibrosis, interstitial fibrosis, scleroderma, skin fibrosis, keloids; fibrosis resulting from acute or repetitive traumas, including surgery i.e., surgical adhesions such as abdominal and peritoneal adhesions, chemotherapy, radiation treatment, allograft rejection; or chronic and acute transplant rejection; fibrosis from hypertrophic scarring; and scarring from burns, wound healing and surgery.

Other CTGF-associated disorders include arthritis, including rheumatoid arthritis and osteoarthritis; Crohn's disease, inflammatory bowel disease; non-proliferative diabetic retinopathy, macular degeneration; nephropathies, including diabetic nephropathy, IgA-associated nephropathy, lupus kidney disease and nephropathy due to radiocontrast agents or other chemically induced renal toxicity; and conditions associated with chemical toxicity tubule destruction.

CTGF-associated disorders, conditions and diseases also refer to conditions and diseases that are associated with normal expression levels of CTGF, but the severity and progression of the condition or disease is influenced by the CTGF level. For such conditions and diseases, modulation of CTGF levels represents an intervention point for reducing the severity, or halting disease progression.

Sequences

The synthetic antisense oligonucleotides of the invention are 8 to 50 nucleotides in length and correspond to complementary nucleotide sequences present in human CTGF mRNA. In some embodiments, the antisense oligonucleotides are at least 8, 9, 10, 11, 12, 13, 14, 15, 16, 17, 18, 19, 20, 21, 22, 23, 24, 25, 26, 28, 30, 32, 34, 36, 38, 40, 42, 44, 46, or 48 nucleotides in length. In other embodiments, the antisense oligonucleotides are not more than 10, 11, 12, 13, 14, 15, 16, 17, 18, 19, 20, 21, 22, 23, 25, 26, 28, 30, 32, 34, 36, 38, 40, 42, 44, 46, 48, or 50 nucleotides in length. In further embodiments, the antisense oligonucleotides are between 8 and 40, between 8 and 30, between 8 and 24, between 8 and 20, between 10 and 40, between, 10 and 30, between 10 and 24, between 10 and 20, between 12 and 40, between 12 and 30, between 12 and 24, between 12 and 20, between 13 and 30, between 13 and 24, between 13 and 20, between 16 and 24, or between 16 and 20 nucleotides in length.

In some embodiments, the synthetic antisense oligonucleotides comprise at least a 8-mer, 9-mer, 10-mer, 11-mer, 12-mer, 13-mer, 14-mer, 15-mer of 16-mer sequence of a 20-mer sequence selected from the group consisting of SEQ ID NO: 43; SEQ ID NO: 176, SEQ ID NO: 49, SEQ ID NO: 56, SEQ ID NO: 60, SEQ ID NO: 62, SEQ ID NO: 182, SEQ ID NO: 66, SEQ ID NO: 183, SEQ ID NO: 184, SEQ ID NO: 71, SEQ ID NO: 187, SEQ ID NO: 75, SEQ ID NO: 76, SEQ ID NO: 77, SEQ ID NO: 192, SEQ ID NO: 79, SEQ ID NO: 80, SEQ ID NO: 253, SEQ ID NO: 254, SEQ ID NO: 255, SEQ ID NO: 256, SEQ ID NO: 193, SEQ ID NO: 194, SEQ ID NO: 81, SEQ ID NO: 195, SEQ ID NO: 196, SEQ ID NO: 82, SEQ ID NO: 197; SEQ ID NO: 83, SEQ ID NO: 259, SEQ ID NO: 84, SEQ ID NO: 200, SEQ ID NO: 87, SEQ ID NO: 202, SEQ ID NO: 261, SEQ ID NO: 262, SEQ ID NO: 203, SEQ ID NO: 204, SEQ ID NO: 204, SEQ ID NO: 88, SEQ ID NO: 205, SEQ ID NO: 206, SEQ ID NO: 263, SEQ ID NO: 265, SEQ ID NO: 207, SEQ ID NO: 90, SEQ ID NO: 91, SEQ ID NO: 92, SEQ ID NO: 212, SEQ ID NO: 213, SEQ ID NO: 214, SEQ ID NO: 93, SEQ ID NO: 215, SEQ ID NO: 217, SEQ ID NO: 99, SEQ ID NO: 218, SEQ ID NO: 219, SEQ ID NO: 267, SEQ ID NO: 220, SEQ ID NO: 221, SEQ ID NO: 100, SEQ ID NO: 222, SEQ ID NO: 223, SEQ ID NO: 101, SEQ ID NO: 270, SEQ ID NO: 103, SEQ ID NO: 271, SEQ ID NO: 226, SEQ ID NO: 104, SEQ ID NO: 227, SEQ ID NO: 272, SEQ ID NO: 228, SEQ ID NO: 105, SEQ ID NO: 230, SEQ ID NO: 231, SEQ ID NO: 273, SEQ ID NO: 274, SEQ ID NO: 275, SEQ ID NO: 232, SEQ TO NO: 106, SEQ ID NO: 233, SEQ ID NO: 276, SEQ ID NO: 279, SEQ ID NO: 108, SEQ ID NO: 281, SEQ ID NO: 109, SEQ ID NO: 282, SEQ ID NO: 234, SEQ ID NO: 111, SEQ ID NO: 235, SEQ ID NO: 283, SEQ ID NO: 284, SEQ ID NO: 118; SEQ ID NO: 286, SEQ ID NO: 130, SEQ ID NO: 287, SEQ ID NO: 236, SEQ ID NO: 131, SEQ ID NO: 288, SEQ ID NO: 237, SEQ ID NO: 132, SEQ ID NO: 238, SEQ ID NO: 133; SEQ ID NO: 289, SEQ ID NO: 135, SEQ ID NO: 290, SEQ ID NO: 291, SEQ ID NO: 292, SEQ ID NO: 293, SEQ ID NO: 239, SEQ ID NO: 240, SEQ ID NO: 139, SEQ ID NO: 241, SEQ ID NO: 242, SEQ ID NO: 296, SEQ ID NO: 243, SEQ ID NO: 141, SEQ ID NO: 299, SEQ ID NO: 146, SEQ ID NO: 300, SEQ ID NO: 302, SEQ ID NO: 245, SEQ ID NO: 147, SEQ ID NO: 246, SEQ ID NO: 303, SEQ ID NO: 305, SEQ ID NO: 306, SEQ ID NO: 307, SEQ ID NO: 308, SEQ ID NO: 247; SEQ ID NO: 248, SEQ ID NO: 148, SEQ ID NO: 149, SEQ ID NO: 249, SEQ ID NO: 150, SEQ ID NO: 251, SEQ ID NO: 309, SEQ ID NO: 310, SEQ ID NO: 311, SEQ ID NO: 312, SEQ ID NO: 163 and SEQ ID NO: 170.

In some embodiments, the synthetic antisense oligonucleotides comprise a 20-mer sequence selected from the group consisting of SEQ ID NO: 43, SEQ ID NO: 176, SEQ ID NO: 49, SEQ ID NO: 56, SEQ ID NO: 60, SEQ ID NO: 62, SEQ ID NO: 182, SEQ ID NO: 66, SEQ ID NO: 183, SEQ ID NO: 184, SEQ ID NO: 71, SEQ ID NO: 187, SEQ ID NO: 75; SEQ ID NO: 76, SEQ ID NO: 77, SEQ ID NO: 192, SEQ ID NO: 79, SEQ ID NO: 80, SEQ ID NO: 253, SEQ ID NO: 254, SEQ ID NO: 255, SEQ ID NO: 256, SEQ ID NO: 193, SEQ ID NO: 194, SEQ ID NO: 81, SEQ ID NO: 195, SEQ ID NO: 196, SEQ ID NO: 82; SEQ ID NO: 197, SEQ ID NO: 83, SEQ ID NO: 259, SEQ ID NO: 84, SEQ ID NO: 200, SEQ ID NO: 87, SEQ ID NO: 202, SEQ ID NO: 261, SEQ ID NO: 262, SEQ ID NO: 203, SEQ ID NO: 204, SEQ ID NO: 204, SEQ ID NO: 88, SEQ ID NO: 205, SEQ ID NO: 206, SEQ ID NO: 263, SEQ ID NO: 265, SEQ ID NO: 207, SEQ ID NO: 90, SEQ ID NO: 91, SEQ ID NO: 92, SEQ ID NO: 212, SEQ NO: 213, SEQ ID NO: 214, SEQ ID NO: 93, SEQ ID NO: 215, SEQ ID NO: 217, SEQ ID NO: 99, SEQ ID NO: 218, SEQ ID NO: 219; SEQ ID NO: 267, SEQ ID NO: 220, SEQ ID NO: 221, SEQ ID NO: 100, SEQ ID NO: 222, SEQ ID NO: 223, SEQ ID NO: 101, SEQ ID NO: 270, SEQ ID NO: 103, SEQ ID NO: 271, SEQ ID NO: 226, SEQ ID NO: 104, SEQ ID NO: 227, SEQ ID NO: 272, SEQ ID NO: 228, SEQ ID NO: 105; SEQ ID NO: 230, SEQ ID NO: 231, SEQ ID NO: 273, SEQ ID NO: 274, SEQ ID NO: 275, SEQ ID NO: 232, SEQ ID NO: 106, SEQ ID NO: 233, SEQ ID NO: 276, SEQ ID NO: 279, SEQ ID NO: 108; SEQ ID NO: 281, SEQ ID NO: 109, SEQ ID NO: 282, SEQ ID NO: 234, SEQ ID NO: 111, SEQ ID NO: 235, SEQ ID NO: 283, SEQ ID NO: 284, SEQ ID NO: 118, SEQ ID NO: 286, SEQ ID NO: 130, SEQ ID NO: 287, SEQ ID NO: 236, SEQ ID NO: 131, SEQ ID NO: 288, SEQ ID NO: 237, SEQ ID NO: 132, SEQ ID NO: 238, SEQ ID NO: 133, SEQ ID NO: 289, SEQ ID NO: 135, SEQ ID NO: 290, SEQ ID NO: 291, SEQ ID NO: 292, SEQ ID NO: 293, SEQ ID NO: 239, SEQ ID NO: 240, SEQ ID NO: 139, SEQ ID NO: 241, SEQ ID NO: 242, SEQ ID NO: 296, SEQ ID NO: 243, SEQ ID NO: 141, SEQ ID NO: 299, SEQ ID NO: 146, SEQ ID NO: 300, SEQ ID NO: 302, SEQ ID NO: 245, SEQ ID NO: 147, SEQ ID NO: 246, SEQ ID NO: 303, SEQ ID NO: 305, SEQ ID NO: 306, SEQ ID NO: 307, SEQ ID NO: 308, SEQ ID NO: 247, SEQ ID NO: 248, SEQ ID NO: 148, SEQ ID NO: 149, SEQ ID NO: 249, SEQ ID NO: 150, SEQ ID NO: 251, SEQ ID NO: 309, SEQ ID NO: 310, SEQ ID NO: 311, SEQ ID NO: 312, SEQ ID NO: 163 and SEQ ID NO: 170.

In some embodiments, the respective ends of a linear antisense oligonucleotide are joined to form a circular structure. In some embodiments, the antisense oligonucleotides consist only of a single strand. In other embodiments, the antisense oligonucleotides further comprise a double strand, wherein the second strand is complementary to at least a portion of the first strand. In some embodiments, the second oligonucleotide strand is not a guide strand or passenger strand of a siRNA construct.

In some embodiments, the antisense oligonucleotides further comprise heterologous nucleotide sequences, i.e., non-CTGF nucleotides sequences, at the 5' and/or 3' ends. In some embodiments, the heterologous nucleotide sequences comprise at least 1, 2, 3, 4, 5, 6, 7, 8, 9, 10, 11, 12 13, 14 or 15 nucleotides. When two or more heterologous, nucleotides are present, the added nucleotides may be at the 5' end (5' addition), the 3' end (3' addition), or a combination thereof.

Oligonucleotide Composition

In some embodiments of the invention, the antisense oligonucleotides comprise naturally-occurring nucleobases, sugars and covalent internucleoside linkages, i.e., those found in naturally occurring nucleic acids. In other embodiments, the antisense oligonucleotides comprise non-naturally occurring, i.e., modified nucleobases, sugars and/or covalent internucleoside linkages. In further embodiments, the antisense oligonucleotides comprise a mixture of naturally occurring and non-naturally occurring nucleobases, sugars and/or covalent internucleoside linkages. Typically, oligonucleotides comprising wholly or partially of non-naturally occurring nucleobases, sugars or covalent internucleoside linkages have improved characteristics over oligonucleotides composed wholly of naturally-occurring components. For example, oligonucleotides comprising non-natural covalent internucleoside linkages usually have increased resistance to degradation from endonucleases or exonucleases resulting in increased in vitro and in vivo half-lives compared to oligonucleotides consisting off only naturally occurring covalent internucleoside linkages. Additionally, non-naturally occurring sugars can suitably enhance the affinity of an antisense oligonucleotide for its target sequence. Alternatively, non-naturally occurring sugars may be useful in altering immune recognition of antisense oligonucleotides by pattern recognition receptors and other mechanisms, or alter other biologic pathways that may directly or indirectly affect the activity of an oligonucleotide, such as uptake, distribution, metabolism or efflux.

Non-naturally occurring covalent internucleoside linkages, i.e., modified backbones, include those linkages that retain a phosphorus atom in the backbone and alto those that do not have a phosphorus atom in the backbone. Numerous phosphorous containing modified oligonucleotide backbones are known in the art and include, for example, phosphoramidites, phosphorodiamidate morpholinos, phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, and phosphinates. In some embodiments, the modified antisense oligonucleotide backbones that are without phosphorus atoms comprise short chain alkyl or cycloalkyl internucleoside linkages, mixed heteroatom and alkyl or cycloalkyl internucleoside linkages, or one or more short chain heteroatomic or heterocyclic internucleoside linkages. See Swayze E. and Bhat B. in *Antisense Drug Technology Principles, Strategies, and Applications.* $2^{nd}$ Ed. CRC Press, Boca Rotan Fla., 2008 p. 144-182.

In further embodiments, the non-naturally occurring internucleoside linkages are uncharged and in others, the linkages are achiral. In some embodiments, the non-naturally occurring internucleoside linkages are uncharged and achiral, e.g., peptide nucleic acids (PNAs).

In some embodiments, the modified sugar moiety is a sugar other than ribose or deoxyribose. In some embodiments, the sugar is arabinose, xylulose or hexose. In some embodiments, the sugar is substituted with one of the following at the 2'-position: OH, F; O-, S-, or N-alkyl; O-, S- or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. In some embodiments, the modifications include 2'-methoxy (2'-O—CH$_3$, 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. Similar modification may also be made at other positions on an oligonucleotide, particularly the 3' position of the sugar on the 3' terminal nucleotide or in 2'-5' linked oligonucleotides and the 5' position of 5' terminal nucleotide.

In some embodiments, the modified sugar is conformationally restricted. In further embodiments, the conformation restriction is the result of the sugar possessing a bicyclic moiety. In still further embodiments, the bicyclic moiety links the 2'-oxygen and the 3' or 4'-carbon atoms. In some embodiments the linkages is a methylene (—CH$_2$-)n group bridging the 2' oxygen atom and the 4' carbon atom, wherein n is 1 or 2. This type of structural arrangement produces what are know as "locked nucleic acids" (LNAs). See Koshkin et al. *Tetrahedron,* 54, 3607-3630, 1998; and Singh et al., *Chem. Commun,* 455-456, 1998.

In some embodiments, the sugar is a sugar mimetic that is conformationally restricted resulting in a conformationally constrained monomer. In some embodiments, the sugar mimetic comprises a cyclohexyl ring that comprises one ring heteroatom and a bridge making the ring system bicyclic. See PCT/US2010/044549. In further embodiments, the antisense oligonucleotides comprise at least one nucleotide that has a bicyclic sugar moiety or is otherwise conformationally restricted.

In some embodiments, the modified sugar moiety is a sugar mimetic that comprises a morpholino ring. In further embodiments, the phosphodiester internucleoside linkage is replaced with an uncharged phosphorodiamidate linkage. See Summerton, *Antisense Nucleic Acid Drug Dev.,* 7: 187-195, 1997.

In some embodiments, both the phosphate groups and the sugar moieties are replaced with a polyamide backbone comprised of repeating N-(2-aminoethyl)-glycine units to which the nucleobases are attached via methylene carbonyl linkers. The constructs are called peptide nucleic acids (PNAs). PNAs are achiral, uncharged and because of the peptide bonds, resistant to endo- and exonucleases. See Nielsen et al., *Science,* 1991, 254, 1497-1500 and U.S. Pat. No. 5,539,082.

Antisense oligonucleotides of the invention include those comprising entirely or partially of naturally occurring nucleobases. Naturally occurring nucleobases include adenine, guanine, thymine, cytosine, uracil, 5-methylcytidine, pseudouridine, dihydrouridine, inosine, ribothymidine, 7-methylguanosine, hypoxanthine and xanthine.

Antisense oligonucleotides of the invention also include those comprising entirely or partially of modified nucleobases (semi-synthetically or synthetically derived). Modified nucleobases include 5-methylcytosine (5-me-C), 5-hydroxymethyl cytosine, hypoxanthine, 2-aminoadenine, 2-methyladenine, 6-methyladenine, 2-propyladenine, N6-adenine, N6-isopentenyladenine, 2-methylthio-N6-isopentenyladenine, 2-methylguanine, 6-methylguanine, 2-propylguanine, 1-methylguanine, 7-methylguanine, 2,2-dimethylguanine, 2-thiouracil, 2-thiothymine and 2-thiocytosine, 5-fluorouracil, 5-bromouracil, 5-chlorouracil, 5-iodouracil, dihydrouracil, 5-methyl-2-thiouracil, 4-thiouracil, 5-methyluracil, uracil-5-oxyacetic acid methylester, uracil-5-oxyacetic acid, 5-carboxymethylaminomethyl-2-thiouridine, hypoxanthine, xantine, 4-acetylcytosine, 5-(carboxyhydroxymethyl) uracil, 5-methoxycarboxymethyluracil, 5-methoxyuracil, 5-methyl-2-thiouracil, 3-(3-amino-3-N-2-carboxypropyl) uracil, 5-carboxymethylaminomethyluracil, 5-methylaminomethyluracil, 5-methoxyaminomethyl-2-thiouracil, 5-propynyl uracil and cytosine and other alkynyl derivatives of pyrimidine bases, 6-azo uracil, cytosine and thymine, 5-uracil (pseudouracil), 4-thiouracil, 8-halo-adenine, 8-amino adenine, 8-thiol adenine, 8-thioalkyl adenine, 8-hydroxy adenine, 5-halo particularly 5-bromo, 5-trifluoromethyl uracil, 3-methylcytosine, 5-methylcytosine, 5-trifluoromethyl cytosine, 7-methylguanine and 7-methyladenine, 2-F-adenine, 2-amino-adenine, 8-azaguanine and 8-azaadenine, 7-deazaguanine, 8-halo-guanine, 8-amino guanine, 8-thiol guanine, 8-thioalkyl guanine, 8-hydroxy guanine, 7-deazaadenine, 3-deazaguanine, 3-deazaadenine, beta-D-galactosylqueosine, beta-D-mannosylqueosine, inosine, 1-methylinosine, 2,6-diaminopurine and queosine. Further modified nucleobases include tricyclic pyrimidines such as phenoxazine cytidine(1H-pyrimido[5,4-b][1,4]benzoxazin-2-(3H)-one), and phenothiazine cytidine (1H-pyrimido[5,4-b][1,4]benzothiazin-2-(3H)-one. See Herdewijn P, *Antisense Nucleic Acid Drug Dev* 10, 297-310, 2000; and Sanghvi Y S, et al. *Nucleic Acids Res,* 21: 3197-3202, 1993.

In some embodiments, at least one nucleoside, i.e., a joined base and sugar, in an antisense oligonucleotide is modified, i.e., a nucleoside mimetic. In certain embodiments, the modified nucleoside comprises a tetrahydropyran nucleoside, wherein a substituted tetrahydropyran ring replaces the naturally occurring pentofuranose ring. See PCT/US2010/022759 and PCT/US2010/023397. In other embodiments, the nucleoside mimetic comprises a 5'-substituent and a 2'-substituent. See PCT/US2009/061913. In some embodiments, the nucleoside mimetic is a substituted α-L-bicyclic nucleoside. See PCT/US2009/05813. In additional embodiments, the nucleoside mimetic comprises a bicyclic sugar moiety. See PCT/US2009/039557. In further embodiments, the nucleoside mimetic comprises a bis modified bicyclic nucleoside. See PCT/US2009/066863. In certain embodiments, the nucleoside mimetic comprises a bicyclic cyclohexyl ring wherein one of the ring carbons is replaced with a heteroatom. See PCT/US2009/03373. In still further embodiments, a 3' or 5'-terminal bicyclic nucleoside is attached covalently by a neutral internucleoside linkage to the antisense oligonucleotide. See PCT/US2009/039438. In other embodiments, the nucleoside mimetic is a tricyclic nucleoside. See PCT/US2009/037686.

The aforementioned modifications may be incorporated uniformly across an entire antisense oligonucleotide, as specific regions or discrete locations within the oligonucleotide including at a single nucleotide. Incorporating these modifications can create chimeric or hybrid antisense oligonucleotides wherein two or more chemically distinct areas exist, each made up of one or more nucleotides.

Chimeric oligonucleotides typically contain at least one region that is modified to improve at least one property of the oligonucleotide compared to the unmodified oligonucleotide. Improved properties included for instance increased resistance to nuclease degradation, increased cellular uptake, increased binding affinity for a specific sequence within the target nucleic acid and/or increased inhibition of target mRNA expression. Consequently, chimeric oligonucleotides are often preferred over unmodified oligonucleotides. Chimeric oligonucleotides, include a particular subset known as "gapmers." See Monia et al, *J. Biol Chem:* 268: 14514-14522, 1993; Altman et al. *Chimia,* 50: 168-176, 1996; Seth et al. *J Med Chem* 52: 10-13, 2009; WO/US92/011339 and WO/1993/013121.

In some embodiments, the antisense oligonucleotide are gapmers that have a central "gap" region comprising 2'-deoxynucleotides flanked on both sides by "wings" composed of 2'-methoxyethyl (2'-MOE) nucleotides. In some embodiments, gapmers comprise phosphorothioate internucleoside (backbone) linkages throughout the oligonucleotide. In other embodiments, the gapmers comprise phosphorothioate linkages in the central gap and phosphodiester linkages in the wings. In some embodiments, the gapmers comprise a sequence selected from the group consisting of SEQ ID NO: 43, SEQ ID NO: 176, SEQ ID NO: 49, SEQ ID NO: 56, SEQ ID NO: 60, SEQ ID NO: 62, SEQ ID NO: 182, SEQ ID NO: 66, SEQ ID NO: 183, SEQ ID NO: 184, SEQ ID NO: 71, SEQ ID NO: 187, SEQ ID NO: 75, SEQ ID NO: 76, SEQ ID NO: 77, SEQ ID NO: 192, SEQ ID NO: 79, SEQ ID NO: 80, SEQ ID NO: 253, SEQ ID NO: 254, SEQ ID NO: 255; SEQ ID NO: 256, SEQ ID NO: 193, SEQ ID NO: 194, SEQ NO: 81, SEQ ID NO: 195, SEQ ID NO: 196, SEQ ID NO: 82, SEQ ID NO: 197, SEQ ID NO: 83, SEQ ID NO: 259; SEQ ID NO: 84, SEQ ID NO: 200, SEQ ID NO: 87, SEQ ID NO: 202; SEQ ID NO: 261, SEQ ID NO: 262, SEQ ID NO: 203, SEQ ID NO: 204, SEQ ID NO: 204, SEQ ID NO: 88, SEQ ID NO: 205; SEQ ID NO: 206, SEQ ID NO: 263, SEQ ID NO: 265, SEQ ID NO: 207, SEQ ID NO: 90, SEQ ID NO: 91, SEQ ID NO: 92, SEQ ID NO: 212, SEQ ID NO: 213, SEQ ID NO: 214, SEQ ID NO: 93, SEQ ID NO: 215, SEQ ID NO: 217, SEQ ID NO: 99, SEQ ID NO: 218, SEQ ID NO: 219; SEQ ID NO: 267, SEQ ID NO: 220, SEQ ID NO: 221, SEQ ID NO: 100; SEQ ID NO: 222, SEQ ID NO: 223, SEQ ID NO: 101, SEQ ID NO: 270; SEQ ID NO: 103, SEQ ID NO: 271, SEQ ID NO: 226; SEQ ID NO: 104, SEQ ID NO: 227, SEQ ID NO: 272, SEQ ID NO: 228, SEQ ID NO: 105, SEQ ID NO: 230, SEQ ID NO: 231, SEQ ID NO: 273, SEQ ID NO: 274, SEQ ID NO: 275, SEQ ID NO: 232, SEQ ID NO: 106, SEQ ID NO: 233, SEQ ID NO: 276, SEQ ID NO: 279, SEQ ID NO: 108, SEQ ID NO: 281, SEQ ID NO: 109, SEQ ID NO: 282; SEQ ID NO: 234, SEQ ID NO: 111, SEQ ID NO: 235, SEQ ID NO: 283; SEQ ID NO: 284, SEQ ID NO: 118; SEQ ID NO: 286, SEQ ID NO: 130, SEQ ID NO: 287, SEQ ID NO: 236, SEQ ID NO: 131, SEQ ID NO: 288, SEQ ID NO: 237, SEQ ID NO: 132, SEQ ID NO: 238, SEQ ID NO: 133, SEQ ID NO: 289, SEQ ID NO: 135, SEQ ID NO: 290, SEQ ID NO: 291, SEQ ID NO: 292, SEQ ID NO: 293, SEQ ID NO: 239, SEQ ID NO: 240, SEQ ID NO: 139, SEQ ID NO: 241, SEQ ID NO: 242, SEQ ID NO: 296, SEQ ID NO: 243, SEQ ID NO: 141, SEQ ID NO: 299, SEQ ID NO: 146, SEQ ID NO: 300, SEQ ID NO: 302, SEQ ID NO: 245, SEQ ID NO: 147, SEQ ID NO: 246, SEQ ID NO: 303, SEQ ID NO: 305, SEQ ID NO: 306, SEQ ID NO: 307, SEQ ID NO: 308, SEQ ID NO: 247, SEQ ID NO: 248, SEQ ID NO: 148, SEQ ID NO: 149, SEQ ID NO: 249, SEQ ID NO: 150, SEQ ID NO: 251, SEQ ID NO: 309, SEQ ID NO: 310, SEQ ID NO: 311, SEQ ID NO: 312, SEQ ID NO: 163 and SEQ ID NO: 170.

In other embodiments, the gapmers are complementary to a hypersensitive region selected from SEQ ID NO: 318 to SEQ ID NO: 340 (Table 3).

In further embodiments, particular gapmers are envisioned comprising (a) a gap segment comprising linked deoxynucleosides, (b) a 5' wing segment comprising linked modified nucleosides; and (c) a 3' wing segment comprising linked modified nucleosides, wherein the gap segment is positioned between the 5' wing segment and the 3' wing segment and wherein each modified nucleoside within each wing segment comprises a modified sugar. In further embodiments, the modified sugar comprises a 2'-O,4-C-methylene bridge. In still further embodiments, the gapmer comprises: (a) a gap segment comprising 5, 6, 7, 8, 9, 10, 11, 12, 13, 14, 15 or 16 linked deoxynucleosides, (b) a 5' wing segment comprising 1, 2, 3, 4, 5, 6 or 7 linked modified nucleosides; and (c) a 3' wing segment comprising 1, 2, 3, 4, 5, 6 or 7 linked modified nucleosides; wherein the gap segment is positioned between the 5' wing segment and the 3' wing segment; wherein each modified nucleoside within each wing segment comprises of a modified sugar comprising a 2'-O,4'-C-methylene bridge; and wherein each internucleoside linkage is a phosphothioate linkage. In a preferred embodiment, the antisense oligonucleotides have a 2-16-2, 3-14-3, 2-13-5 or 4-12-4, 5' wing segment-gap-3' wing segment motif. See PCT/US2009/054973.

In some embodiments, the antisense oligonucleotides further comprise a nucleotide tail, wherein the nucleotides of the tail have phosphodiester backbones or other suitable backbones to impart increased solubility to the antisense molecule, as disclosed in Toon et al. (*British J Haematology,* 96: 377-381, 1997). The use of a soluble tail can obviate the need to use liposomes, for delivery allowing the antisense molecule to be dissolved directly into a suitable aqueous medium.

In some embodiments, the antisense oligonucleotides further comprise a heterogeneous molecule covalently attached to the oligomer, with or without the use of a linker, also known as a crosslinker. In some embodiments, the heterogeneous molecule is a delivery or internalization moiety that enhances or assists the absorption, distribution and/or cellular uptake of the oligonucleotides. These moieties include polyethylene glycols, cholesterols, phospholipids, cell-penetrating peptides (CPPs), ligands to cell membrane receptors and antibodies. See Manoharan M. in *Antisense Drug Technology: Principles, Strategies and Applications*, Crooke S T, ed. Marcel Dekker, New York, N.Y., 2001, p. 391-470.

The disclosed antisense oligonucleotides may be conveniently and routinely made through the well-known technique of solid phase synthesis. Equipment for such synthesis is sold by several vendors including, for example, Life Technologies Corporation (Carlsbad, Calif.). Any other means for such synthesis known in the art may alternatively be employed. Additionally, numerous service providers can be contracted to prepare the disclosed compounds.

Applications

The antisense oligonucleotides of the invention may be utilized as research reagents including, for example, in biomedical science applications and in the development of diagnostics or therapeutics applications. In biomedical research, such antisense oligonucleotides may be used to specifically inhibit the synthesis of human CTGF protein (typically by degrading CTGF mRNA of inhibiting the transcription or translation of CTGF mRNA) in cells and experimental animals to facilitate the understanding of the role that CTGF may play under physiological or pathological conditions.

In diagnostics, the antisense oligonucleotides may be used to detect and quantitate CTGF mRNA expression in cells and tissues by northern blotting, in-situ hybridization or similar techniques. For experimental therapeutics, an animal suspected of having a CTGF-associated disease or disorder can be treated by administering antisense oligonucleotides in accordance with this invention. Monitoring the response of the animal would allow researchers to better understand the role of CTGF in disease etiology and progression. From this understanding, better diagnostic or therapeutic treatment methods including antisense oligonucleotide treatment methods can be developed.

The antisense oligonucleotides of the invention can be used therapeutically to treat CTGF-associated disorders, conditions and diseases when administered alone or formulated as pharmaceutical compositions as described below. CTGF-associated disorders include, but are not limited to, hyperproliferative disorders including angiolipoma, angioleiomyoma, dermatofibromas, and cancers, including acute lymphoblastic leukemia, multiple myeloma, breast cancer, colorectal cancer, gastric cancer, gastrointestinal cancer, glioma and glioblastoma, head and neck cancer, liver cancer, lung cancer, ovarian cancer, pancreatic cancer, prostate cancer, renal cancer, rhabdomyosarcoma, desmoplasia, fibrosarcoma and metastases thereof.

CTGF-associated disorders also include fibrotic disorders that affect individual tissues, organs or multiple organs, as in the case of systemic sclerosis. Fibrotic disorders include, for example, cardiac fibrosis, including cardiac reactive fibrosis or cardiac remodeling following myocardial infarction or congestive heart-failure; atherosclerosis, pulmonary fibrosis, including idiopathic pulmonary fibrosis and asthma; fibrosis associated with dialysis including peritoneal dialysis; kidney fibrosis; liver fibrosis; interstitial fibrosis, scleroderma; skin-fibrosis including scars; keloids; and fibrosis resulting from acute or repetitive traumas, including surgery, chemotherapy, radiation treatment; allograft rejection; or chronic and acute transplant rejection.

Other CTGF-associated disorders include arthritis, including rheumatoid arthritis and osteoarthritis; Crohn's disease; inflammatory bowel disease; non-proliferative diabetic retinopathy, macular degeneration; nephropathies, including diabetic nephropathy, IgA-associated nephropathy, lupus kidney disease and nephropathy due to radiocontrast agents or other chemically induced renal toxicity; and conditions associated with chemical toxicity tubule destruction.

In some embodiments, methods are provided for reducing hypertropic scarring resulting from dermal wound healing in a subject in need thereof. In these methods, an antisense oligonucleotide is administered in an effective amount to inhibit expression of CTGF, thereby reducing scarring from wound healing. In some embodiments, the wound healing is healing at a wound selected from the group consisting of skin breakage, surgical incisions and burns. In further embodiments, the subject is administered an antisense oligonucleotide before a surgical procedure is performed. In other embodiments, methods are provided for reducing adhesions including those from surgery. In these methods, an antisense oligonucleotide is administered in an effective amount to inhibit expression of CTGF, thereby reducing the formation of adhesions.

In further embodiments, methods are provided for treating an individual prophylactically to reduce current or expected level of CTGF expression thereby preventing, reducing, attenuating or delaying the onset or severity of a future CTGF-associated disease, condition of disorder. In some embodiments, the individual is predisposed or has an elevated risk of developing a CTGF-associated disease, condition or disorder based upon, occupational, genetic, previous medical history or other factors. In some embodiments, the previous medical history includes, but is not limited to, heart disease, diabetes, obesity or treatment with radiotherapy or chemotherapeutic agents.

Suitable routes of administration include parenteral (systemic) and loco-regional including topical administration. Parenteral administration includes oral, intravenous, intramuscular; subcutaneous, intra-arterial, intra-articular and pulmonary administration. Loco-regional administration includes intraperitoneal, retroperitoneal, intradermal, epidermal, intralesional, ocular, intraocular, intrapleural, intrathecal, intraventricular, intravesical, intranasal, vaginal, bladder and buccal administration. It is understood that appreciable systemic exposure can be achieved through loco-regional administration, if desired, through the use of appropriate formulations, administered quantities of ASOs and dosing schedules. The indication to be treated and treatment intent dictate the route of administration to be used and consequently the type of formulation.

Pharmaceutical Compositions

The present invention also includes pharmaceutical compositions and formulations that comprise the disclosed antisense oligonucleotides. One of skill in the art will recognize that the formulation employed will depend in part on the intended route of administration. Various formulations and drug delivery systems are available in the art. See, e.g., Gennaro, A. R., ed. (1990) *Remington's Pharmaceutical Sciences*, 18th ed., Mack Publishing Co., and Hardman, Limbird and Gilman, eds (2001) *The Pharmacological Basis of Therapeutics*, McGraw-Hill, New York, N.Y.

Typically, the antisense oligonucleotides are present in pharmaceutical compositions and formulations as pharmaceutically acceptable salts, i.e., salts that retain the desired biological activity of the parent compound and do not impart undesired toxicological effects thereto. Pharmaceutically acceptable salts include base addition salts that are formed with metals, for example, sodium, potassium, magnesium or calcium cations, or as organic amines, for example, chloroprocaine, choline, diethanolamine or ethylenediamine. Pharmaceutically acceptable salts also include organic or inorganic acid salts of amines, for example, hydrochlorides, acetates or phosphates. Other suitable pharmaceutically acceptable salts are well known to those skilled in the art.

Compositions and formulations for injection include sterile aqueous solutions or emulsions that may further contain buffers, diluents, carriers, preservatives, stabilizer and other excipients. Compositions and formulations for oral administration include tablets, capsules, gel capsules, dragees, powders, suspensions, emulsions, microemulsions or solutions. Typically, the compositions and formulations for oral administration further include binders, bulking agents, carriers, coloring agents, flavoring agents, surfactants, chelators, emulsifiers and other excipients. Preferred surfactants include fatty acids, esters of fatty acids, bile acids and their salts. Pharmaceutically acceptable excipients are available in the art, and include those listed in various pharmacopoeias. See, e.g., USP, JP, EP, and BP, and *Handbook of Pharmaceutical Additives*, ed. Ash; Synapse Information Resources, Inc. 2002.

Compositions and formulations for topical administration include transdermal patches, ointments, lotions, creams, gels, foams, sprays and liquids. The antisense oligonucleotides of the invention can be delivered transdermally by iontophoretic delivery, electroporation, microneedle arrays or chemical penetration enhancers including lipids and liposomes.

As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the antisense oligonucleotides. Liposomes can protect encapsulated drugs in their internal compartments from metabolism and degradation, increase drug accumulation at a target site, and reduce drug toxicity. See Lian T. and Ho, R, J. Y. *J Pharma Sci*, 90: 667-680, 2001

Lipids and liposomes include neutral lipids, e.g., dioleoylphosphatidyl ethanolamine and distearolyphosphatidyl choline; negative lipids, e.g., dimyristoylphosphatidyl glycerol and cationic lipids, e.g., dioleoylphosphatidyl ethanolamine dioleyloxypropyltrimethyl ammonium chloride.

For parenteral administration, liposomes may incorporate glycolipids or be derivatized with one or more hydrophilic polymers, such as a polyethylene glycol (PEG) to enhance circulation lifetimes relative to liposomes lacking such specialized lipids or hydrophilic polymers. See Uster P. S. et al. *FEBS Letters*, 1996, 386: 243-246. Additionally, liposomes can be targeted to specific cell types by coupling the liposome to antibodies, antibody fragments or ligands. See Yu B et al. *Am Asso Pharma Sci*, 11: 195-203, 2009

Preferred formulations for topical administration include those in which the antisense oligonucleotides of the invention are in admixture with a topical delivery agent such as lipids, liposomes, fatty acids, fatty acid esters, steroids, chelating agents and surfactants.

The compositions of the invention may be provided in an instant release, controlled release or sustained release formulation with formulation ingredients dependent on the administration route and treatment intent.

In some embodiments, pharmaceutical compositions contain two or more antisense oligonucleotides, each targeted to the same hypersensitive region of CTGF mRNA. In some embodiments, the combination of two or more antisense oligonucleotides produces at least an additive degree of inhibition of CTGF mRNA expression. In other embodiments, the combination of two or more antisense oligonucleotides produces a synergistic degree of inhibition of CTGF mRNA expression.

In other embodiments, pharmaceutical compositions contain two or more antisense oligonucleotides, each targeted to a different hypersensitive region of CTGF mRNA. In some embodiments, the combination of two or more antisense oligonucleotides produces at least an additive degree of inhibition of CTGF mRNA expression. In other embodiments, the combination of two or more antisense oligonucleotides produces a synergistic degree of inhibition of CTGF mRNA expression.

An additional benefit of administering pharmaceutical compositions containing at least two antisense oligonucleotides at a total dosage that is equivalent to an effective dosage of a single antisense oligonucleotide is that any sequence specific off-target effects caused by one particular antisense oligonucleotide will be diluted out or minimized through the use of the other antisense oligonucleotide while maintaining the desired efficacy.

In further embodiments, the pharmaceutical compositions contain at least one antisense oligonucleotide and another pharmaceutical agent that functions by a non-antisense mechanism, such as a small molecule drug, antibody or other immunotherapy agent. Examples of small molecule drugs include, but are not limited to, cancer chemotherapeutics, anti-inflammatory drugs, analgesics and anti-virals.

The antisense oligonucleotides of the invention can also be provided or administered as prodrugs. As used herein, the term "prodrug" indicates a therapeutic agent that is prepared in an active form and following administration to an animal, including humans, the prodrug is converted to the biologically active antisense oligonucleotide typically through the action of endogenous enzymes or changes in pH. In some embodiments, prodrug versions of the antisense oligonucleotides of the invention are prepared as SATE [(S-acetyl-2-thioethyl)phosphate] derivatives. See Tosquella G. et al. *Nucleic Acids Res*, 26: 2069-2074, 1998.

Antisense Oligonucleotide Dosages and Dosing Schedules

The pharmaceutical formulations of the present invention may be manufactured or dispensed into single unit or multi-unit dosage forms using techniques well known in the pharmaceutical industry. Single unit and multi-unit dosage forms, include, but are not limited to, tablets, capsules, gel capsules, tubes, suppositories, patches, vials and pre-filled syringes.

A therapeutically effective dose of an antisense oligonucleotide composition refers to an amount of antisense oligonucleotide that ameliorates or reduces the symptoms of a CTGF-associated condition. A therapeutically effective dose also includes an amount of antisense oligonucleotide that prevents the development, slows the progression or cures a CTGF-associated condition.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

Dosing is dependent on the severity of the disease and the responsiveness of the disease to therapy among other factors. In some embodiments of the invention, the antisense oligonucleotide is administered at a dose of at least about 0.001, 0.01, 0.05, 0.1, 0.5, 1, 2, 3, 4, 5, 10 or 100 mg/kg of body weight. In other embodiments, the antisense oligonucleotide is administered at a dose of no more than about 0.001, 0.01, 0.05, 0.1, 0.5, 1, 2, 3, 4, 5, 10, 50 or 100 mg/kg of body weight. Alternately, in some embodiments, the antisense oligonucleotide is administered at a dose of at least about 0.01, 0.1, 1, 10, 100 or 1000 mg/m$^2$ of body surface area (BSA). In other embodiments, the antisense oligonucleotide is administered at a dose of not more than about 1, 10, 100, 1,000 or 5,000 mg/m$^2$ of BSA. In particular embodiments, for the prevention or reduction of hypertropic scarring, the antisense oligonucleotide is administered between 1.0 µg/cm to 10 mg/cm of the wound length.

A patient can receive a single treatment or a course of treatment lasting from two or more days, weeks, months or years. Alternately, a patient can be treated until a cure is affected of a diminution of the disease state or symptoms is achieved. Following successful treatment, it may be desirable to have the patient undergo maintenance therapy to prevent the recurrence of the disease state, wherein the antisense oligonucleotide administered in maintenance doses, ranging from at least about 0.001, 0.01, 0.05, 0.1, 0.5, 1, 2, 3, 4, 5, 10, 50 or 100 mg per kg of body weight, daily, weekly, monthly or yearly as necessary.

Persons of ordinary skill can easily determine optimum dosages, dosing methodologies and repetition rates. Optimum dosage may vary depending on the relative potency of individual antisense oligonucleotides, and can generally be estimated based on an $EC_{50}$ found to be effective in an in vitro or in vivo model. Optimal dosing schedules can be calculated from measurements of drug accumulation in the body of a patient. The pharmaceutical compositions of the invention can be administered at the same time as one or more other pharmaceutical agents or at different times.

For therapeutics, a mammal, preferably a human, having a disease, condition or disorder, or at risk for developing one, is treated by modulating the expression of CTGF through administration of one or more antisense oligonucleotides in accordance with this invention. For example, in some non-limiting embodiments, the treatment method comprises the step of administering to a mammal in need thereof, a therapeutically effect amount of an antisense oligonucleotide that targets CTGF mRNA. In some embodiments, the antisense oligonucleotides are administered before the administration of another treatment modality or medical procedure, such as radiation therapy. In other embodiments, the antisense oligonucleotides are administered after an earlier treatment modality or procedure, for example, after surgery, for the prevention or reduction of scarring.

Kits

The antisense oligonucleotides and compositions of the present invention can be supplied to researchers and healthcare practitioners as kits. Typically, research kits include one or more containers holding one or more CTGF antisense oligonucleotides and instructions for using the oligonucleotides for the purpose of modulating CTGF expression. Kits for medical use typically include one or more packs or dispenser devices containing one or more unit dosage forms of the antisense oligonucleotide compositions and instructions for their administration. Such a pack or device may, for example, comprise metal or plastic foil, such as a blister pack; or plastic bottle and cap. Compositions comprising an agent of the invention formulated in a compatible pharmaceutical carrier may also be prepared, placed in an appropriate container such as a metal or plastic tube with cap and labeled for treatment of an indicated condition.

The following examples serve only to illustrate and aid in the understanding of the invention and are not intended to limit the invention as set forth in the claims which follow thereafter. Various modifications of the invention, in addition to those shown and described herein, will become apparent to those skilled in the art from the foregoing description. Such modifications are intended to fall within the scope of the appended claims. All references cited herein are hereby incorporated by references in their entirety.

EXAMPLES

Example 1

In Silico Identification of Antisense Oligonucleotides

Antisense oligonucleotides are known to inhibit gene expression. In an effort to identify novel, highly active antisense oligonucleotides to human CTGF, the entire spliced human CTGF mRNA sequence (NCBI Reference Sequence NM_001901; SEQ ID NO: 1; FIG. 1), including the 5' UTR (untranslated region) and 3'UTR, was screened in silico. To facilitate the screening process, the CTGF mRNA representing the coding sequence was divided into consecutive, 10 nucleotide sequence windows, while the 5' UTR and 3' UTR regions were divided into consecutive, 15 nucleotide sequence windows. Regions of low sequence of complexity and simple interspersed repeats were identified using RepeatMasker. 3.2.7 run on the Crossmatch search engine (AFA Smit, Institute for Systems Biology). These regions were excluded from further analysis leaving a total of 181 screening windows.

The nucleic acid sequences represented by each screening window served as the starting point for in silico hybridization with a set of either 10 complementary oligonucleotides (coding region) of 15 complementary oligonucleotides (5' UTR and 3' UTR). Each oligonucleotide in a set was 20 nucleotides in length with one portion of the oligonucleotide hybridizing by its 3' end to its complementary nucleotide sequence within the screening window and the remaining portion of the oligonucleotide hybridizing to the mRNA sequence that was immediately adjacent to the window in the 3' direction of the mRNA strand. The sequence of CTGF mRNA that is complementary to a test oligonucleotide was termed a "target sequence".

Using a coding sequence screening window that contains a sequence of 10 nucleotides as an example, the screening window will have ten, 20-mer ASOs that are each complementary to a portion of the human CTFG mRNA sequence represented by the screening window. The 3' end of these ASOs must hybridize to the CTGF mRNA beginning somewhere within the window. One ASO will hybridize to the complete 10 nucleotide screening window sequence with the remaining 10 nucleotides of the antisense oligonucleotide hybridizing to the CTGF mRNA that is contiguous to the window in the direction of the 3' end of the mRNA strand. Another antisense oligonucleotide will hybridize to 9 nucleotides in the screening window sequence and to 11 nucleotides in the CTGF mRNA that is contiguous to the window in the direction of the 3' end of the mRNA strand. And so on, until the last oligonucleotide in the series hybridizes to 1 nucleotide in the screening window and to 19 nucleotides in the CTGF mRNA that is contiguous to the window in the direction of the 3' end of the mRNA strand. In this way, a set of ten oligonucleotides was generated for every screening window representing a 10 nucleotide portion of the CTGF mRNA coding region. Each oligonucleotide in a set possesses perfect complementarity to its target sequence of CTGF mRNA. Similarly, a set of 15 complementary oligonucleotides was generated for every screening window representing the 5' UTR and 3' UTR.

Next, each 20-mer oligonucleotide within an individual screening window set was assigned a theoretical score based on the Gibbs free energies for inter- and intra-oligonucleotide and oligonucleotide-to-target base-pairing, where free energy values at 37° C. were estimated using the OligoWalk and OligoScreen, modules of RNA structure v4.6 (Mathews et al. *Proc Natl Acad Sci* USA 2004, 101:7287-92). The respective free energy Z-scores were multiplied by coefficients of correlation obtained by Matveeva et al. for the thermodynamic properties and antisense activities of 1224 phosphorothioate ASOs (Matveeva et al. *Nucleic Acids Res* 2003, 31:4989-94), and where weighted Z-scores were summed to obtain oligonucleotide-specific thermodynamic scores.

Thus, the thermodynamic score for each oligonucleotide was calculated as 10×(0.16× the Z-score for the inter-oligonucleotide dimerization free energy+0.12×the Z-score for the intra-oligonucleotide self-pairing free energy−0.24×the Z-score for the free energy of oligonucleotide-to-target mRNA duplex formation), where the Z-score for a given oligonucleotide and type of inter- or intra-molecular base-pairing was calculated as the difference between its specific Gibbs free energy value ($\Delta G37$) and mean free energy for all 2325 possible 20-mer ASOs along the CTGF mRNA sequence, divided by the standard deviation (SD) of the free energies for all possible 20-mers, i.e., z=($\Delta G37$−means)/SD. The thermodynamic scores for all 2325 possible 20-mer ASOs ranged from −9.66 to 7.63 (median=0.07, mean±SD=−0.22±2.43).

From these calculations, the oligonucleotide with the highest score (i.e., the greatest theoretical likelihood of possessing high antisense activity) was chosen from each set and was termed a "screening oligonucleotide." Discretionary allowances were made for high-scoring oligonucleotides that fell just outside a given screening window, so that some sets contributed more than one oligonucleotide to the overall collection of screening oligonucleotides, while other windows contributed no oligonucleotides. A total of 173 screening oligonucleotides were selected and they were collectively termed "Round 1 oligonucleotides." These oligonucleotides are listed in Table 1 along with their SEQ ID NOs and predicted thermodynamic scores and were later tested in cell culture (Round 1 experiments) for their ability to modulate CTGF mRNA expression. See Example 6.

Example 2

Antisense Oligonucleotides

The antisense oligonucleotides were synthesized as 20-mer phosphorothioate-linked oligodeoxyribonucleotides using standard methodology (R. Hogrefe. 2010. A short history of oligonucleotide synthesis. In: TriLink Biotechnologies Nucleic Acid Based Products and Services, pp. 103-108). In some instances, a portion or all of the cytidine residues were replaced, by 5-methyl-2'-deoxycytidine (TriLink Biotechnologies; San Diego, Calif.). Oligonucleotides were purified by reverse phase or anion exchange high-pressure liquid chromatography (HPLC) with the purity confirmed by polyacrylamide gel elecrtrophoresis, capillary electrophoresis or HPLC. Antisense oligonucleotide identities were confirmed by mass spectrometry by the manufacturer (TriLink Biotechnologies).

In Vitro mRNA Expression Studies

In vitro studies to measure the degree of antisense-mediated inhibition of human CTGF mRNA were conducted in a systematically iterative manner as outlined below. The studies were performed in three phases termed Round 1, Round 2 and Round 3. Before describing these studies, the cell lines, cell culture conditions and transfection parameters are described in Example 3. The PCR methods for quantitating mRNA expression are described in Example 4. And finally, the steps taken to limit the introduction of experimental artifacts are described in Example 5.

Round 1 (Example 6) tested the ASOs selected in silico for the highest thermodynamic rankings (Example 1) in a cell-based assay where it was discovered that these antisense oligonucleotides had a mean percent inhibition of CTGF mRNA expression that was similar to that of a negative control ASO. While these results were disappointing, it was noted that some ASOs provided a relatively high degree of inhibition of CTGF mRNA expression (at least 50% reduction) compared to vehicle-treated controls. These were designated as "potent ASOs." It was further noted that some of the target sequences that are complementary to potent ASOs appeared to be clustered together suggesting that there may be regions within the human CTGF mRNA that are hypersensitive to ASO-mediated inhibition of mRNA expression, i.e., regions where ASOs knockdown mRNA expression by at least 50%.

Round 2 (Example 8) ASOs were primarily designed based on the Round 1 results and were intended to confirm, extend and where possible, identify the limits of these hypersensitive regions of CTGF mRNA. Round 3 (Example 9) entailed the testing of ASOs to refine the size and locations of the hypersensitive regions that were identified, in the earlier two studies.

Example 3

Cell Culture and Transfection

The ability of the synthesized antisense oligonucleotides to modulate the expression of human CTGF mRNA was tested in human Hs578T breast carcinoma cells (HTB-126), human A549 lung carcinoma cells (CCL-185) and human MG63 osteosarcoma cells (CRL-1427) (American Type Culture Collection (ATCC); Manassas, Va.). The antisense oligonucleotides were also tested in mouse C2C12 myoblast cells (CRL-1772; ATCC) for the ability to modulate the expression of mouse CTGF mRNA.

A549 cells were grown in Kaighn's Modified Ham's F-12 (F-12) Medium (ATCC 30-2004, ATCC) containing 10% fetal bovine serum (FBS; HyClone, S. Logan, Utah). The other cell lines were grown in Dulbecco's Modified Eagle's Medium (DMEM) (Mediatech, Manassas, Va.) containing 4.5 g/L D-glucose, 584 mg/L L-glutamine, 110 mg/L sodium pyruvate and 10% FBS. Hs578T cells additionally received 5 μg/mL insulin, 5 μg/mL transferrin and 5 ng/mL selenium (Sigma, St. Louis, Mo.).

Cells were initially seeded into 150 $cm^2$ tissue culture flasks and once they were growing exponentially (66-70% confluent) the cells were detached with 0.05% trypsin and 0.53 mM EDTA in Hank's Balanced Salt Solution (Mediatech). The cells were then seeded into 96-well tissue culture plates at 1000 cells/well for C2C12 or 2000 cells/well for Hs578T, A549 or MG63 in 100 μL of growth media. The cells were cultured in a humidified 37° C. incubator with 5% $CO_2$ for 24 hrs, after which the culture medium was removed and replaced with 80 μL of fresh growth media containing 10% FBS.

Each well then received 20 μL of antisense oligonucleotide solution. The solutions were made by mixing antisense oligonucleotides with Lipofectamine™ 2000 (Invitrogen, Carlsbad, Calif.) or DharmaFECT® (Thermo Fisher Scientific, Lafayette, Colo.) transfection reagent in serum-free Opti-MEM® (Invitrogen) according to the transfection reagent manufacturer's instructions. Final volumes per well of transfection reagent were of 0.5 μL DharmaFECT® 4(Hs578T), 0.4 μL DharmaFECT® 1 (A549 and MG63) or 0.25 μL Lipofectamine™ 2000 (C2C12) and the final antisense oligonucleotide concentrations were 150 nM.

Cells were cultured for 18 hrs, after which the culture medium was removed and the cells washed once with 100 μL of cold (4° C.) phosphate-buffered saline (PBS). After removing the PBS, 50 μL of TaqMan® Gene Expression Cells-to-CT™ Lysis Solution containing DNase I (Applied Biosystems (ABI) Carlsbad, Calif.) was added to each well according to the manufacturer's instructions. After 5 min of incubation at room temperature, 5 μL of Cells-to-CT™ Stop Solution was added to the lysis reactions and the lysates incubated for another 2 min at room temperature. Lysates were then placed on ice for immediate mRNA expression analysis or stored at –80° C. for later analysis.

Example 4

Real-time Quantitative PGR cDNA for PGR amplification was generated by reverse transcription (RT) using 10 μL of sample lysate in a 50 μL reaction volume containing IX Cells-to-CT™ RT Buffer and IX Cells-to-CT™ RT Enzyme Mix (ABI, P/N 4366596). The RT reactions were run for 1 hr at 37° C. The enzyme was then inactivated by heating the reaction samples for 5 min at 95° C. RT products (cDNA) were diluted 1:5 in nuclease-free water, and real-time quantitative PCR (qPCR) assays were run in triplicate on a 7900HT Fast Real-Time PCR System (ABI) using SDS v2.3 and RQ Manager v1.2 software according to the manufacturer's instructions. Duplex qPCR reactions were performed in 10 μL volumes containing 4 μL of diluted cDNA, 5 μL of 2× TaqMan® Gene Expression Master Mix (ABI, P/N 4369016), 0.5 μL of primer-limited human β-actin (ACTB) VIC-MGB endogenous control probe (ABI, #4326315E), and 0.5 μL of one of three ABI TaqMan® Gene Expression Assays for human CTGF (ABI P/N HS00170014_m1, P/N HS01026927_g1 or P/N HS01026926_g1, which cross the exon4/exon5, exon3/exon4 and exon2/exon3 boundaries, respectively). For murine cell lysates, qPCR reactions were run in separate 10 μL reaction volumes containing 4.5 μL of diluted cDNA, 5 μL of 2× TaqMan® Gene Expression Master Mix, and either 0.5 μL of mouse β-actin (Actb) Endogenous Control Probe (ABI P/N 4352341E) or 0.5 μL of a TaqMan® Gene Expression Assay for mouse Ctgf (ABI P/N Mm00515790_g1). Three, technical replicates (qPCR reactions), were run for each sample (cell lysis reaction).

The murine Ctgf and Actb transcripts were assayed separately and then Actb-normalized Ctgf mRNA expression was calculated from the arithmetic difference between the median cycle threshold (CT) value for replicate Ctgf assays and the median of replicate CT values for endogenous Actb control assays for the same biologic sample (this difference being the delta CT value). No cross-interference was noted with the simultaneous (duplex) amplification of human CTGF and ACTB transcripts in the same qPCR well. This allowed for the ACTB-normalized CTGF mRNA expression to be calculated using the median of the delta CT values for each of the replicate qPCR wells, where the delta CT value for an individual reaction was calculated as the difference between the CT values for CTGF and ACTB for that specific qPCR reaction. In turn, percent inhibition for a specific sample was determined by calculating a ratio of calculated relative concentration as compared to actin in a given sample, and then comparing that value to control wells lacking antisense oligonucleotides.

Results were rejected if the median or well-specific CT values were greater than 35 cycles for CTGF (i.e., below the limit of CTGF mRNA detection), or more than 3.32 cycles greater than the median CT value for all ACTB amplification curves on that particular qPCR plate for ACTB (i.e., if the ACTB concentration was greater than 10-fold lower than the median ACTB concentration for all assays run on the same qPCR plate). All duplex assays provided CTGF, ACTB and ACTB-normalized CTGF values that were closely correlated with those obtained from assays where each target was quantitated separately (r=0.95-0.99, p<1e-6), thus indicating a lack of interference between the combined target (CTGF) and endogenous control (ACTB) assays. "Minus-RT" controls containing all RT reaction components except the 20× RT Enzyme Mix and "minus-template" controls containing all qPCR reagents but no cell lysate were consistently negative for any amplification signal due to genomic DNA or PCR product carry-over contamination.

Example 5

Avoidance of Systematic Technical Artifacts

Multiple precautions were taken to avoid the introduction of systematic study artifacts during the antisense oligonucleotide assays. To avoid systematic PCR plate position effects all antisense oligonucleotides and controls were delivered to randomly assigned distinct tissue culture wells in each experiment so that no antisense oligonucleotide was ever delivered to the same well across independent experiments. ASOs elicited similar levels of inhibition of CTGF mRNA expression (knockdown) across all experiments (r=0.48-0.86, p<1e-6 for any two Hs578T experiments), indicating that inhibition was not related to PCR plate location.

In addition, PBS vehicle control was delivered to different well positions in each experiment, and no systematic differed in baseline CTGF mRNA expression was observed within (mean CV=13%) of between (ANOVA p=0.78) any of the screening experiments. Likewise, there was excellent agreement between plates within each individual experiment (r>0.92) as determined through the use of "bridging" controls, i.e., the same control ASOs were delivered to two independent cell culture plates in the sane individual experiment. Similarly, there was excellent agreement between Rounds (r=0.86), as indicated by the use of 29 Round 1 and 25 Round 2 inter Round "bridging" ASOs in Round 3 experiments.

A systematic analysis of antisense data obtained from wells located along the periphery of a tissue culture plate versus those that came from internal wells also failed to reveal any difference relating to plate position, again consistent with the observation that the various antisense oligonucleotides exerted similar antisense effects from one experiment to another regardless of which tissue culture well they were delivered to. Thus, no systematic technical artifacts were detected.

It has been reported that ASO carryover can sometimes systematically interfere with PCR detection of transcript levels (Frier S M and Watt A T, *Basic Principles of Antisense Drug Discovery. In: Antisense Drug Technology: Principles, Strategies, and Applications* 2nd Ed., S T Crooke, ed., 2008, CRC Press New York, pp 117-141), particularly when the ASO is designed to target sequences located within the PGR amplicon. To investigate this potential artifact, multiple CTGF qPCR assays directed towards different regions of the CTGF transcript were evaluated. Excellent agreement between independent CTGF qPCR assays HS00170014_m1 and HS01026927_g1 was observed (r=0.78-0.86 for all Round 1 screening ASOs and experiments). However, the latter assay did indicate moderate but consistently greater magnitude of CTGF targeted mRNA knockdown that the former assay for selected ASOs that targeted CTGF mRNA bases 721-767 surrounding the exon3/exon4 splice site (i.e., for sequences within the HS01026927_g1 amplicon). Otherwise, these two assays were in close agreement over all other CTGF mRNA regions, including the region from bases 931-987 that overlapped the HS00170014_m1 amplicon and including all regions that demonstrated hypersensitivity to ASO-mediated inhibition as disclosed in subsequent Examples (i.e., SEQ ID NO: 318, SEQ ID NO: 319, SEQ ID NO: 320, SEQ ID NO: 321, SEQ ID NO: 322; SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, Table 3).

For the relatively small number of Round 1 oligonucleotides (11) that exhibited poor-to-modest agreement between the HS00170014_m1 and HS01026927_g1 assays, a third TaqMan® qPCR assay (HS01026926_g1) that crosses the exon2/exon3 boundary was tested and demonstrated close agreement with the HS01026927_g1 assay. All three assays were in close agreement with each other for oligonucleotides that already showed reasonable agreement between the HS00170014_m1 and HS01026927_g1 assays, including within all hypersensitive regions (vide infra).

To minimize outlier effects due to occasional differences in assay behavior, the level of β-actin-normalized CTGF mRNA inhibition provided by a given ASO in a particular Round 1 experiment was calculated as the median of the percent inhibition values for all independent qPCR assays run for that particular ASO. Given the overall uniformity of results for the three TaqMan® assays used in the Round 1 experiments, CTGF mRNA expression levels in subsequent Round 2 and Round 3 studies were determined using the HS00170014_m1 assay. The overall percent CTGF mRNA inhibition for a given antisense oligonucleotide was in turn, calculated as the median of the percent inhibition values obtained in three to ten independent Round 1, Round 2 and/or Round 3 experiments, in which that particular antisense oligonucleotide was analyzed.

Example 6

Round 1 Experiments

The 173 screening antisense oligonucleotides (20-mers) selected in silico, as described in Example 1, were synthesized as described in Example 2. The thermodynamic scores for the Round 1 ASOs ranged from −1.45 to 7.63 (median=1.65, mean±SD=1.75±1.62). These antisense oligonucleotides were predicted to produce the greatest degree of CTGF mRNA inhibition per set of antisense oligonucleotides to individual screening windows. The antisense oligonucleotides were tested in Hs578T cells for their ability to modulate expression of CTGF mRNA. Data for each antisense oligonucleotide were obtained in three independent experiments, collectively termed "Round 1 experiments" or "Round 1 studies." The calculated percent inhibition from the combined experiments for each oligonucleotides listed in Table 1.

TABLE 1

Round 1 Antisense Oligonucleotides CTGF mRNA Inhibition

| 5' Target Site | 3' Target Site | Antisense Sequence | Thermodynamic Score | Motif-based Score | % Inhibition in Round 1 | SEQ ID NO |
|---|---|---|---|---|---|---|
| 5 | 24 | ggggaagagttgttgtgtga | 2.74 | −0.2 | 18.9 | SEQ ID NO: 2 |
| 30 | 49 | gtcgcactggctgtctcctc | 4.00 | −0.2 | 21.1 | SEQ ID NO: 3 |
| 44 | 63 | agctggagggtggagtcgca | 3.51 | 0 | 37.4 | SEQ ID NO: 4 |
| 55 | 74 | ggctgccgtcgagctggagg | 2.24 | 0 | 31.9 | SEQ ID NO: 5 |
| 75 | 94 | tcggggctgtcggccgggc | 1.75 | −0.5 | 6.6 | SEQ ID NO: 6 |
| 85 | 104 | ggctgtcgtctcggggctgt | 4.19 | −0.2 | 17.0 | SEQ ID NO: 7 |
| 199 | 218 | GGCGGCGGTCATggttggca | 3.01 | 0 | −35.8 | SEQ ID NO: 8 |
| 210 | 229 | GGGCCCATACTGGCGGCGGT | 2.02 | −0.2 | −0.5 | SEQ ID NO: 9 |
| 217 | 236 | GCGGACGGGGCCCATACTGG | 1.92 | −0.4 | 21.2 | SEQ ID NO: 10 |
| 222 | 241 | GCGACGCGGACGGGGCCCAT | 1.86 | −0.2 | 42.5 | SEQ ID NO: 11 |
| 239 | 258 | CGAGGAGGACCACGAAGGCG | 1.07 | 0.3 | 14.9 | SEQ ID NO: 12 |
| 246 | 265 | CAGAGGGCGAGGAGGACCAC | 2.56 | 0.3 | 12.8 | SEQ ID NO: 13 |

TABLE 1-continued

Round 1 Antisense Oligonucleotides CTGF mRNA Inhibition

| 5' Target Site | 3' Target Site | Antisense Sequence | Thermo-dynamic Score | Motif-based Score | % Inhibition in Round 1 | SEQ ID NO |
|---|---|---|---|---|---|---|
| 253 | 272 | CCGGCTGCAGAGGGCGAGGA | 0.95 | -0.1 | 27.8 | SEQ ID NO: 14 |
| 264 | 283 | CCGACGGCCGGCCGGCTGCA | -1.14 | -0.2 | 14.8 | SEQ ID NO: 15 |
| 280 | 299 | CCCGCTGCAGTTCTGGCCGA | 3.03 | 0 | -1.3 | SEQ ID NO: 16 |
| 284 | 303 | ACGGCCCGCTGCAGTTCTGG | 2.49 | 0 | 5.8 | SEQ ID NO: 17 |
| 314 | 333 | AGCGCGGCGCCGGCTCGTCC | -0.02 | -0.1 | -33.4 | SEQ ID NO: 18 |
| 338 | 357 | GCACGAGGCTCACGCCCGCC | 1.27 | 0 | 30.2 | SEQ ID NO: 19 |
| 350 | 369 | CGCAGCCGTCCAGCACGAGG | 3.07 | 0 | 3.8 | SEQ ID NO: 20 |
| 354 | 373 | CAGCCGCAGCCGTCCAGCAC | 4.88 | 0 | 17.0 | SEQ ID NO: 21 |
| 357 | 376 | CAGCAGCCGCAGCCGTCCAG | 4.15 | 0 | -2.5 | SEQ ID NO: 22 |
| 358 | 377 | GCAGCAGCCGCAGCCGTCCA | 4.29 | 0 | 6.4 | SEQ ID NO: 23 |
| 370 | 389 | GGCGCAGACGCGGCAGCAGC | -0.01 | 0 | 38.2 | SEQ ID NO: 24 |
| 381 | 400 | CCCAGCTGCTTGGCGCAGAC | 0.78 | 0 | 48.1 | SEQ ID NO: 25 |
| 387 | 406 | AGCTCGCCCAGCTGCTTGGC | 0.97 | 0 | 31.1 | SEQ ID NO: 26 |
| 397 | 416 | CTCGGTGCACAGCTCGCCCA | 2.76 | 0 | 42.5 | SEQ ID NO: 27 |
| 409 | 428 | GCATGGGTCGCGCTCGGTGC | 3.15 | 0 | -134.3 | SEQ ID NO: 28 |
| 415 | 434 | CGGGTCGCATGGGTCGCGCT | 2.59 | 0 | 45.8 | SEQ ID NO: 29 |
| 430 | 449 | GAAGAGGCCCTTGTGCGGGT | 1.95 | 0 | 31.0 | SEQ ID NO: 30 |
| 436 | 455 | GTCACAGAAGAGGCCCTTGT | 1.32 | 0 | 34.9 | SEQ ID NO: 31 |
| 447 | 466 | GGGGAGCCGAAGTCACAGAA | 2.24 | -0.2 | 16.4 | SEQ ID NO: 32 |
| 460 | 479 | CTTGCGGTTGGCCGGGGAGC | 1.57 | -0.3 | -64.2 | SEQ ID NO: 33 |
| 467 | 486 | CGCCGATCTTGCGGTTGGCC | 1.65 | 0 | 9.8 | SEQ ID NO: 34 |
| 475 | 494 | GGTGCACACGCCGATCTTGC | 0.80 | 0 | 6.4 | SEQ ID NO: 35 |
| 486 | 505 | CCATCTTTGGCGGTGCACAC | 0.81 | 0 | 25.7 | SEQ ID NO: 36 |
| 496 | 515 | GCAGGGAGCACCATCTTTGG | 1.65 | 0 | 20.8 | SEQ ID NO: 37 |
| 507 | 526 | CCACCGAAGATGCAGGGAGC | 2.37 | 0.3 | 35.3 | SEQ ID NO: 38 |
| 514 | 533 | CACCGTACCACCGAAGATGC | 3.11 | 0.3 | 23.9 | SEQ ID NO: 39 |
| 528 | 547 | TCTCCGCTGCGGTACACCGT | 0.05 | 0 | 7.4 | SEQ ID NO: 40 |
| 537 | 556 | TGGAAGGACTCTCCGCTGCG | 0.88 | 0.3 | 36.2 | SEQ ID NO: 41 |
| 554 | 573 | GGTACTTGCAGCTGCTCTG | -0.77 | 0.1 | 38.1 | SEQ ID NO: 42 |
| 567 | 586 | AGGCACGTGCACTGGTACTT | -0.63 | -0.2 | 61.9 | SEQ ID NO: 43 |
| 580 | 599 | CACCGCCCCGTCCAGGCACG | 4.09 | 0 | 16.3 | SEQ ID NO: 44 |
| 584 | 603 | AGCCCACCGCCCCGTCCAGG | 7.63 | 0.3 | 16.2 | SEQ ID NO: 45 |
| 589 | 608 | CATGCAGCCCACCGCCCCGT | 6.20 | 0.3 | 23.9 | SEQ ID NO: 46 |
| 600 | 619 | CTGCACAGGGGCATGCAGCC | -0.19 | -0.2 | 19.7 | SEQ ID NO: 47 |
| 608 | 627 | CGTCCATGCTGCACAGGGGC | 1.14 | -0.2 | 0.2 | SEQ ID NO: 48 |
| 613 | 632 | ACGAACGTCCATGCTGCACA | 1.29 | 0 | 56.6 | SEQ ID NO: 49 |
| 629 | 648 | AGTCAGGGCTGGGCAGACGA | 2.95 | 0 | 33.7 | SEQ ID NO: 50 |

TABLE 1-continued

Round 1 Antisense Oligonucleotides CTGF mRNA Inhibition

| 5' Target Site | 3' Target Site | Antisense Sequence | Thermo-dynamic Score | Motif-based Score | % Inhibition in Round 1 | SEQ ID NO |
|---|---|---|---|---|---|---|
| 639 | 658 | GGGAAGGGGCAGTCAGGGCT | 4.31 | -0.2 | 13.4 | SEQ ID NO: 51 |
| 646 | 665 | CCTCCTCGGGAAGGGGCAGT | 2.39 | -0.2 | 3.2 | SEQ ID NO: 52 |
| 657 | 676 | GGCAGCTTGACCCTCCTCGG | 4.57 | 0 | 29.0 | SEQ ID NO: 53 |
| 661 | 680 | CCCGGGCAGCTTGACCCTCC | 2.82 | -0.1 | 44.7 | SEQ ID NO: 54 |
| 677 | 696 | ACTCCTCGCAGCATTTCCCG | 3.92 | 0.5 | 29.6 | SEQ ID NO: 55 |
| 684 | 703 | CACACCCACTCCTCGCAGCA | 4.36 | 0.5 | 51.1 | SEQ ID NO: 56 |
| 688 | 707 | GTCACACACCCACTCCTCGC | 4.85 | 0.5 | 17.8 | SEQ ID NO: 57 |
| 692 | 711 | GCTCGTCACACACCCACTCC | 4.70 | 0.5 | 44.3 | SEQ ID NO: 58 |
| 710 | 729 | CCACGGTTTGGTCCTTGGGC | -1.42 | 0.3 | 34.5 | SEQ ID NO: 59 |
| 721 | 740 | GGCAGGCCCAACCACCGTTT | 3.08 | 0.3 | 65.8 | SEQ ID NO: 60 |
| 737 | 756 | GTCGGTAAGCCGCGAGGGCA | -0.70 | -0.2 | 28.5 | SEQ ID NO: 61 |
| 747 | 766 | GTGTCTTCCAGTCGGTAAGC | 2.23 | -0.2 | 68.9 | SEQ ID NO: 62 |
| 754 | 773 | GCCAAACGTGTCTTCCAGTC | 2.37 | 0.1 | 31.4 | SEQ ID NO: 63 |
| 762 | 781 | GGGTCTGGGCCAAACGTGTC | 1.19 | 0.1 | 12.5 | SEQ ID NO: 64 |
| 772 | 791 | AATCATAGTTGGGTCTGGGC | 2.08 | 0 | 33.2 | SEQ ID NO: 65 |
| 791 | 810 | GGACCAGGCAGTTGGCTCTA | 2.08 | 0.1 | 74.8 | SEQ ID NO: 66 |
| 809 | 828 | CGCTCCACTCTGTGGTCTGG | 0.69 | 0.6 | 27.2 | SEQ ID NO: 67 |
| 817 | 836 | GGAACAGGCGCTCCACTCTG | 1.47 | 0.6 | 47.7 | SEQ ID NO: 68 |
| 836 | 855 | TGCCCATCCCACAGGTCTTG | 4.44 | 0.6 | 9.1 | SEQ ID NO: 69 |
| 841 | 860 | GGAGATGCCCATCCCACAGG | 2.28 | 0.6 | 36.8 | SEQ ID NO: 70 |
| 859 | 878 | GTCATTGGTAACCCGGGTGG | 0.06 | -0.3 | 78.5 | SEQ ID NO: 71 |
| 865 | 884 | GGCGTTGTCATTGGTAACCC | 2.49 | -0.2 | 44.0 | SEQ ID NO: 72 |
| 870 | 889 | CAGGAGGCGTTGTCATTGGT | 2.95 | 0 | 29.4 | SEQ ID NO: 73 |
| 889 | 908 | GCTCTGCTTCTCTAGCCTGC | 3.00 | 0.2 | 13.8 | SEQ ID NO: 74 |
| 893 | 912 | GGCGGCTCTGCTTCTCTAGC | 2.06 | 0.2 | 51.6 | SEQ ID NO: 75 |
| 904 | 923 | GACCATGCACAGGCGGCTCT | 1.87 | 0.1 | 50.4 | SEQ ID NO: 76 |
| 912 | 931 | CAAGGCCTGACCATGCACAG | 0.91 | 0 | 75.6 | SEQ ID NO: 77 |
| 931 | 950 | CTCTTCCAGGTCAGCTTCGC | 3.50 | 0.1 | 25.0 | SEQ ID NO: 78 |
| 935 | 954 | TGTTCTCTTCCAGGTCAGCT | 3.02 | 0.1 | 51.6 | SEQ ID NO: 79 |
| 946 | 965 | GCCCTTCTTAATGTTCTCTT | 2.91 | -0.1 | 26.9 | SEQ ID NO: 80 |
| 960 | 979 | CGGATGCACTTTTTGCCCTT | 1.76 | 0 | 74.7 | SEQ ID NO: 81 |
| 967 | 986 | GGGAGTACGGATGCACTTTT | 1.49 | 0 | 75.2 | SEQ ID NO: 82 |
| 981 | 1000 | GGCTTGGAGATTTTGGGAGT | 2.49 | 0 | 58.2 | SEQ ID NO: 83 |
| 989 | 1008 | ACTTGATAGGCTTGGAGATT | 0.82 | 0 | 64.1 | SEQ ID NO: 84 |
| 995 | 1014 | GCTCAAACTTGATAGGCTTG | 0.22 | -0.1 | 38.7 | SEQ ID NO: 85 |
| 1003 | 1022 | GCCAGAAAGCTCAAACTTGA | 0.59 | 0 | 38.1 | SEQ ID NO: 86 |
| 1006 | 1025 | GCAGCCAGAAAGCTCAAACT | 1.14 | 0 | 62.4 | SEQ ID NO: 87 |

TABLE 1-continued

Round 1 Antisense Oligonucleotides CTGF mRNA Inhibition

| 5' Target Site | 3' Target Site | Antisense Sequence | Thermo-dynamic Score | Motif-based Score | % Inhibition in Round 1 | SEQ ID NO |
|---|---|---|---|---|---|---|
| 1019 | 1038 | TCTTCATGCTGGTGCAGCCA | 0.31 | 0.2 | 72.6 | SEQ ID NO: 88 |
| 1029 | 1048 | GCTCGGTATGTCTTCATGCT | 1.02 | 0 | 47.0 | SEQ ID NO: 89 |
| 1036 | 1055 | GAATTTAGCTCGGTATGTCT | 0.79 | 0 | 65.1 | SEQ ID NO: 90 |
| 1043 | 1062 | CTCCACAGAATTTAGCTCGG | 1.39 | 0.3 | 65.9 | SEQ ID NO: 91 |
| 1057 | 1076 | GCCGTCGGTACATACTCCAC | 1.98 | 0.5 | 66.2 | SEQ ID NO: 92 |
| 1068 | 1087 | GTGCAGCATCGGCCGTCGGT | 1.76 | 0 | 74.4 | SEQ ID NO: 93 |
| 1071 | 1090 | GGGGTGCAGCATCGGCCGTC | 1.63 | -0.2 | 49.3 | SEQ ID NO: 94 |
| 1074 | 1093 | TGGGGGGTGCAGCATCGGCC | 3.13 | -0.2 | 37.1 | SEQ ID NO: 95 |
| 1081 | 1100 | GGTTCTGTGGGGGGTGCAGC | 3.43 | -0.2 | 22.3 | SEQ ID NO: 96 |
| 1088 | 1107 | GGGTGGTGGTTCTGTGGGGG | 5.27 | -0.2 | -11.4 | SEQ ID NO: 97 |
| 1093 | 1112 | CGGCAGGGTGGTGGTTCTGT | 3.57 | 0 | 42.0 | SEQ ID NO: 98 |
| 1109 | 1128 | GGCACTTGAACTCCACCGGC | 2.67 | 0.4 | 80.4 | SEQ ID NO: 99 |
| 1122 | 1141 | ACCTCGCCGTCAGGGCACTT | 0.64 | 0 | 68.2 | SEQ ID NO: 100 |
| 1132 | 1151 | CTTCTTCATGACCTCGCCGT | 2.68 | 0 | 59.8 | SEQ ID NO: 101 |
| 1142 | 1161 | ACATCATGTTCTTCTTCATG | -0.66 | 0 | -4.2 | SEQ ID NO: 102 |
| 1159 | 1178 | GGCACAGGTCTTGATGAACA | -1.18 | 0 | 64.4 | SEQ ID NO: 103 |
| 1168 | 1187 | GTAATGGCAGGCACAGGTCT | 1.84 | -0.2 | 66.4 | SEQ ID NO: 104 |
| 1179 | 1198 | CCGGGACAGTTGTAATGGCA | 1.87 | -0.3 | 77.9 | SEQ ID NO: 105 |
| 1193 | 1212 | AGATGTCATTGTCTCCGGGA | 1.57 | -0.1 | 69.4 | SEQ ID NO: 106 |
| 1205 | 1224 | ACAGCGATTCAAAGATGTCA | 0.59 | -0.1 | 31.9 | SEQ ID NO: 107 |
| 1211 | 1230 | TGTAGTACAGCGATTCAAAG | -0.95 | -0.1 | 58.5 | SEQ ID NO: 108 |
| 1228 | 1247 | GTCTCCGTACATCTTCCTGT | 2.91 | 0 | 27.3 | SEQ ID NO: 109 |
| 1233 | 1252 | GCCATGTCTCCGTACATCTT | 2.69 | 0.2 | 40.0 | SEQ ID NO: 110 |
| 1240 | 1259 | gctTCATGCCATGTCTCCGT | 2.79 | 0.2 | 68.1 | SEQ ID NO: 111 |
| 1249 | 1268 | cactctctggctTCATGCCA | -0.79 | 0.5 | 36.3 | SEQ ID NO: 112 |
| 1255 | 1274 | gtctctcactctctggctTC | 3.34 | 0.4 | 46.7 | SEQ ID NO: 113 |
| 1261 | 1280 | gttaatgtctctcactctct | 1.40 | 0.2 | 42.5 | SEQ ID NO: 114 |
| 1286 | 1305 | atcagttcaagttccagtct | 2.49 | 0 | 33.7 | SEQ ID NO: 115 |
| 1305 | 1324 | acggaaaaatgagatgtgaa | -1.03 | -0.1 | 17.3 | SEQ ID NO: 116 |
| 1320 | 1339 | actgaaatcatttttacgga | -0.85 | -0.3 | -0.7 | SEQ ID NO: 117 |
| 1329 | 1348 | acttgtgctactgaaatcat | 0.42 | -0.3 | 58.3 | SEQ ID NO: 118 |
| 1357 | 1376 | cccccagttagaaaaacaga | 1.26 | -0.1 | 25.1 | SEQ ID NO: 119 |
| 1366 | 1385 | gaatcttttcccccagttag | 3.10 | 0.3 | 47.1 | SEQ ID NO: 120 |
| 1384 | 1403 | atgttttgaattgggtggga | 1.41 | 0 | 5.5 | SEQ ID NO: 121 |
| 1405 | 1424 | ctatttgtttgacatggcac | -0.70 | 0 | 43.0 | SEQ ID NO: 122 |
| 1417 | 1436 | ggggttgatagactattgt | 0.41 | -0.2 | 9.9 | SEQ ID NO: 123 |
| 1425 | 1444 | cagtgtctggggttgataga | 2.10 | -0.2 | 43.3 | SEQ ID NO: 124 |

TABLE 1-continued

Round 1 Antisense Oligonucleotides CTGF mRNA Inhibition

| 5' Target Site | 3' Target Site | Antisense Sequence | Thermo-dynamic Score | Motif-based Score | % Inhibition in Round 1 | SEQ ID NO |
|---|---|---|---|---|---|---|
| 1437 | 1456 | cattcttcaaaccagtgtct | 1.31 | -0.1 | 14.0 | SEQ ID NO: 125 |
| 1455 | 1474 | tccactgtcaagtcttaaca | 0.90 | -0.1 | 23.7 | SEQ ID NO: 126 |
| 1460 | 1479 | gtagttccactgtcaagtct | 2.33 | 0.1 | 49.7 | SEQ ID NO: 127 |
| 1483 | 1502 | acattctggtgctgtgtact | 1.93 | 0 | 48.4 | SEQ ID NO: 128 |
| 1498 | 1517 | gccacaccttaatatacatt | 1.48 | 0.3 | 48.2 | SEQ ID NO: 129 |
| 1514 | 1533 | tcccactgctcctaaagcca | 2.95 | 0.3 | 27.9 | SEQ ID NO: 130 |
| 1520 | 1539 | gtaccctcccactgctccta | 5.23 | 0.4 | 64.5 | SEQ ID NO: 131 |
| 1527 | 1546 | tctgctggtaccctcccact | 3.49 | 0.6 | 64.4 | SEQ ID NO: 132 |
| 1531 | 1550 | cctttctgctggtaccctcc | 3.21 | 0 | 59.4 | SEQ ID NO: 133 |
| 1549 | 1568 | gctatctgatgatactaacc | -0.20 | -0.2 | 46.0 | SEQ ID NO: 134 |
| 1574 | 1593 | agcaggcatattactcgtat | 1.21 | 0.2 | 52.0 | SEQ ID NO: 135 |
| 1585 | 1604 | acacttcaaatagcaggcat | 0.73 | -0.1 | 41.0 | SEQ ID NO: 136 |
| 1597 | 1616 | tccttctcaattacacttca | 1.48 | 0 | 14.9 | SEQ ID NO: 137 |
| 1620 | 1639 | ggtcagtgagcacgctaaaa | 0.42 | -0.3 | 40.3 | SEQ ID NO: 138 |
| 1633 | 1652 | ggggctacaggcaggtcagt | 3.32 | -0.2 | 72.2 | SEQ ID NO: 139 |
| 1647 | 1666 | tcctagctgtcactggggct | 2.88 | -0.4 | 48.3 | SEQ ID NO: 140 |
| 1653 | 1672 | tgcacatcctagctgtcact | 2.47 | 0 | 60.4 | SEQ ID NO: 141 |
| 1670 | 1689 | tcttgatggctggagaatgc | 1.89 | 0 | 49.3 | SEQ ID NO: 142 |
| 1681 | 1700 | ttgactcagtctcttgatgg | 0.07 | 0.3 | 10.1 | SEQ ID NO: 143 |
| 1712 | 1731 | ctgagtctgctgttctgact | 0.98 | 0 | 30.9 | SEQ ID NO: 144 |
| 1740 | 1759 | cagtgtcattcgaatcagaa | -1.15 | 0 | 37.4 | SEQ ID NO: 145 |
| 1752 | 1771 | ccgattcctgaacagtgtca | 1.44 | 0 | 59.5 | SEQ ID NO: 146 |
| 1763 | 1782 | tcgacaggattccgattcct | 0.96 | 0 | 62.8 | SEQ ID NO: 147 |
| 1783 | 1802 | ccacaagctgtccagtctaa | 1.85 | 0.1 | 68.4 | SEQ ID NO: 148 |
| 1785 | 1804 | tgccacaagctgtccagtct | 2.76 | 0.5 | 74.8 | SEQ ID NO: 149 |
| 1789 | 1808 | cacttgccacaagctgtcca | 1.22 | 0.5 | 70.4 | SEQ ID NO: 150 |
| 1803 | 1822 | gttacaggcaaattcacttg | 0.62 | -0.1 | 20.3 | SEQ ID NO: 151 |
| 1892 | 1911 | attaacttagtataactgtac | -1.45 | -0.6 | -3.3 | SEQ ID NO: 152 |
| 1909 | 1928 | ggcacaaacaagtttaaatt | -1.08 | -0.4 | 26.9 | SEQ ID NO: 153 |
| 1962 | 1981 | cagaaattgaggctaacatt | -0.77 | -0.3 | 16.6 | SEQ ID NO: 154 |
| 1980 | 1999 | cattctacctatggtgttca | 1.13 | 0 | 41.8 | SEQ ID NO: 155 |
| 1986 | 2005 | gctttacattctacctatgg | 1.64 | 0 | 23.7 | SEQ ID NO: 156 |
| 1998 | 2017 | acgatcagacaagctttaca | -0.32 | 0 | 34.5 | SEQ ID NO: 157 |
| 2018 | 2037 | gtatccatttcatgctttga | 1.17 | 0 | 33.6 | SEQ ID NO: 158 |
| 2026 | 2045 | ccatataagtatccatttca | 0.99 | -0.2 | 22.0 | SEQ ID NO: 159 |
| 2052 | 2071 | actgtcattctatctgagca | 1.43 | -0.2 | 33.3 | SEQ ID NO: 160 |
| 2056 | 2075 | acggactgtcattctatctg | 0.18 | -0.2 | 18.8 | SEQ ID NO: 161 |

TABLE 1-continued

Round 1 Antisense Oligonucleotides CTGF mRNA Inhibition

| 5' Target Site | 3' Target Site | Antisense Sequence | Thermo-dynamic Score | Motif-based Score | % Inhibition in Round 1 | SEQ ID NO |
|---|---|---|---|---|---|---|
| 2086 | 2105 | atgcctcccctttgcaaaca | 0.12 | 0.2 | 26.5 | SEQ ID NO: 162 |
| 2091 | 2110 | cactgatgcctcccctttgc | _4.85_ | 0.1 | _53.8_ | SEQ ID NO: 163 |
| 2115 | 2134 | acctagaaatcagcctgcca | 2.54 | 0.1 | 36.0 | SEQ ID NO: 164 |
| 2131 | 2150 | ggctaccacatttcctacct | 3.62 | 0.3 | 32.6 | SEQ ID NO: 165 |
| 2153 | 2172 | gccatttgttcattaaaagt | 0.53 | −0.1 | 11.1 | SEQ ID NO: 166 |
| 2175 | 2194 | agtcactcagttttaataa | −0.20 | −0.2 | 19.4 | SEQ ID NO: 167 |
| 2184 | 2203 | gctatatagagtcactcagt | −0.35 | 0.2 | 22.1 | SEQ ID NO: 168 |
| 2208 | 2227 | gcttccaggtgaaaaaactg | 0.54 | −0.4 | 22.8 | SEQ ID NO: 169 |
| 2215 | 2234 | aacaaatgcttccaggtgaa | 0.74 | −0.1 | _55.8_ | SEQ ID NO: 170 |
| 2221 | 2240 | agtagaaacaaatgcttcca | 0.07 | −0.2 | 5.6 | SEQ ID NO: 171 |
| 2243 | 2262 | gtccgaaaaacagtcatatc | 0.47 | −0.1 | 43.4 | SEQ ID NO: 172 |
| 2258 | 2277 | ctcaacaaataaactgtccg | −0.04 | −0.6 | 39.2 | SEQ ID NO: 173 |
| 2311 | 2330 | atacactttattttcaacta | 0.10 | 0 | 31.0 | SEQ ID NO: 174 |

Table 1. Thermodynamic and motif-base scores for 173 Round 1 screening oligonucleotides and their median % inhibition of CTGF mRNA expression vs. vehicle-treated controls from three combined experiments. To highlight the lack of an association between the predicted and empirical outcomes, thermodynamic scores ≥4 (i.e., those that should have forecast the greatest level of antisense activity) are underlined and bolded, as are inhibition values ≥50%. The 5' and 3' target sites denote the 5'-most and 3'-most complementary (sense) bases of the spliced human CTGF mRNA sequence, SEQ ID NO: 1, for the 20-nucleotide-long-ASOs. An "m" suffix denotes an oligonucleotide that crosses an exon-exon boundary and that is thus only complementary to the spliced mRNA. All other ASOs are complementary to both the spliced mRNA and non-spliced pre-mRNA.

Surprisingly, despite the careful selection based on calculated thermodynamic properties, the Round 1 antisense oligonucleotides produced mean and median percent inhibitions of human CTGF mRNA expression of 34.1%, and 34.5%, respectively, that were equivalent to that produced by a negative control antisense oligonucleotide to the gene phosphatase and tensin homolog (PTEN). A shift in the mean and median percent inhibition above that produced by the negative control, i.e., above 34%, was expected for this group as they were selected out of 2325 ASOs based on favorable thermodynamic characteristics that correlate with hybridization. These results suggested that the degree of inhibition of CTGF mRNA expression produced by the selected ASOs were non-specific and that the thermodynamic-based selection algorithm could not identify antisense oligonucleotides that had a high degree of inhibitory activity.

The failure of the calculated thermodynamic scores to predict antisense oligonucleotide sequences with high inhibitory activity is exemplified by the absence of a correlation between the predicted scores and observed outcomes ($r=-0.04$). For example, 17 of the Round 1 ASOs had a calculated thermodynamic score of at least 4 and were therefore over 1 standard deviation above the mean for the entire set of Round 1 ASOs. These ASOs were thus predicted to possess the strongest inhibitory activity (Table 1). Surprisingly, only three of these 17 ASOs (SEQ ID NO: 56, SEQ ID NO: 131, and SEQ ID NO: 163) inhibited CTGF mRNA-expression by at least 5.0% in the Round 1 studies. Conversely, another 14 Round 1 ASOs with otherwise exemplary thermodynamic scores provided only 16±4 percent mRNA inhibition, (mean±SE). Thus, in terms of forecasting which ASOs would provide at least 50% inhibition of CTGF mRNA expression, a thermodynamic cut-off score of 4 had a positive predictive value of only 18% and a false discovery rate of 82%. Indeed, the area under the receiver operating characteristic (ROC) curve describing the ability of the thermodynamic score to identify ASOs that provide at least 50% CTGF mRNA knockdown was 0.52, thus indicating that the thermodynamic score had no predictive utility ($p=0.69$).

A further observation that exemplifies the lack of predictive power of the thermodynamic score to identify ASOs with high inhibitory activity is that none of the 22 Round 1 ASOs exhibiting the highest inhibitory activity (at least 65% mRNA inhibition) were predicted to have such high activity. Instead, of the thermodynamic scores for these ASOs ranked 26th to 147th among the 173 Round 1 ASOs (median rank=81.5), falling into no clear pattern. Likewise, adjusting the ROC curve calculations to examine the ability of thermodynamic score to identify ASOs that provide at least 65% CTGF mRNA knockdown also revealed that the thermodynamic score was not predictive ($p=0.85$).

Given the failure of the thermodynamic algorithm to predict for antisense oligonucleotide activity, other parameters were evaluated to examine whether they correlated with the observed antisense activity of individual ASOs. No correlations were found between the observed level of CTGF mRNA inhibition and the calculated intra-oligonucleotide, inter-oligonucleotide or oligonucleotide-to-target free energy values ($r=0.07-0.14$). Additionally, a correlation coefficient-weighted score based on the presence of sequence motifs previously associated with antisense activity (Matveeva et al. *Nucleic Acids Res* 2000 28:2862-5) was compared with the observed percent inhibition data. This motif-based score was calculated using the following equation: motif-based score=

(0.3×the number of CCAC motifs+0.3×the number of TCCC motifs+0.2×the number of ACTC motifs+0.2×the number of GCCA motifs+0.1×the number of CTCT motifs)−(0.2×the number of GGGG motifs−0.2×the number of ACTG motifs−0.2×the number of TAA motifs−0.1×the number of CCGG motifs−0.1×the number of AAA motifs) in a given ASO. Like the thermodynamic score and component free energy values, this motif-based score was not associated with the level of antisense activity observed in the Round 1 studies (Spearman r=0.22), Table 1. The motif-based score was also a rather weak predictor of ASOs that caused at least 50% CTGF mRNA knockdown, since the area under the ROC curve describing its ability to do so (0.60) was not substantially different from the area under the diagonal line of no discrimination Likewise a TCCC sequence motif was only present in 3 (7%) of the 44 ASOs that provided at least 50% inhibition, even though it had been identified in 48% of the most potent ASOs reported at one point in the literature and 59% of ASOs containing this motif were active in a prospective study aimed at validating its predictive utility (Tu et al. *J Biol Chem* 1998 273:25125-31).

Example 7

Figure 3:
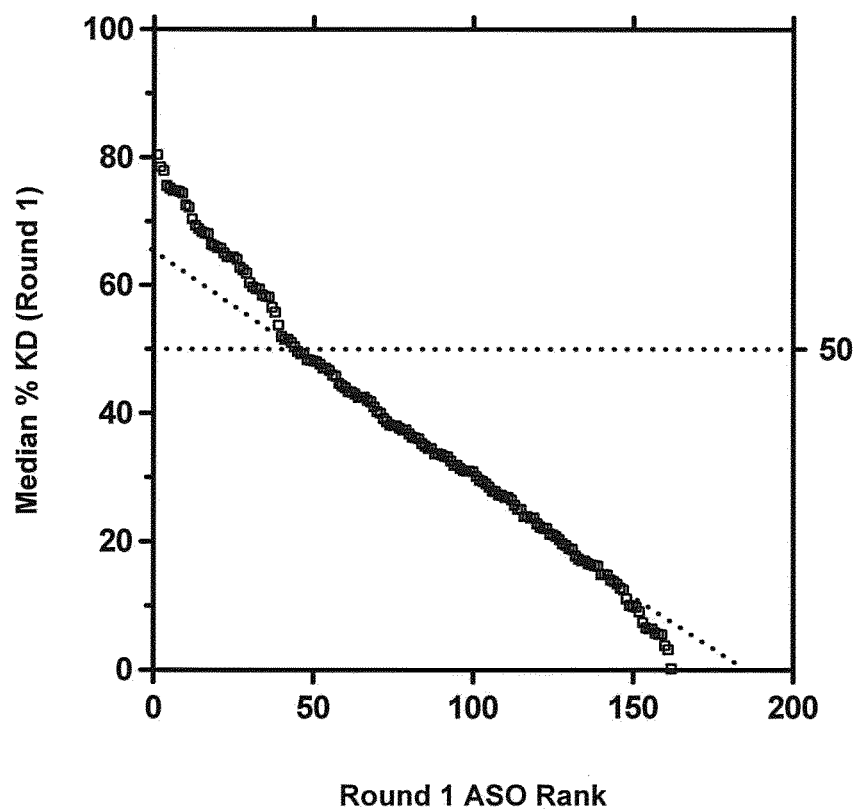
FIG. 3 is a graph of the Round 1 antisense oligonucleotides arranged as the percent inhibition of CTGF mRNA expression induced by an individual antisense oligonucleotide (y-axis) versus its respective ranking (x-axis) for CTGF mRNA inhibitory activity. An inflection point is apparent at approximately 50% inhibition that indicates a larger than expected population of potent oligonucleotides.

Non-random Distribution of Potent Sequences with Respect to Location on the CTGF mRNA Notably, rather than exhibiting a normal (Gaussian) distribution about a single mean, the Round 1 data appeared to resemble a bi-phasic distribution, as illustrated by a histogram of the inhibitory activity of Round 1 ASOs (FIG. 2). Here, a clear shoulder can be seen to the right side of an otherwise broad bell-shaped distribution that suggested the presence of a sub-population of ASOs with strong inhibitor activity. This suggestion was supported by a data inflection point at approximately 50% inhibition shown on a plot of percent inhibition versus rank for the Round 1 ASOs (FIG. 3). Based on this graph, antisense oligonucleotides that produced at least 50% inhibition of human CTGF mRNA expression were defined as "potent" antisense oligonucleotides.

Furthermore, as can be seen in Table 1, the potent ASOs (i.e., those that caused at least 50% CTGF mRNA inhibition in Round 1) were not randomly distributed in terms of the locations of their complementary target sequences along the CTGF mRNA. Instead, from these Round 1 results, several clusters of sequences that are complementary to potent ASOs appear to be present, suggestive of contiguous local regions (i.e., beyond 20 nucleotides in length) of the human CTGF mRNA that are hypersensitive to antisense inhibition of mRNA expression. These hypersensitive regions may be structurally more accessible to antisense oligonucleotides. Hypersensitive regions suggested by Round 1 ASO data included regions corresponding to nucleotides 893-931, 960-1008, 1006-1038, 1036-1087, 1109-1151, 1159-1212, 1520-1550 and 1752-1808 of the human CTGF mRNA sequence.

Example 8

Round 2 Experiments

In response to the suggestion of hypersensitive regions in Example 7, further experiments were performed to confirm, extend and where possible, identify the limits of these suspected hypersensitive regions. To this end, 77 additional "Round 2" oligonucleotides (Table 2) were designed that mapped to the regions that surround and/or overlap mRNA sequences that were complementary to 30 "seed" antisense oligonucleotides from Round 1 experiments (Table 1). These seed oligonucleotides inhibited CTGF mRNA expression by at least 60% in Round 1 experiments.

The number of Round 2 oligonucleotides tested for each seed oligonucleotide depended, in part, on the inhibitory activity of the Round 1 oligonucleotides that are adjacent to a specific seed oligonucleotide. For example, FGTC-1240-PS20 (SEQ ID NO: 111) elicited 68.1% CTGF mRNA knockdown in Round 1 experiments and is surrounded by four other Round 1 ASOs that overlap at least five of the same target bases as FGTC-1240-PS20. These adjacent ASOs, however, provided only 27.3% to 46.7% knockdown (mean=37.6%). Therefore, only one flanking Round 2 ASO was synthesized on each side of FGTC-1240-PS20, SEQ ID NO: 111, as the size of a potential hypersensitive region appeared to be limited. On the other hand, FGTC-1122-PS20 (SEQ ID NO: 100) elicited essentially the same degree of mRNA inhibition as FGTC-1240-PS20, SEQ ID NO: 111, (68.2%), but was surrounded by two Round 1 ASOs with at least five overlapping target bases that provided 59.8% and 80.4% CTGF mRNA knockdown. Because this local region appeared unusually enriched, with potent ASO sequences with the potential to represent an extended hypersensitive region, six ASOs were selected for Round 2 testing to probe the region surrounding FGTC-1122-PS20, SEQ ID NO: 100.

Figure 4:
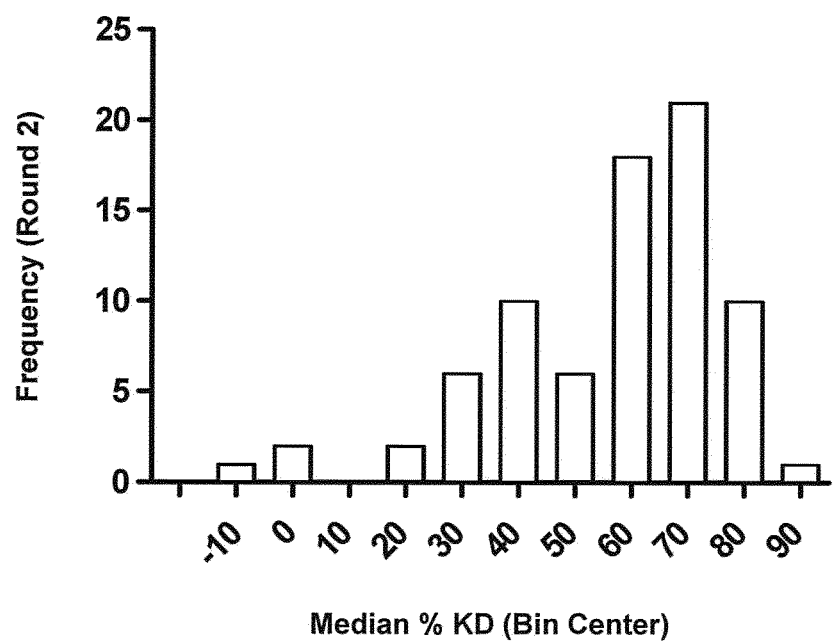
FIG. 4 is a histogram that shows the distribution of Round 2 antisense oligonucleotides based on the percent inhibition of CTGF mRNA expression (knock down) compared to vehicle-treated control. The distribution is shifted to the right compared to the Round 1 distribution shown in FIG. 2 indicating that the population of oligonucleotides is substantially enriched for oligonucleotides that are potent inhibitors of CTGF mRNA activity, i.e., inhibit at least 50% of the CTGF mRNA expression compared to vehicle-treated cells. The Round 2 antisense oligonucleotides were designed to explore the sensitivity to antisense oligonucleotide mediated inhibition of mRNA expression of regions of mRNA immediately adjacent to and overlapping with those that are complementary to "seed" oligonucleotides from Round 1. These seed oligonucleotides induced at least 60% inhibition of CTGF mRNA expression. The results in Round 2 demonstrate that many of the mRNA sequences that are adjacent to and overlapping with those that are complementary to the seed oligonucleotides are also very sensitive to antisense oligonucleotide mediated inhibition of activity. This suggested that there are regions of mRNA that are hypersensitive to antisense oligonucleotide mediated inhibition of mRNA expression, i.e. regions in which hybridization of a complementary antisense oligonucleotide results in at least a 50% reduction in human CTGF mRNA expression.

Each of the Round 2 ASOs was tested in four independent Round 2 experiments conducted in Hs578T cells, the results of which are summarized in Table 2. Notably, a significantly higher proportion of Round 2 than Round 1 ASOs elicited ≥50% inhibition of CTGF mRNA expression (p=3e-10). Thus, the Round 2 ASOs, which were selected because they surrounded the best Round 1 ASOs, were highly enriched for potent ASOs as compared to the starting set of Round 1 screening ASOs. This shift in distributions is shown by comparing FIG. 2 with FIG. 4. The Round 2 data further support the existence of hypersensitivity regions and demonstrates that they are larger than predicted based just on Round 1 data.

TABLE 2

Round 1-3 Antisens Oligonucleotides CTGF mRNA Inhibition

| Round | 5' Target Site | 3' Target Site | Antisense Sequence | % Inhibition | Regional Status | SEQ ID NO |
|---|---|---|---|---|---|---|
| 1 | 5 | 24 | ggggaagagttgttgtgtga | 18.9 | | SEQ ID NO: 2 |
| 1 | 30 | 49 | gtcgcactggctgtctcctc | 21.1 | | SEQ ID NO: 3 |
| 1 | 44 | 63 | agctggagggtggagtcgca | 37.4 | | SEQ ID NO: 4 |
| 1 | 55 | 74 | ggctgccgtcgagctggagg | 31.9 | | SEQ ID NO: 5 |

TABLE 2-continued

Round 1-3 Antisens Oligonucleotides CTGF mRNA Inhibition

| Round | 5' Target Site | 3' Target Site | Antisense Sequence | % Inhibition | Regional Status | SEQ ID NO |
|---|---|---|---|---|---|---|
| 1 | 75 | 94 | tcggggctgtcggccggggc | 6.6 | | SEQ ID NO: 6 |
| 1 | 85 | 104 | ggctgtcgtctcggggctgt | 17.0 | | SEQ ID NO: 7 |
| 1 | 199 | 218 | GGCGGCGGTCATggttggca | -18.6 | | SEQ ID NO: 8 |
| 1 | 210 | 229 | GGGCCCATACTGGCGGCGGT | -0.5 | | SEQ ID NO: 9 |
| 1 | 217 | 236 | GCGGACGGGGCCCATACTGG | 21.2 | | SEQ ID NO: 10 |
| 1 | 222 | 241 | GCGACGCGGACGGGGCCCAT | 42.5 | | SEQ ID NO: 11 |
| 1 | 239 | 258 | CGAGGAGGACCACGAAGGCG | 14.9 | | SEQ ID NO: 12 |
| 1 | 246 | 265 | CAGAGGGCGAGGAGGACCAC | 12.8 | | SEQ ID NO: 13 |
| 1 | 253 | 272 | CCGGCTGCAGAGGGCGAGGA | 26.3 | | SEQ ID NO: 14 |
| 1 | 264 | 283 | CCGACGGCCGGCCGGCTGCA | 14.8 | | SEQ ID NO: 15 |
| 1 | 280 | 299 | CCCGCTGCAGTTCTGGCCGA | -1.3 | | SEQ ID NO: 16 |
| 1 | 284 | 303 | ACGGCCCGCTGCAGTTCTGG | 5.8 | | SEQ ID NO: 17 |
| 1 | 314 | 333 | AGCGCGGCGCCGGCTCGTCC | -16.4 | | SEQ ID NO: 18 |
| 1 | 338 | 357 | GCACGAGGCTCACGCCCGCC | 30.2 | | SEQ ID NO: 19 |
| 1 | 350 | 369 | CGCAGCCGTCCAGCACGAGG | 3.8 | | SEQ ID NO: 20 |
| 1 | 354 | 373 | CAGCCGCAGCCGTCCAGCAC | 17.0 | | SEQ ID NO: 21 |
| 1 | 357 | 376 | CAGCAGCCGCAGCCGTCCAG | -2.5 | | SEQ ID NO: 22 |
| 1 | 358 | 377 | GCAGCAGCCGCAGCCGTCCA | 6.4 | | SEQ ID NO: 23 |
| 1 | 370 | 389 | GGCGCAGACGCGGCAGCAGC | 38.2 | | SEQ ID NO: 24 |
| 1 | 381 | 400 | CCCAGCTGCTTGGCGCAGAC | 48.1 | | SEQ ID NO: 25 |
| 1 | 387 | 406 | AGCTCGCCCAGCTGCTTGGC | 31.1 | | SEQ ID NO: 26 |
| 1 | 397 | 416 | CTCGGTGCACAGCTCGCCCA | 42.5 | | SEQ ID NO: 27 |
| 1 | 409 | 428 | GCATGGGTCGCGCTCGGTGC | -72.2 | | SEQ ID NO: 28 |
| 1 | 415 | 434 | CGGGTCGCATGGGTCGCGCT | 45.8 | | SEQ ID NO: 29 |
| 1 | 430 | 449 | GAAGAGGCCCTTGTGCGGGT | 31.0 | | SEQ ID NO: 30 |
| 1 | 436 | 455 | GTCACAGAAGAGGCCCTTGT | 34.9 | | SEQ ID NO: 31 |
| 1 | 447 | 466 | GGGGAGCCGAAGTCACAGAA | 16.4 | | SEQ ID NO: 32 |
| 1 | 460 | 479 | CTTGCGGTTGGCCGGGGAGC | -57.3 | | SEQ ID NO: 33 |
| 1 | 467 | 486 | CGCCGATCTTGCGGTTGGCC | 9.8 | | SEQ ID NO: 34 |
| 1 | 475 | 494 | GGTGCACACGCCGATCTTGC | 6.4 | | SEQ ID NO: 35 |
| 1 | 486 | 505 | CCATCTTTGGCGGTGCACAC | 25.0 | | SEQ ID NO: 36 |
| 1 | 496 | 515 | GCAGGGAGCACCATCTTTGG | 20.8 | | SEQ ID NO: 37 |
| 1 | 507 | 526 | CCACCGAAGATGCAGGGAGC | 35.3 | | SEQ ID NO: 38 |
| 1 | 514 | 533 | CACCGTACCACCGAAGATGC | 23.9 | | SEQ ID NO: 39 |
| 1 | 528 | 547 | TCTCCGCTGCGGTACACCGT | 7.4 | | SEQ ID NO: 40 |
| 1 | 537 | 556 | TGGAAGGACTCTCCGCTGCG | 36.2 | | SEQ ID NO: 41 |
| 1 | 554 | 573 | GGTACTTGCAGCTGCTCTGG | 38.1 | | SEQ ID NO: 42 |

TABLE 2-continued

Round 1-3 Antisens Oligonucleotides CTGF mRNA Inhibition

| Round | 5' Target Site | 3' Target Site | Antisense Sequence | % Inhibition | Regional Status | SEQ ID NO |
|---|---|---|---|---|---|---|
| 2 | 565 | 584 | GCACGTGCACTGGTACTTGC | 28.4 | | SEQ ID NO: 175 |
| 1 | 567 | 586 | AGGCACGTGCACTGGTACTT | 61.9 | ≥60% | SEQ ID NO: 43 |
| 2 | 569 | 588 | CCAGGCACGTGCACTGGTAC | 57.6 | ≥55% | SEQ ID NO: 176 |
| 1 | 580 | 599 | CACCGCCCCGTCCAGGCACG | 16.3 | | SEQ ID NO: 44 |
| 1 | 584 | 603 | AGCCCACCGCCCCGTCCAGG | 16.2 | | SEQ ID NO: 45 |
| 1 | 589 | 608 | CATGCAGCCCACCGCCCCGT | 23.9 | | SEQ ID NO: 46 |
| 1 | 600 | 619 | CTGCACAGGGGCATGCAGCC | 19.7 | | SEQ ID NO: 47 |
| 1 | 608 | 627 | CGTCCATGCTGCACAGGGGC | 0.2 | | SEQ ID NO: 48 |
| 1 | 613 | 632 | ACGAACGTCCATGCTGCACA | 56.6 | | SEQ ID NO: 49 |
| 1 | 629 | 648 | AGTCAGGGCTGGGCAGACGA | 31.6 | | SEQ ID NO: 50 |
| 1 | 639 | 658 | GGGAAGGGGCAGTCAGGGCT | 13.4 | | SEQ ID NO: 51 |
| 1 | 646 | 665 | CCTCCTCGGGAAGGGGCAGT | 3.2 | | SEQ ID NO: 52 |
| 1 | 657 | 676 | GGCAGCTTGACCCTCCTCGG | 29.0 | | SEQ ID NO: 53 |
| 1 | 661 | 680 | CCCGGGCAGCTTGACCCTCC | 44.7 | | SEQ ID NO: 54 |
| 1 | 677 | 696 | ACTCCTCGCAGCATTTCCCG | 29.6 | | SEQ ID NO: 55 |
| 1 | 684 | 703 | CACACCCACTCCTCGCAGCA | 51.1 | | SEQ ID NO: 56 |
| 1 | 688 | 707 | GTCACACCCACTCCTCGC | 17.8 | | SEQ ID NO: 57 |
| 1 | 692 | 711 | GCTCGTCACACCCACTCC | 44.3 | | SEQ ID NO: 58 |
| 1 | 710 | 729 | CCACGGTTTGGTCCTTGGGC | 34.5 | | SEQ ID NO: 59 |
| 2 | 719 | 738 | CAGGCCCAACCACGGTTTGG | 44.5 | | SEQ ID NO: 177 |
| 1 | 721 | 740 | GGCAGGCCCAACCACGGTTT | *65.8* | | SEQ ID NO: 60 |
| 2 | 723 | 742 | AGGGCAGGCCCAACCACGGT | 30.9 | | SEQ ID NO: 178 |
| 1 | 737 | 756 | GTCGGTAAGCCGCGAGGGCA | 28.5 | | SEQ ID NO: 61 |
| 2 | 745 | 764 | GTCTTCCAGTCGGTAAGCCG | 30.9 | | SEQ ID NO: 179 |
| 1 | 747 | 766 | GTGTCTTCCAGTCGGTAAGC | *68.9* | | SEQ ID NO: 62 |
| 2 | 749 | 768 | ACGTGTCTTCCAGTCGGTAA | 1.2 | | SEQ ID NO: 180 |
| 1 | 754 | 773 | GCCAAACGTGTCTTCCAGTC | 31.4 | | SEQ ID NO: 63 |
| 1 | 762 | 781 | GGGTCTGGGCCAAACGTGTC | 12.5 | | SEQ ID NO: 64 |
| 1 | 772 | 791 | AATCATAGTIGGGTCTGGGC | 33.2 | | SEQ ID NO: 65 |
| 2 | 787 | 806 | CAGGCAGTTGGCTCTAATCA | 48.0 | | SEQ ID NO: 181 |
| 2 | 789 | 808 | ACCAGGCAGTTGGCTCTAAT | 56.5 | ≥55% | SEQ ID NO: 182 |
| 1 | 791 | 810 | GGACCAGGCAGTTGGCTCTA | *67.3* | ≥65% | SEQ ID NO: 66 |
| 2 | 793 | 812 | CTGGACCAGGCAGTTGGCTC | *66.4* | ≥65% | SEQ ID NO: 183 |
| 2 | 795 | 814 | GTCTGGACCAGGCAGTTGGC | 55.4 | ≥55% | SEQ ID NO: 184 |
| 3 | 797 | 816 | TGGTCTGGACCAGGCAGTTG | 32.3 | | SEQ ID NO: 252 |
| 1 | 809 | 828 | CGCTCCACTCTGTGGTCTGG | 34.6 | | SEQ ID NO: 67 |
| 1 | 817 | 836 | GGAACAGGCGCTCCACTCTG | 47.7 | | SEQ ID NO: 68 |

TABLE 2-continued

Round 1-3 Antisens Oligonucleotides CTGF mRNA Inhibition

| Round | 5' Target Site | 3' Target Site | Antisense Sequence | % Inhibition | Regional Status | SEQ ID NO |
|---|---|---|---|---|---|---|
| 1 | 836 | 855 | TGCCCATCCCACAGGTCTTG | 9.1 | | SEQ ID NO: 69 |
| 1 | 841 | 860 | GGAGATGCCCATCCCACAGG | 36.8 | | SEQ ID NO: 70 |
| 2 | 855 | 874 | TTGGTAACCCGGGTGGAGAT | 30.0 | | SEQ ID NO: 185 |
| 2 | 857 | 876 | CATTGGTAACCCGGGTGGAG | 42.0 | | SEQ ID NO: 186 |
| 1 | 859 | 878 | GTCATTGGTAACCCGGGTGG | 58.7 | ≥55% | SEQ ID NO: 71 |
| 2 | 861 | 880 | TTGTCATTGGTAACCCGGGT | 55.4 | ≥55% | SEQ ID NO: 187 |
| 2 | 863 | 882 | CGTTGTCATTGGTAACCCGG | 31.5 | | SEQ ID NO: 188 |
| 1 | 865 | 884 | GGCGTTGTCATTGGTAACCC | 44.0 | | SEQ ID NO: 72 |
| 1 | 870 | 889 | CAGGAGGCGTTGTCATTGGT | 29.4 | | SEQ ID NO: 73 |
| 1 | 889 | 908 | GCTCTGCTTCTCTAGCCTGC | 13.8 | | SEQ ID NO: 74 |
| 1 | 893 | 912 | GGCGGCTCTGCTTCTCTAGC | 51.6 | ≥50% | SEQ ID NO: 75 |
| 1 | 904 | 923 | GACCATGCACAGGCGGCTCT | 50.4 | ≥50% | SEQ ID NO: 76 |
| 2 | 908 | 927 | GCCTGACCATGCACAGGCGG | 37.8 | | SEQ ID NO: 189 |
| 2 | 910 | 929 | AGGCCTGACCATGCACAGGC | 0.5 | | SEQ ID NO: 190 |
| 1 | 912 | 931 | CAAGGCCTGACCATGCACAG | 55.3 | | SEQ ID NO: 77 |
| 2 | 914 | 933 | CGCAAGGCCTGACCATGCAC | 36.2 | | SEQ ID NO: 191 |
| 2 | 916 | 935 | TTCGCAAGGCCTGACCATGC | 60.0 | | SEQ ID NO: 192 |
| 1 | 931 | 950 | CTCTTCCAGGTCAGCTTCGC | 27.1 | | SEQ ID NO: 78 |
| 1 | 935 | 954 | TGTTCTCTTCCAGGTCAGCT | 51.6 | ≥50% | SEQ ID NO: 79 |
| 1 | 946 | 965 | GCCCTTCTTAATGTTCTCTT | 62.7 | ≥60% | SEQ ID NO: 80 |
| 3 | 948 | 967 | TTGCCCTTCTTAATGTTCTC | *71.9* | ≥70% | SEQ ID NO: 253 |
| 3 | 950 | 969 | TTTTGCCCTTCTTAATGTTC | 55.3 | ≥55% | SEQ ID NO: 254 |
| 3 | 952 | 971 | CTTTTTGCCCTTCTTAATGT | 53.1 | ≥50% | SEQ ID NO: 255 |
| 3 | 954 | 973 | CACTTTTTGCCCTTCTTAAT | 59.4 | ≥55% | SEQ ID NO: 256 |
| 2 | 956 | 975 | TGCACTTTTTGCCCTTCTTA | *76.6* | ≥75% | SEQ ID NO: 193 |
| 2 | 958 | 977 | GATGCACTTTTTGCCCTTCT | *82.2* | ≥80% | SEQ ID NO: 194 |
| 1 | 960 | 979 | CGGATGCACTTTTTGCCCTT | *67.8* | ≥65% | SEQ ID NO: 81 |
| 2 | 962 | 981 | TACGGATGCACTTTTTGCCC | *79.8* | ≥75% | SEQ ID NO: 195 |
| 2 | 965 | 984 | GAGTACGGATGCACTTTTTG | *75.3* | ≥75% | SEQ ID NO: 196 |
| 1 | 967 | 986 | GGGAGTACGGATGCACTTTT | *73.0* | ≥70% | SEQ ID NO: 82 |
| 2 | 969 | 988 | TTGGGAGTACGGATGCACTT | *68.0* | ≥65% | SEQ ID NO: 197 |
| 2 | 971 | 990 | TTTTGGGAGTACGGATGCAC | 47.8 | | SEQ ID NO: 198 |
| 3 | 976 | 995 | GGAGATTTGGGAGTACGGA | 31.4 | | SEQ ID NO: 257 |
| 3 | 979 | 998 | CTTGGAGATTTTGGGAGTAC | 41.1 | | SEQ ID NO: 258 |
| 1 | 981 | 1000 | GGCTTGGAGATTTTGGGAGT | 58.2 | ≥55% | SEQ ID NO: 83 |
| 3 | 983 | 1002 | TAGGCTTGGAGATTTTGGGA | 60.3 | ≥60% | SEQ ID NO: 259 |

TABLE 2-continued

Round 1-3 Antisens Oligonucleotides CTGF mRNA Inhibition

| Round | 5' Target Site | 3' Target Site | Antisense Sequence | % Inhibition | Regional Status | SEQ ID NO |
|---|---|---|---|---|---|---|
| 2 | 987 | 1006 | TTGATAGGCTTGGAGATTTT | 49.2 | | SEQ ID NO: 199 |
| 1 | 989 | 1008 | ACTTGATAGGCTTGGAGATT | 64.1 | ≥60% | SEQ ID NO: 84 |
| 2 | 991 | 1010 | AAACTTGATAGGCTTGGAGA | *65.7* | ≥65% | SEQ ID NO: 200 |
| 3 | 993 | 1012 | TCAAACTTGATAGGCTTGGA | 39.6 | | SEQ ID NO: 260 |
| 1 | 995 | 1014 | GCTCAAACTTGATAGGCTTG | 38.7 | | SEQ ID NO: 85 |
| 1 | 1003 | 1022 | GCCAGAAAGCTCAAACTTGA | 38.1 | | SEQ ID NO: 86 |
| 2 | 1004 | 1023 | AGCCAGAAAGCTCAAACTTG | 21.9 | | SEQ ID NO: 201 |
| 1 | 1006 | 1025 | GCAGCCAGAAAGCTCAAAT | 62.4 | ≥60% | SEQ ID NO: 87 |
| 2 | 1008 | 1027 | GTGCAGCCAGAAAGCTCAAA | 56.2 | ≥55% | SEQ ID NO: 202 |
| 3 | 1011 | 1030 | CTGGTGCAGCCAGAAAGCTC | *68.9* | ≥65% | SEQ ID NO: 261 |
| 3 | 1013 | 1032 | TGCTGGTGCAGCCAGAAAGC | *67.2* | ≥65% | SEQ ID NO: 262 |
| 2 | 1015 | 1034 | CATGCTGGTGCAGCCAGAAA | *67.7* | ≥65% | SEQ ID NO: 203 |
| 2 | 1017 | 1036 | TTCATGCTGGTGCAGCCAGA | *84.7* | ≥80% | SEQ ID NO: 204 |
| 1 | 1019 | 1038 | TCTTCATGCTGGTGCAGCCA | *71.0* | ≥70% | SEQ ID NO: 88 |
| 2 | 1021 | 1040 | TGTCTTCATGCTGGTGCAGC | *71.3* | ≥70% | SEQ ID NO: 205 |
| 2 | 1023 | 1042 | TATGTCTTCATGCTGGTGCA | *76.1* | ≥75% | SEQ ID NO: 206 |
| 3 | 1025 | 1044 | GGTATGTCTTCATGCTGGTG | 52.3 | ≥50% | SEQ ID NO: 263 |
| 3 | 1027 | 1046 | TCGGTATGTCTTCATGCTGG | 44.1 | | SEQ ID NO: 264 |
| 1 | 1029 | 1048 | GCTCGGTATGTCTTCATGCT | 47.0 | | SEQ ID NO: 89 |
| 3 | 1032 | 1051 | TTAGCTCGGTATGTCTTCAT | 50.0 | ≥50% | SEQ ID NO: 265 |
| 2 | 1034 | 1053 | ATTTAGCTCGGTATGTCTTC | *69.5* | ≥65% | SEQ ID NO: 207 |
| 1 | 1036 | 1055 | GAATTTAGCTCGGTATGTCT | *65.1* | ≥65% | SEQ ID NO: 90 |
| 2 | 1039 | 1058 | ACAGAATTTAGCTCGGTATG | −11.2 | | SEQ ID NO: 208 |
| 3 | 1041 | 1060 | CCACAGAATTTAGCTCGGTA | 29.8 | | SEQ ID NO: 266 |
| 1 | 1043 | 1062 | CTCCACAGAATTTAGCTCGG | *65.9* | | SEQ ID NO: 91 |
| 2 | 1045 | 1064 | TACTCCACAGAATTTAGCTC | 42.4 | | SEQ ID NO: 209 |
| 2 | 1055 | 1074 | CGTCGGTACATACTCCACAG | 39.5 | | SEQ ID NO: 210 |
| 1 | 1057 | 1076 | GCCGTCGGTACATACTCCAC | *66.2* | | SEQ ID NO: 92 |
| 2 | 1059 | 1078 | CGGCCGTCGGTACATACTCC | 35.5 | | SEQ ID NO: 211 |
| 2 | 1061 | 1080 | ATCGGCCGTCGGTACATACT | 57.6 | ≥55% | SEQ ID NO: 212 |
| 2 | 1064 | 1083 | AGCATCGGCCGTCGGTACAT | *66.1* | ≥65% | SEQ ID NO: 213 |
| 2 | 1066 | 1085 | GCAGCATCGGCCGTCGGTAC | *73.8* | ≥70% | SEQ ID NO: 214 |
| 1 | 1068 | 1087 | GTGCAGCATCGGCCGTCGGT | *66.1* | ≥65% | SEQ ID NO: 93 |
| 2 | 1070 | 1089 | GGGTGCAGCATCGGCCGTCG | *72.8* | ≥70% | SEQ ID NO: 215 |
| 1 | 1071 | 1090 | GGGGTGCAGCATCGGCCGTC | 49.3 | | SEQ ID NO: 94 |
| 1 | 1074 | 1093 | TGGGGGGTGCAGCATCGGCC | 37.7 | | SEQ ID NO: 95 |

TABLE 2-continued

Round 1-3 Antisens Oligonucleotides CTGF mRNA Inhibition

| Round | 5' Target Site | 3' Target Site | Antisense Sequence | % Inhibition | Regional Status | SEQ ID NO |
|---|---|---|---|---|---|---|
| 1 | 1081 | 1100 | GGTTCTGTGGGGGGTGCAGC | 22.3 | | SEQ ID NO: 96 |
| 1 | 1088 | 1107 | GGGTGGTGGTTCTGTGGGGG | -11.4 | | SEQ ID NO: 97 |
| 1 | 1093 | 1112 | CGGCAGGGTGGTGGTTCTGT | 42.0 | | SEQ ID NO: 98 |
| 2 | 1105 | 1124 | CTTGAACTCCACCGGCAGGG | 46.1 | | SEQ ID NO: 216 |
| 2 | 1107 | 1126 | CACTTGAACTCCACCGGCAG | 50.5 | ≥50% | SEQ ID NO: 217 |
| 1 | 1109 | 1128 | GGCACTTGAACTCCACCGGC | *69.9* | ≥65% | SEQ ID NO: 99 |
| 2 | 1111 | 1130 | AGGGCACTTGAACTCCACCG | *68.1* | ≥65% | SEQ ID NO: 218 |
| 2 | 1113 | 1132 | TCAGGGCACTTGAACTCCAC | *69.0* | ≥65% | SEQ ID NO: 219 |
| 3 | 1116 | 1135 | CCGTCAGGGCACTTGAACTC | 60.7 | ≥60% | SEQ ID NO: 267 |
| 2 | 1118 | 1137 | CGCCGTCAGGGCACTTGAAC | *73.6* | ≥70% | SEQ ID NO: 220 |
| 2 | 1120 | 1139 | CTCGCCGTCAGGGCACTTGA | *70.2* | ≥70% | SEQ ID NO: 221 |
| 1 | 1122 | 1141 | ACCTCGCCGTCAGGGCACTT | *68.2* | ≥65% | SEQ ID NO: 100 |
| 2 | 1124 | 1143 | TGACCTCGCCGTCAGGGCAC | *76.0* | ≥75% | SEQ ID NO: 222 |
| 2 | 1126 | 1145 | CATGACCTCGCCGTCAGGGC | *69.0* | ≥65% | SEQ ID NO: 223 |
| 3 | 1128 | 1147 | TTCATGACCTCGCCGTCAGG | 38.3 | | SEQ ID NO: 268 |
| 3 | 1130 | 1149 | TCTTCATGACCTCGCCGTCA | 44.1 | | SEQ ID NO: 269 |
| 1 | 1132 | 1151 | CTTCTTCATGACCTCGCCGT | 59.8 | ≥55% | SEQ ID NO: 101 |
| 3 | 1134 | 1153 | TTCTTCTTCATGACCTCGCC | 51.0 | ≥50% | SEQ ID NO: 270 |
| 1 | 1142 | 1161 | ACATCATGTTCTTCTTCATG | -4.2 | | SEQ ID NO: 102 |
| 2 | 1157 | 1176 | CACAGGTCTTGATGAACATC | 44.7 | | SEQ ID NO: 224 |
| 1 | 1159 | 1178 | GGCACAGGTCTTGATGAACA | 64.4 | | SEQ ID NO: 103 |
| 2 | 1161 | 1180 | CAGGCACAGGTCTTGATGAA | 46.5 | | SEQ ID NO: 225 |
| 3 | 1164 | 1183 | TGGCAGGCACAGGTCTTGAT | 52.6 | ≥50% | SEQ ID NO: 271 |
| 2 | 1166 | 1185 | AATGGCAGGCACAGGTCTTG | *65.4* | ≥65% | SEQ ID NO: 226 |
| 1 | 1168 | 1187 | GTAATGGCAGGCACAGGTCT | *66.4* | ≥65% | SEQ ID NO: 104 |
| 2 | 1170 | 1189 | TTGTAATGGCAGGCACAGGT | 60.9 | ≥60% | SEQ ID NO: 227 |
| 3 | 1172 | 1191 | AGTTGTAATGGCAGGCACAG | 52.8 | ≥50% | SEQ ID NO: 272 |
| 2 | 1175 | 1194 | GACAGTTGTAATGGCAGGCA | 62.0 | ≥60% | SEQ ID NO: 228 |
| 2 | 1177 | 1196 | GGGACAGTTGTAATGGCAGG | 36.4 | | SEQ ID NO: 229 |
| 1 | 1179 | 1198 | CCGGGACAGTTGTAATGGCA | *65.4* | ≥65% | SEQ ID NO: 105 |
| 1 | 1181 | 1200 | CTCCGGGACAGTTGTAATGG | 64.3 | ≥60% | SEQ ID NO: 230 |
| 2 | 1183 | 1202 | GTCTCCGGGACAGTTGTAAT | *67.7* | ≥65% | SEQ ID NO: 231 |
| 3 | 1185 | 1204 | TTGTCTCCGGGACAGTTGTA | *66.6* | ≥65% | SEQ ID NO: 273 |
| 3 | 1187 | 1260 | CATTGTCTCCGGGACAGTTG | *72.0* | ≥70% | SEQ ID NO: 274 |
| 3 | 1189 | 1208 | GTCATTGTCTCCGGGACAGT | 61.3 | ≥60% | SEQ ID NO: 275 |
| 2 | 1191 | 1210 | ATGTCATTGTCTCCGGGACA | *74.6* | ≥70% | SEQ ID NO: 232 |

TABLE 2-continued

Round 1-3 Antisens Oligonucleotides CTGF mRNA Inhibition

| Round | 5' Target Site | 3' Target Site | Antisense Sequence | % Inhibition | Regional Status | SEQ ID NO |
|---|---|---|---|---|---|---|
| 1 | 1193 | 1212 | AGATGTCATTGTCTCCGGGA | *69.4* | ≥65% | SEQ ID NO: 106 |
| 2 | 1195 | 1214 | AAAGATGTCATTGTCTCCGG | *67.5* | ≥65% | SEQ ID NO: 233 |
| 3 | 1197 | 1216 | TCAAAGATGTCATTGTCTCC | 51.8 | ≥50% | SEQ ID NO: 276 |
| 3 | 1199 | 1218 | ATTCAAAGATGTCATTGTCT | 42.4 | | SEQ ID NO: 277 |
| 3 | 1201 | 1220 | CGATTCAAAGATGTCATTGT | 12.2 | | SEQ ID NO: 278 |
| 3 | 1203 | 1222 | AGCGATTCAAAGATGTCATT | 55.7 | | SEQ ID NO: 279 |
| 1 | 1205 | 1224 | ACAGCGATTCAAAGATGTCA | 31.9 | | SEQ ID NO: 107 |
| 3 | 1209 | 1228 | TAGTACAGCGATTCAAAGAT | 38.7 | | SEQ ID NO: 280 |
| 1 | 1211 | 1230 | TGTAGTACAGCGATTCAAAG | 58.5 | ≥55% | SEQ ID NO: 108 |
| 3 | 1213 | 1232 | CCTGTAGTACAGCGATTCAA | 61.2 | ≥60% | SEQ ID NO: 281 |
| 1 | 1228 | 1247 | GTCTCCGTACATCTTCCTGT | 55.7 | ≥55% | SEQ ID NO: 109 |
| 1 | 1233 | 1252 | GCCATGTCTCCGTACATCTT | 40.0 | | SEQ ID NO: 110 |
| 3 | 1236 | 1255 | CATGCCATGTCTCCGTACAT | 55.6 | ≥55% | SEQ ID NO: 282 |
| 2 | 1238 | 1257 | tTCATGCCATGTCTCCGTAC | *71.3* | ≥70% | SEQ ID NO: 234 |
| 1 | 1240 | 1259 | gctTCATGCCATGTCTCCGT | *68.1* | ≥65% | SEQ ID NO: 111 |
| 2 | 1242 | 1261 | tggctTCATGCCATGTCTCC | *71.1* | ≥70% | SEQ ID NO: 235 |
| 3 | 1244 | 1263 | tctggctTCATGCCATGTCT | 53.0 | ≥50% | SEQ ID NO: 283 |
| 3 | 1246 | 1265 | tctctggctTCATGCCATGT | *69.5* | ≥65% | SEQ ID NO: 284 |
| 1 | 1249 | 1268 | cactctctggctTCATGCCA | 36.3 | | SEQ ID NO: 112 |
| 1 | 1255 | 1274 | gtctctcactctctggctTC | 46.7 | | SEQ ID NO: 113 |
| 1 | 1261 | 1280 | gttaatgtctctcactctct | 42.5 | | SEQ ID NO: 114 |
| 1 | 1286 | 1305 | atcagttcaagttccagtct | 43.8 | | SEQ ID NO: 115 |
| 1 | 1305 | 1324 | acggaaaaatgagatgtgaa | 17.3 | | SEQ ID NO: 116 |
| 1 | 1320 | 1339 | actgaaatcatttttacgga | -0.7 | | SEQ ID NO: 117 |
| 3 | 1327 | 1346 | ttgtgctactgaaatcattt | 37.6 | | SEQ ID NO: 285 |
| 1 | 1329 | 1348 | acttgtgctactgaaatcat | 58.3 | ≥55% | SEQ ID NO: 118 |
| 3 | 1331 | 1350 | taacttgtgctactgaaatc | 59.6 | ≥55% | SEQ ID NO: 286 |
| 1 | 1357 | 1376 | cccccagttagaaaaacaga | 35.5 | | SEQ ID NO: 119 |
| 1 | 1366 | 1385 | gaatcttttcccccagttag | 47.1 | | SEQ ID NO: 120 |
| 1 | 1384 | 1403 | atgttttgaattgggtggga | 5.5 | | SEQ ID NO: 121 |
| 1 | 1405 | 1424 | ctatttgtttgacatggcac | 43.0 | | SEQ ID NO: 122 |
| 1 | 1417 | 1436 | ggggttgatagactatttgt | 9.9 | | SEQ ID NO: 123 |
| 1 | 1425 | 1444 | cagtgtctggggttgataga | 43.3 | | SEQ ID NO: 124 |
| 1 | 1437 | 1456 | cattcttcaaaccagtgtct | 14.0 | | SEQ ID NO: 125 |
| 1 | 1455 | 1474 | tccactgtcaagtcttaaca | 23.7 | | SEQ ID NO: 126 |
| 1 | 1460 | 1479 | gtagttccactgtcaagtct | 49.7 | | SEQ ID NO: 127 |
| 1 | 1483 | 1502 | acattctggtgctgtgtact | 48.4 | | SEQ ID NO: 128 |

TABLE 2-continued

Round 1-3 Antisens Oligonucleotides CTGF mRNA Inhibition

| Round | 5' Target Site | 3' Target Site | Antisense Sequence | % Inhibition | Regional Status | SEQ ID NO |
|---|---|---|---|---|---|---|
| 1 | 1498 | 1517 | gccacaccttaatatacatt | 48.2 | | SEQ ID NO: 129 |
| 1 | 1514 | 1533 | tcccactgctcctaaagcca | 56.3 | ≥55% | SEQ ID NO: 130 |
| 3 | 1516 | 1535 | cctcccactgctcctaaagc | 59.5 | ≥55% | SEQ ID NO: 287 |
| 2 | 1518 | 1537 | accctcccactgctcctaaa | *68.2* | ≥65% | SEQ ID NO: 236 |
| 1 | 1520 | 1539 | gtaccctcccactgctccta | 64.5 | ≥60% | SEQ ID NO: 131 |
| 3 | 1522 | 1541 | tggtaccctcccactgctcc | 57.4 | ≥55% | SEQ ID NO: 288 |
| 2 | 1524 | 1543 | gctggtaccctcccactgct | *69.2* | ≥65% | SEQ ID NO: 237 |
| 1 | 1527 | 1546 | tctgctggtaccctcccact | 64.4 | ≥60% | SEQ ID NO: 132 |
| 2 | 1529 | 1548 | tttctgctggtaccctccca | 53.8 | ≥50% | SEQ ID NO: 238 |
| 1 | 1531 | 1550 | cctttctgctggtaccctcc | 59.4 | ≥55% | SEQ ID NO: 133 |
| 3 | 1533 | 1552 | aacctttctgctggtaccct | *68.4* | ≥65% | SEQ ID NO: 289 |
| 1 | 1549 | 1568 | gctatctgatgatactaacc | 46.0 | | SEQ ID NO: 134 |
| 1 | 1574 | 1593 | agcaggcatattactcgtat | 52.0 | | SEQ ID NO: 135 |
| 1 | 1585 | 1604 | acacttcaaatagcaggcat | 41.0 | | SEQ ID NO: 136 |
| 1 | 1597 | 1616 | tccttctcaattacacttca | 14.9 | | SEQ ID NO: 137 |
| 3 | 1617 | 1636 | cagtgagcacgctaaaattt | 54.0 | | SEQ ID NO: 290 |
| 1 | 1620 | 1639 | ggtcagtgagcacgctaaaa | 40.3 | | SEQ ID NO: 138 |
| 3 | 1623 | 1642 | gcaggtcagtgagcacgcta | 62.6 | ≥60% | SEQ ID NO: 291 |
| 3 | 1625 | 1644 | aggcaggtcagtgagcacgc | 64.8 | ≥60% | SEQ ID NO: 292 |
| 3 | 1627 | 1646 | acaggcaggtcagtgagcac | 56.2 | ≥55% | SEQ ID NO: 293 |
| 2 | 1629 | 1648 | ctacaggcaggtcagtgagc | 62.5 | ≥60% | SEQ ID NO: 239 |
| 2 | 1631 | 1650 | ggctacaggcaggtcagtga | *67.3* | ≥65% | SEQ ID NO: 240 |
| 1 | 1633 | 1652 | ggggctacaggcaggtcagt | *69.4* | ≥65% | SEQ ID NO: 139 |
| 2 | 1635 | 1654 | ctggggctacaggcaggtca | 62.5 | ≥60% | SEQ ID NO: 241 |
| 2 | 1637 | 1656 | cactggggctacaggcaggt | *65.2* | ≥65% | SEQ ID NO: 242 |
| 3 | 1639 | 1658 | gtcactggggctacaggcag | 46.9 | | SEQ ID NO: 294 |
| 3 | 1641 | 1660 | ctgtcactggggctacaggc | 44.1 | | SEQ ID NO: 295 |
| 3 | 1643 | 1662 | agctgtdactggggctacag | 58.2 | | SEQ ID NO: 296 |
| 3 | 1645 | 1664 | ctagctgtcactggggctac | 36.3 | | SEQ ID NO: 297 |
| 1 | 1647 | 1666 | tcctagctgtcactggggct | 48.3 | | SEQ ID NO: 140 |
| 3 | 1649 | 1668 | catcctagctgtcactgggg | 49.6 | | SEQ ID NO: 298 |
| 2 | 1651 | 1670 | cacatcctagctgtcactgg | 56.0 | ≥55% | SEQ ID NO: 243 |
| 1 | 1653 | 1672 | tgcacatcctagctgtcact | 60.4 | ≥60% | SEQ ID NO: 141 |
| 2 | 1655 | 1674 | aatgcacatcctagctgtca | 43.5 | | SEQ ID NO: 244 |
| 1 | 1670 | 1689 | tcttgatggctggagaatgc | 49.3 | | SEQ ID NO: 142 |
| 1 | 1681 | 1700 | ttgactcagtctcttgatgg | 10.1 | | SEQ ID NO: 143 |

TABLE 2-continued

Round 1-3 Antisens Oligonucleotides CTGF mRNA Inhibition

| Round | 5' Target Site | 3' Target Site | Antisense Sequence | % Inhibition | Regional Status | SEQ ID NO |
|---|---|---|---|---|---|---|
| 1 | 1712 | 1731 | ctgagtctgctgttctgact | 30.9 | | SEQ ID NO: 144 |
| 1 | 1740 | 1759 | cagtgtcattcgaatcagaa | 37.4 | | SEQ ID NO: 145 |
| 3 | 1750 | 1769 | gattcctgaacagtgtcatt | 53.9 | ≥50% | SEQ ID NO: 299 |
| 1 | 1752 | 1771 | ccgattcctgaacagtgtca | 59.5 | ≥55% | SEQ ID NO: 146 |
| 3 | 1755 | 1774 | attccgattcctgaacagtg | 50.2 | ≥50% | SEQ ID NO: 300 |
| 3 | 1757 | 1776 | ggattccgattcctgaacag | 45.7 | | SEQ ID NO: 301 |
| 3 | 1759 | 1778 | caggattccgattcctgaac | 51.1 | ≥50% | SEQ ID NO: 302 |
| 2 | 1761 | 1780 | gacaggattccgattcctga | 60.3 | ≥60% | SEQ ID NO: 245 |
| 1 | 1763 | 1782 | tcgacaggattccgattcct | 62.8 | ≥60% | SEQ ID NO: 147 |
| 2 | 1765 | 1784 | aatcgacaggattccgattc | 65.0 | ≥65% | SEQ ID NO: 246 |
| 3 | 1767 | 1786 | ctaatcgacaggattccgat | 55.2 | ≥55% | SEQ ID NO: 303 |
| 3 | 1769 | 1788 | gtctaatcgacaggattccg | 45.1 | | SEQ ID NO: 304 |
| 3 | 1771 | 1790 | cagtctaatcgacaggattc | 64.5 | ≥60% | SEQ ID NO: 305 |
| 3 | 1773 | 1792 | tccagtctaattgacaggat | 59.8 | ≥55% | SEQ ID NO: 306 |
| 3 | 1775 | 1794 | tgtccagtctaatcgacagg | 66.7 | ≥65% | SEQ ID NO: 307 |
| 3 | 1777 | 1796 | gctgtccagtctaatcgaca | 51.0 | ≥50% | SEQ ID NO: 308 |
| 2 | 1779 | 1798 | aagctgtccagtctaatcga | 64.0 | ≥60% | SEQ ID NO: 247 |
| 2 | 1781 | 1800 | acaagctgtccagtctaatc | 59.8 | ≥55% | SEQ ID NO: 248 |
| 1 | 1783 | 1801 | ccacaagctgtccagtctaa | 71.7 | ≥70% | SEQ ID NO: 148 |
| 1 | 1785 | 1804 | tgccacaagctgtccagtct | 67.7 | ≥65% | SEQ ID NO: 149 |
| 2 | 1787 | 1806 | cttgccacaagctgtccagt | 62.9 | ≥60% | SEQ ID NO: 249 |
| 1 | 1789 | 1808 | cacttgccacaagctgtcca | 70.3 | ≥70% | SEQ ID NO: 150 |
| 2 | 1791 | 1810 | ttcacttgccacaagctgtc | 19.9 | | SEQ ID NO: 250 |
| 2 | 1793 | 1812 | aattcacttgccacaagctg | 62.6 | ≥60% | SEQ ID NO: 251 |
| 3 | 1795 | 1814 | caaattcacttgccacaagc | 58.7 | ≥55% | SEQ ID NO: 309 |
| 3 | 1797 | 1816 | ggcaaattcacttgccacaa | 50.1 | ≥50% | SEQ ID NO: 310 |
| 3 | 1799 | 1818 | caggcaaattcacttgccac | 52.2 | ≥50% | SEQ ID NO: 311 |
| 3 | 1801 | 1820 | tacaggcaaattcacttgcc | 51.2 | ≥50% | SEQ ID NO: 312 |
| 1 | 1803 | 1822 | gttacaggcaaattcacttg | 20.3 | | SEQ ID NO: 151 |
| 3 | 1891 | 1910 | ttaacttagataactgtaca | 25.1 | | SEQ ID NO: 313 |
| 1 | 1892 | 1911 | attaacttagataactgtac | -3.3 | | SEQ ID NO: 152 |
| 1 | 1909 | 1928 | ggcacaaacaactttaaatt | 40.3 | | SEQ ID NO: 153 |
| 1 | 1962 | 1981 | cagaaattgaggctaacatt | 16.6 | | SEQ ID NO: 154 |
| 1 | 1980 | 1999 | cattctacctatggtgttca | 41.8 | | SEQ ID NO: 155 |
| 1 | 1986 | 2005 | gctttacattctacctatgg | 23.7 | | SEQ ID NO: 156 |
| 1 | 1998 | 2017 | acgatcagacaagctttaca | 34.5 | | SEQ ID NO: 157 |
| 1 | 2018 | 2037 | gtatccatttcatgctttga | 38.1 | | SEQ ID NO: 158 |

TABLE 2-continued

Round 1-3 Antisens Oligonucleotides CTGF mRNA Inhibition

| Round | 5' Target Site | 3' Target Site | Antisense Sequence | % Inhibition | Regional Status | SEQ ID NO |
|---|---|---|---|---|---|---|
| 1 | 2026 | 2045 | ccatataagtatccatttca | 22.0 | | SEQ ID NO: 159 |
| 1 | 2052 | 1071 | actgtcattctatctgagca | 33.3 | | SEQ ID NO: 160 |
| 1 | 2056 | 2075 | acggactgtcattctatctg | 18.8 | | SEQ ID NO: 161 |
| 1 | 2086 | 2105 | atgcctccctttgcaaaca | 21.4 | | SEQ ID NO: 162 |
| 1 | 2091 | 2110 | cactgatgcctcccctttgc | 53.8 | | SEQ ID NO: 163 |
| 1 | 2115 | 2134 | acctagaaatcagcctgcca | 36.0 | | SEQ ID NO: 164 |
| 1 | 2131 | 2150 | ggctaccacatttcctacct | 32.6 | | SEQ ID NO: 165 |
| 1 | 2153 | 2172 | gccatttgttcattaaaagt | 11.1 | | SEQ ID NO: 166 |
| 1 | 2175 | 2194 | agtcactcagtttttaataa | 19.4 | | SEQ ID NO: 167 |
| 1 | 2184 | 2203 | gctatatagagtcactcagt | 21.1 | | SEQ ID NO: 168 |
| 1 | 2208 | 2227 | gcttccaggtgaaaaaactg | 22.8 | | SEQ ID NO: 169 |
| 3 | 2213 | 2232 | caaatgcttccaggtgaaaa | 37.3 | | SEQ ID NO: 314 |
| 1 | 2215 | 2234 | aacaaatgcttccaggtgaa | 55.8 | | SEQ ID NO: 170 |
| 3 | 2217 | 2236 | gaaacaaatgcttccaggtg | -0.2 | | SEQ ID NO: 315 |
| 1 | 2221 | 2240 | agtagaaacaaatgcttcca | 5.6 | | SEQ ID NO: 171 |
| 1 | 2243 | 2262 | gtccgaaaaacagtcatatc | 43.4 | | SEQ ID NO: 172 |
| 1 | 2258 | 2277 | ctcaacaaataaactgtccg | 39.2 | | SEQ ID NO: 173 |
| 3 | 2267 | 2286 | ggtcacactctcaacaaata | 46.1 | | SEQ ID NO: 316 |
| 3 | 2282 | 2301 | aaacatgtaacttttggtca | 20.7 | | SEQ ID NO: 317 |
| 1 | 2311 | 2330 | atacactttattttcaacta | 31.0 | | SEQ ID NO: 174 |

Table 2. Combined median values from 3 or more independent experiments in which the indicated antisense oligonucleotides were tested. 20-nucleotide-long oligodeoxyribonucleotides with phosphorothioate internucleoside linkages throughout the oligonucleotide were assessed for inhibition of CTGF mRNA expression, expressed here as % inhibition vs. vehicle-treated control. The 5' and 3' target sites denote the 5'-most and 3'-most complementary (sense) bases of the splice human connective tissue growth factor mRNA sequence (GenBank accession number NM_001901, SEQ ID NO: 1). An "m" suffix denotes an oligonucleotide that crosses an exon-exon boundary and thus is only complementary to the splice mRNA. All other ASOs are complementary to both the spliced mRNA and non-spliced pre-mRNA. The values provided in Table 2 also take into account data obtained from Round 3 experiments for 29 "bridging" ASOs included in Round 1 and Round 3 studies as well as "bridging" ASOs included in both Round 2 and Round 3 studies. The percent inhibition values for these bridging ASOs were highly correlated across Rounds (r ≥ 0.81, p < 1e-6).

Example 9

Round 3 Experiments

Based on the results achieved in the Round 2 studies, 66 additional "Round 3" antisense oligonucleotides were chosen to further refine the boundaries of human CTGF mRNA hypersensitive regions from Round 1 and Round 2, or to evaluate other regions not probed as intensely in Round 1 or Round 2. Specifically, in choosing new ASOs to test, antisense oligonucleotides that differed in position by a single base from a Round 1 or Round 2 oligonucleotide were avoided in favor of those that differed by at least two of three bases. Additionally, in refining hypersensitive regions, if the potent ASO that defined the end of a hypersensitive region provided >60% CTGF mRNA knockdown in Round 1 or Round 2, then sufficient ASOs were chosen to probe the sequence between the end of the hypersensitive region and the next sequence that was probed in Round 1 or Round 2. If the potent ASO that defined the end of a hypersensitive region provided 55%-60% CTGF mRNA knockdown in Round 1 or Round 2, then, a single flanking ASO was tested. If the potent ASO that defined the end of a hypersensitive region provided <55% KD Round 1 or Round 2, then the limits of the hypersensitive region was judged defined, and no further testing was performed. Additionally, isolated potent ASOs that provided 55-60% KD in Round 1 or Round 2 were tested on each side with a flanking oligonucleotide that differed by 1 or 2 nucleotides.

Each of the Round 3 ASOs were tested in three Round 3 experiments, the results of which further extended and refined the hypersensitive regions of the human CTGF mRNA previously identified by ASO knockdown in Rounds 1 and 2 (Table 2). Round 3 experiments included 29 Round 1 and 25 Round 2 ASOs that served as Round-to-Round "bridging" controls. Thirty three of the bridging controls conferred >70% CTGF mRNA knockdown (KD) in prior Round 1 or Round 2 experiments. The remaining controls were defined as "non-specific", i.e., conferred <34% CTGF mRNA KD. These bridging controls produced similar results in the Round 3 experiments compared to what was observed in prior Rounds (r=0.86, p<1e-16), further demonstrating the reproducibility of the assay system.

Figure 5:
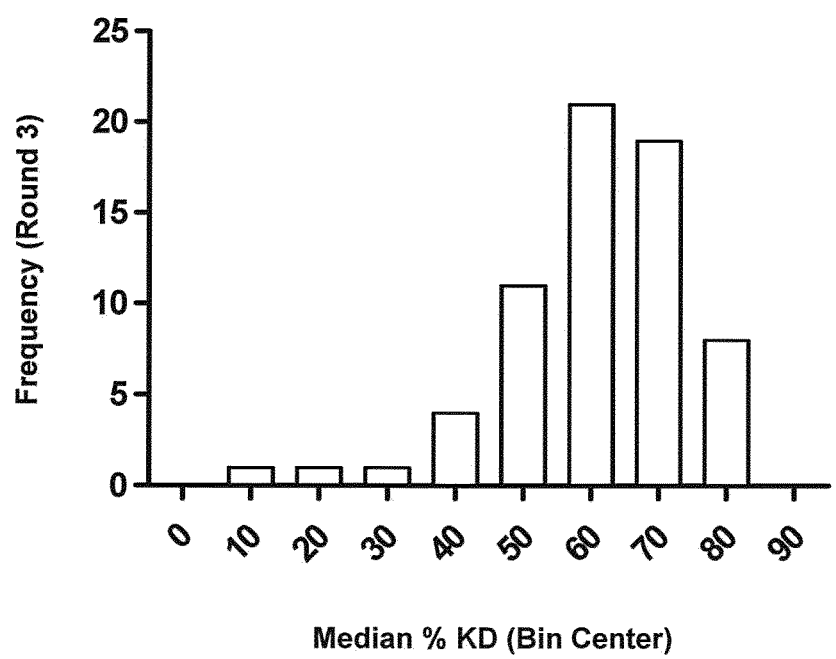
FIG. 5 is a histogram that shows the distribution of Round 3 antisense oligonucleotides based on percent inhibition of CTGF mRNA expression (knock down) compared to vehicle-treated control. Like the Round 2 antisense oligonucleotides, the Round 3 antisense oligonucleotides are substantially enriched for oligonucleotides that are potent inhibitors of CTGF mRNA activity. The oligonucleotides synthesized in Round 3 were designed to test the boundaries of hypersensitive regions identified in Round 1 and Round 2.
Figure 6A:
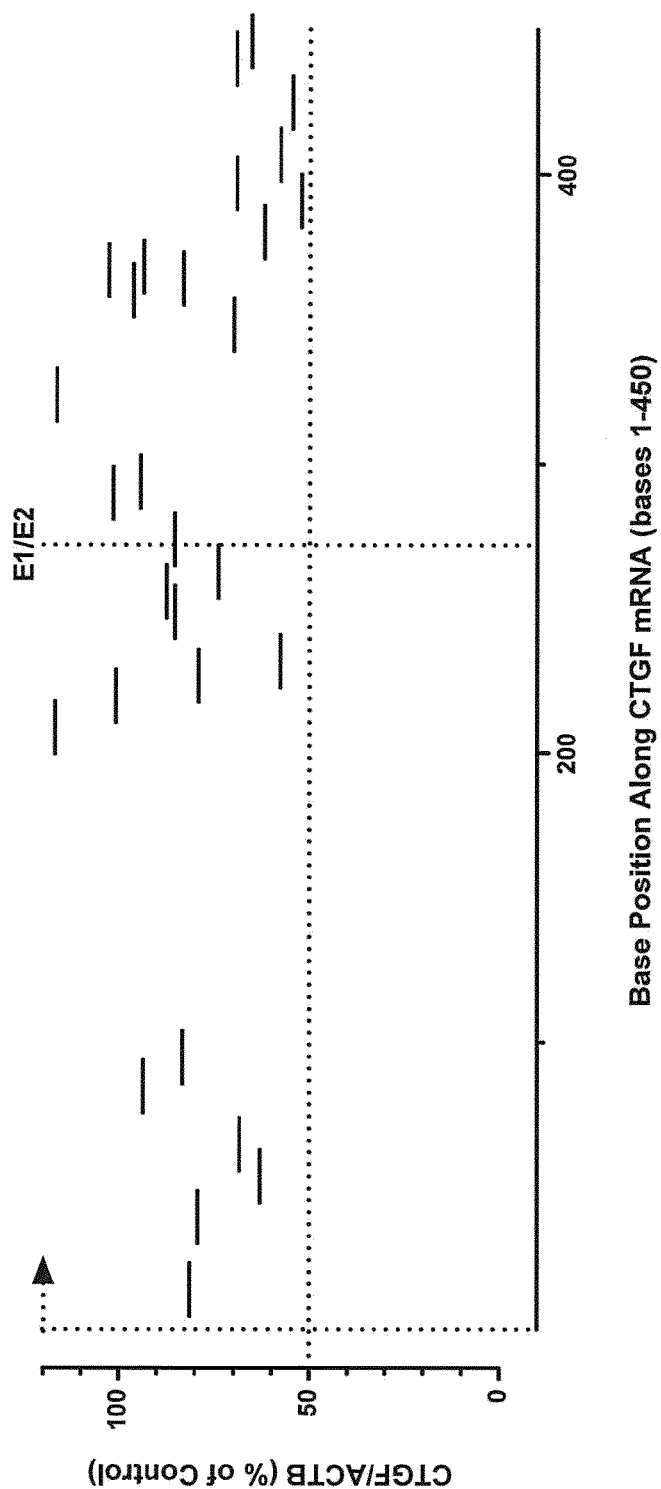
FIGS. 6A-6E illustrate the distribution of the nucleotide sequences that are complementary to Round 1-3 antisense oligonucleotides across the mature human CTGF mRNA sequence, SEQ ID NO 1. (National Center for Biotechnology Information (NCBI) Reference Sequence NM_001901) Additionally, these figures also show the degree of antisense mediated knockdown of mRNA expression produced by each antisense oligonucleotide. Thus the position of each symbol (line) along the x-axis corresponds to the complementary 20-nucleotide target site for each respective antisense oligonucleotide, while its position along the y-axis corresponds to the level of CTGF mRNA expression after transfection of that oligonucleotide as a percent of vehicle-treated control, with oligonucleotides located below the dashed 50% line producing greater than 50% mRNA knockdown.
Figure 6B:
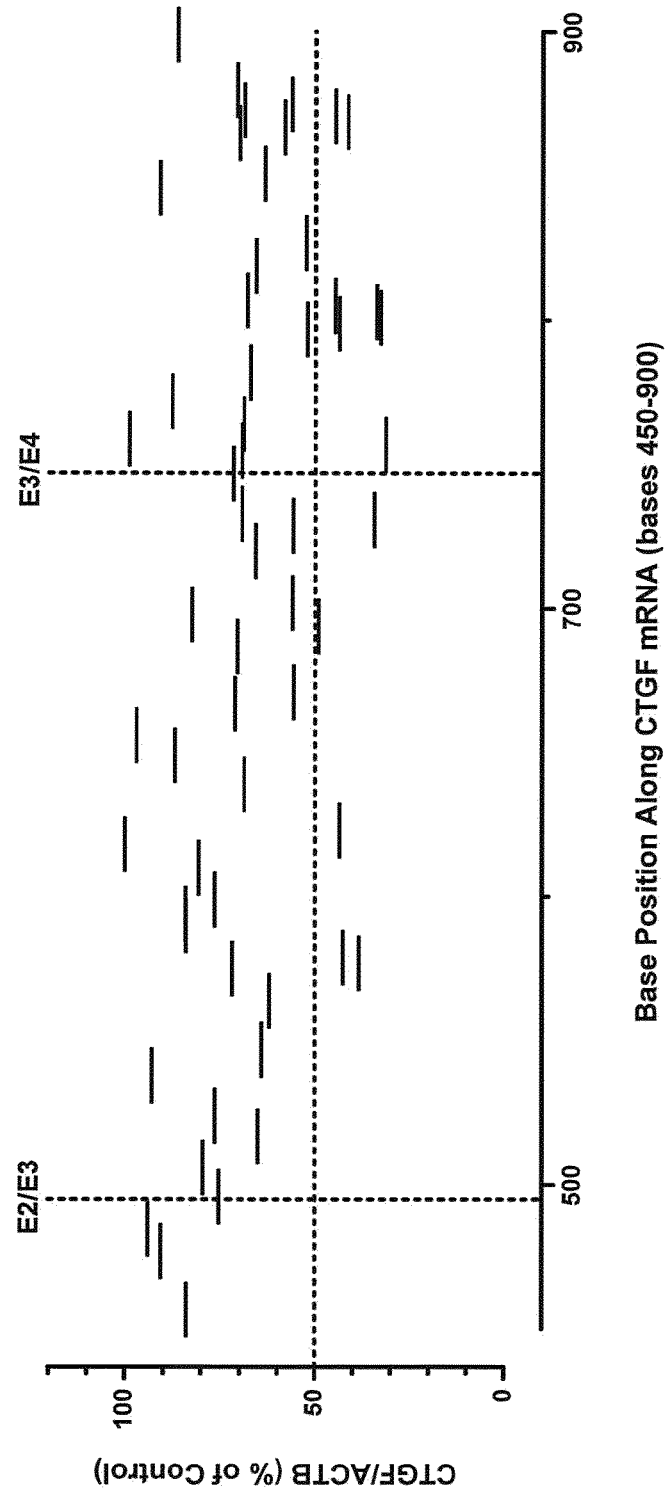
Figure 6C:
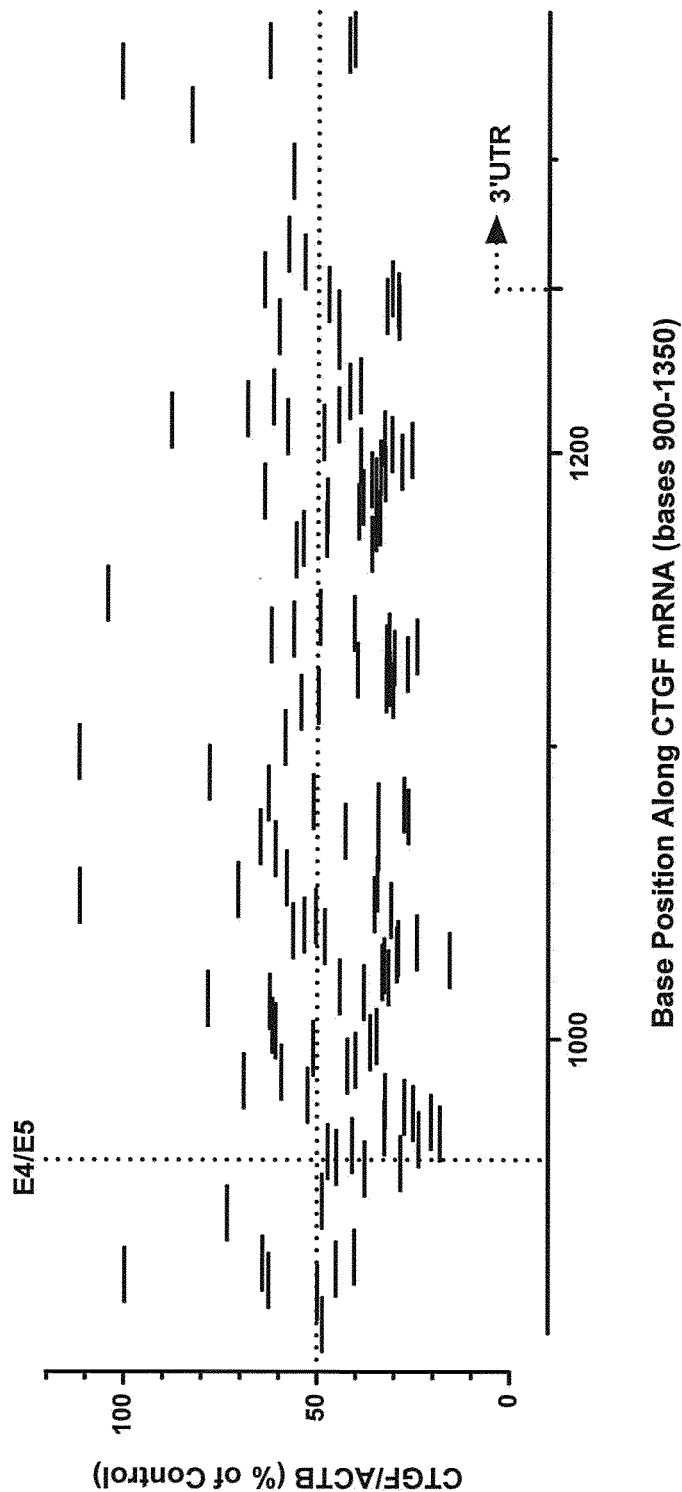
Figure 6D:
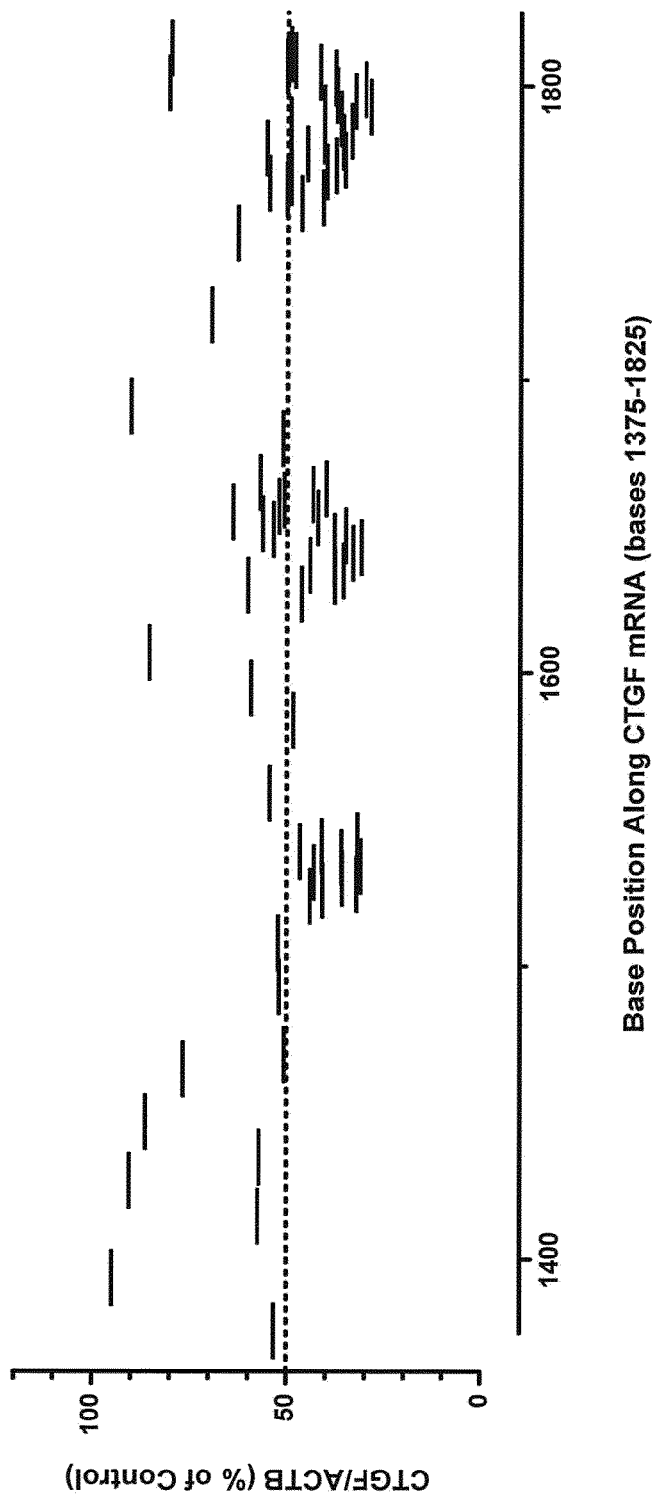
Figure 6E:
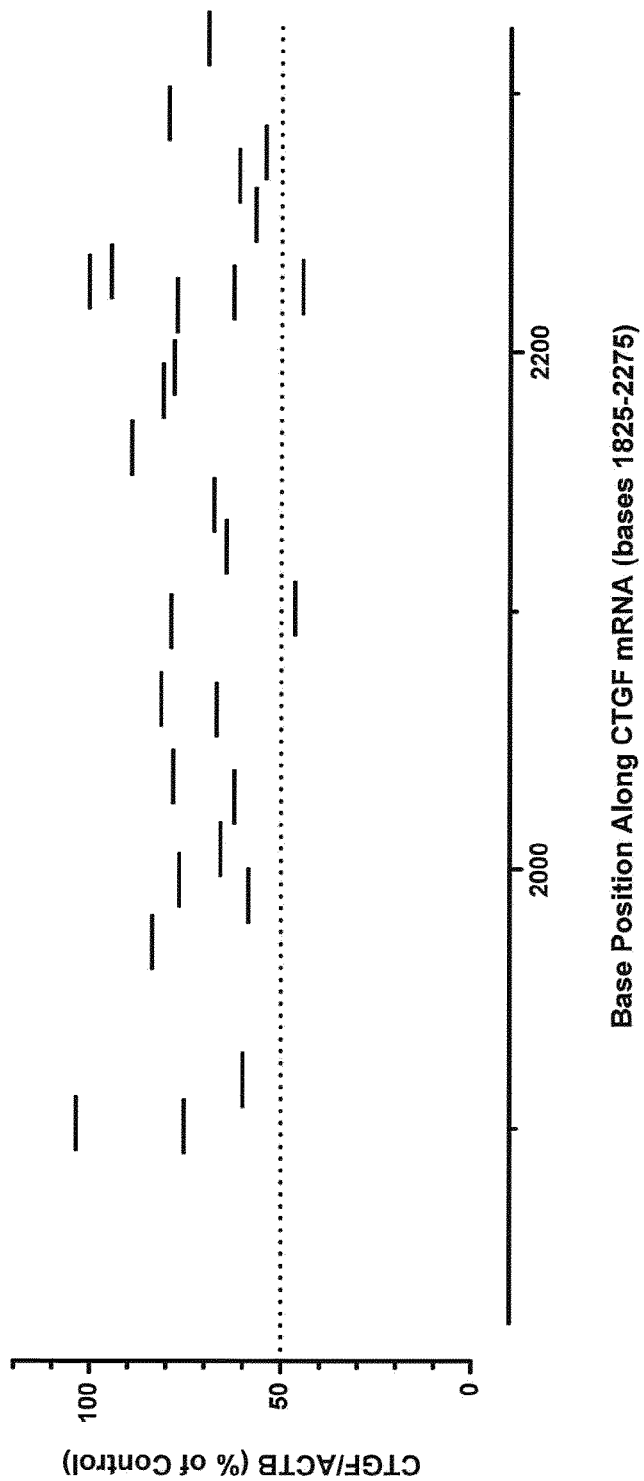

As was also seen in Round 2 studies, there was a shift in the distribution of inhibitory activity for Round 3 ASOs vs Round 1 ASOs, FIGS. 1 and 5, with a significantly higher proportion of Round 3 ASOs (65%) eliciting ≥50% CTGF mRNA knockdown than Round 1 ASOs (25%, p=1e-8). These data further demonstrate that potent ASOs are not randomly distributed along human CTGF mRNA, but instead are clustered in defined regions that are hypersensitive to ASO-mediated knockdown. This clustering of hypersensitive regions can be seen in FIGS. 6A-6E. The sequences and SEQ ID NOs of the identified hypersensitive regions of human CTGF mRNA are listed in Table 3.

Example 10

Hypersensitive Regions of CTGF mRNA

In total 316 unique 20-mer ASOs were tested to identify ASOs with high inhibitory activity and to define the discovered hypersensitive regions of human CTGF mRNA. These hypersensitive regions can be discerned from inspection of the Regional Status column of Table 2. In Table 3, the sequence of each hypersensitive region is further provided along with its respective SEQ ID NO and the overall percent inhibition of CTGF mRNA expression associated with the specific region.

TABLE 3

Hypersensitive Regions of human CTGF mRNA

| Nucleotide Range | Hypersensitive Sequence | SEQ ID NO. | % Inhibition |
|---|---|---|---|
| 567 to 588 | aagtaccagt gcacgtgcct gg | SEQ ID NO: 318 | ≥55% |
| 789 to 414 | attagagcca actgcctggt ccagac | SEQ ID NO: 319 | ≥55% |
| 859 to 880 | ccacccgggt taccaatgac aa | SEQ ID NO: 320 | ≥55% |
| 946 to 988 | aagagaacat taagaagggc aaaaagtgca tccgtactcc caa | SEQ ID NO: 321 | ≥50% |
| 981 to 1002 | actcccaaaa tctccaagcc ta | SEQ ID NO: 322 | ≥55% |
| 989 to 1010 | aatctccaag cctatcaagt tt | SEQ ID NO: 323 | ≥60% |
| 1006 to 1044 | agtttgagct ttctggctgc accagcatga agacatacc | SEQ ID NO: 324 | ≥50% |
| 1032 to 1055 | atgaagacat accgagctaa attc | SEQ ID NO: 325 | ≥50% |
| 1061 to 1089 | agtatgtacc gacggccgat gctgcaccc | SEQ ID NO: 326 | ≥55% |
| 1107 to 1145 | ctgccggtgg agttcaagtg ccctgacggc gaggtcatg | SEQ ID NO: 327 | ≥50% |
| 1132 to 1153 | acggcgaggt catgaagaag aa | SEQ ID NO: 328 | ≥50% |
| 1164 to 1194 | atcaagacct gtgcctgcca ttacaactgt c | SEQ ID NO: 329 | ≥50% |
| 1179 to 1216 | tgccattaca actgtcccgg agacaatgac atctttga | SEQ ID NO: 330 | ≥50% |
| 1211 to 1232 | ctttgaatcg ctgtactaca gg | SEQ ID NO: 331 | ≥55% |
| 1236 to 1265 | atgtacggag acatggcatg aagccagaga | SEQ ID NO: 332 | ≥50% |
| 1329 to 1350 | atgatttcag tagcacaagt ta | SEQ ID NO: 333 | ≥55% |
| 1514 to 1552 | tggctttagg agcagtggga gggtaccagc agaaaggtt | SEQ ID NO: 334 | ≥50% |
| 1623 to 1656 | tagcgtgctc actgacctgc ctgtagcccc agtg | SEQ ID NO: 335 | ≥55% |
| 1651 to 1672 | ccagtgacag ctaggatgtg ca | SEQ ID NO: 336 | ≥55% |
| 1750 to 1774 | aatgacactg ttcaggaatc ggaat | SEQ ID NO: 337 | ≥50% |
| 1759 to 1786 | gttcaggaat cggaatcctg tcgattag | SEQ ID NO: 338 | ≥50% |

TABLE 3-continued

Hypersensitive Regions of human CTGF mRNA

| Nucleotide Range | Hypersensitive Sequence | SEQ ID NO. | % Inhibition |
|---|---|---|---|
| 1771 to 1808 | gaatcctgtc gattagactg gacagcttgt ggcaagtg | SEQ ID NO: 339 | ≥50% |
| 1793 to 1820 | cagcttgtgg caagtgaatt tgcctgta | SEQ ID NO: 340 | ≥50% |

Table 3. Nucleotide ranges correspond to published human CTGF mRNA sequence (GenBank accession number NM_001901, SEQ ID NO: 1), wherein thymidine is substituted for uridine in the sequence. Sequences and nucleotide ranges are provided in the sense orientation.

The percent inhibition listed for each hypersensitivity region in Table 3 is the lowest value found in a particular hypersensitivity region. Most of the hypersensitive regions contain sub-regions that demonstrated higher sensitivity to antisense mediated inhibition. For example, the hypersensitive region from nucleotides 1006 to 1044, SEQ ID NO: 324, demonstrated at least 50% inhibition, but it has a sub-region from nucleotides 1017 to 1042 that demonstrated at least 70% inhibition.

Example 11

Additional Human Cell Lines Tested

The ability to broadly apply these findings across cell types and biological systems was demonstrated by retesting a subset of potent and non-potent antisense oligonucleotides in human MG63 osteosarcoma and A549 lung adenocarcinoma cell lines. Two independent transfection experiments were performed per cell line. The results demonstrated excellent correlations between the level of reduction of CTGF mRNA expression provided by the respective ASOs in Hs578T versus A549 ($r=0.93$), Hs578T versus MG63 ($r=0.88$), and MG63 versus A549 cells ($r=0.81$) ($p>1e-7$ each). These correlation studies showed that mRNA inhibition in Hs578T cells could be used to predict inhibitory activity in disparate cell types, indicating that hypersensitive regions are preserved across different CTGF expressing, cell types. These results demonstrate that different cell types share the identified hypersensitive regions of human CTGF mRNA and support the use of the antisense oligonucleotides of the invention for the treatment of all CTGF associated disorders and conditions.

Example 12

Similar Results in a Murine Cell Line

The CTGF mRNA hypersensitive regions identified by ASOs in human cell lines appear to be similar in CTGF mRNA from other mammals as well. This is demonstrated by the observation that ASOs that have identical human and murine target sequences (perfect complementarity) caused a median % KD in murine C2C12 cells that was significantly correlated median % KD seen in human Hs578T cells ($r=0.78$, $p<4e-10$).

Example 13

Inhibition of CTGF Protein Production

The ability of potent ASOs to alter the secretion of human CTGF protein is tested in Hs578T cells. As outlined in Example 3, cells are seeded into 96-well plates at 2000 cells/well in 100 µL of Hs578T growth medium. The cells are grown for 24 hrs in a humidified 37° C. incubator with 5% $CO_2$ after which the growth medium is removed and replaced with 80 µL of fresh growth medium. Designated wells then receive 20 µL of serum-free Opti-MEM® containing a potent or non-potent ASO and 0.5 µL of DharmaFECT® 4 transfection reagent as per the manufacturer's instructions. The final ASO concentration is 150 mM and each ASO is tested in three independent wells.

Cells are cultured for 17 hrs, after which 1 µL of DMEM containing 5 mg/mL heparin (Sigma-Aldrich Co., St. Louis, Mo.) is added to each well. The cells are then cultured for 1 hr, after which the growth medium is removed and the cells are washed once with 100 µL of PBS. After the PBS is removed, 100 µL of growth medium with 50 µg/mL heparin is added to each well. Cells are then cultured for 8 hrs, after which the culture medium is collected and frozen at −80° C. The cells are then re-fed with 100 µL of fresh growth medium containing 50 µg/mL heparin and cultured for an additional 16 hrs, after which the new growth medium is collected and stored at −80° C.

The amount of CTGF protein secreted by the cells during the intervals from 0 to 8 hrs and 8 to 24 hrs after the end of the 18 hr transfection period is measured by sandwich ELISA using monoclonal antibodies against epitopes of C- and N-terminal CTGF as capture and secondary antibody using recombinant CTGF as the standard (Dziadzio et al. *Q J Med* 98:485-, 2005). Treatment with the three potent ASOs result in lower levels of CTGF secretion at each time interval compared to the treatment with the three non-potent ASOs.

Example 14

Murine Cutaneous Wound-Healing Model

Mice are anesthetized with rodent cocktail (0.075 mg ketamine/0.015 mg xylazine/0.0025 mg aceprozamine per gram weight of mouse). The backs are shaved and disinfected. A full-thickness skin excision is made on the dorsal midline using an 8-mm dermal biopsy punch. The wounds are left open, but dressed.

Antisense Oligonucleotide Treatment

Mice are randomly divided into two groups (n=10 for each). On Day 0, one group is treated with 100 µg of antisense oligonucleotide, SEQ ID NO: 204, formulated in a slow release dressing. The other group receives a slow release dressing devoid of the antisense oligonucleotide as a control. Mice are monitored daily for general health and to check the integrity of the dressings. Mice are weighed twice weekly starting on Day −1.

On Day 15 post-biopsy, the animals are sacrificed. A sample of skin from the center of each wound is obtained with a 0.5 cm biopsy punch, and mRNA is extracted using standard procedures. RT-PCR mRNA analysis of mouse CTGF and Col1a2 is performed with mouse β-actin (Actb) used as the normalization gene.

Results

Treatment results in a statistically significant reduction in both CTGF and Col1a2 mRNA expression and demonstrates that inhibition of CTGF mRNA expression with an antisense oligonucleotide will decrease the deposition of collagen in skin, and hence, reduce the severity of scar formation. The change in weight of the treated mice group is not statistically different from the untreated group indicating the non-toxic nature of the treatment.

Example 15

Murine Surgical Adhesion Model

A hyaluronan hydrogel (Yeo et al. *Ann Surg*. 2007 May; 245(5):819-24) is used in the murine surgical model (Gorvy et al. *Am J Pathol*. 2005 October; 167(4):1005-19) to demonstrate the ability of an antisense oligonucleotide to inhibit the formation of surgical adhesions.

Animals

C57BL/6J adult male mice, age 10 to 12 weeks with a weight of 25 to 30 g, are used. Mice are maintained under standard conditions of food and water ad libitum on a 12-hour day-night cycle. Prior to surgery, mice are randomly divided into two groups, sham treated and treated (n=6 for each). Mice are then anesthetized with a mixture of inhaled isoflurane and oxygen, and a midline incision is made through the abdominal wall and peritoneum. A standard site (6 mm diameter and 1 mm depth), midway and ~0.5 cm lateral to the midline incision on the left abdominal wall, is injured using a trauma instrument (Dr. Mark Eastwood, Department of Biomedical Sciences, University of Westminster, London, UK).

The cecum is isolated and scraped 30 times on its lateral aspect with a scalpel blade, after first irrigating with 0.9% sterile saline. Hemorrhage is induced by lacerating a small blood vessel on the medial surface of the cecum with a hypodermic needle. The two injured surfaces are then apposed by placing two horizontal mattress sutures (8/0 Ethilon; Ethicon, Berkshire, UK) 1.2 cm apart.

Antisense Oligonucleotide Treatment

Sham treated mice receive 2 ml of cross-linked hydrogel placed between the two injured surfaces, while antisense oligonucleotide treated mice receive 2 ml of cross-linked hydrogel containing 100 μg (50 μg/ml) of the antisense oligonucleotide represented by SEQ ID NO: 204. The midline incision is closed in two layers; the linea-alba with a continuous suture, and then the skin using interrupted sutures (6/0 Ethilon, Ethicon, Somerville, N.J.).

At 7 days after surgery, mice are sacrificed and adhesions are assessed macroscopically according to the number of adhesions and sites of adhesion formation. Additionally, the mice are photographed for independent examination. A category 1 adhesion is defined as an adhesion between the two abraded serosal surfaces, i.e., cecum to abraded body wall. Category 2 adhesions involve the two abraded surfaces and an uninvolved site, such as the greater omentum and abraded body wall. Category 3 adhesions describe adhesions that form at a distant site to the abraded serosa, for example the fat body to the midline incision.

Results

All animals in the sham treated group form adhesions at the trauma site (category 1) and with some adhesions noted between abraded surfaces and an uninvolved site (category 2) and at distant sites (category 3) are observed in 2 animals. In contrast, animals treated with the antisense oligonucleotide containing hydrogel show significant in trauma site adhesions and adhesions between abraded surfaces and uninvolved sites with no distant site adhesions present.

What is claimed:

1. A modified antisense oligonucleotide, 12 to 20 nucleotides in length, that is complementary to a region of human connective tissue growth factor (CTGF) mRNA and comprises at least 12 consecutive nucleotides of an oligonucleotide selected from the group consisting of SEQ ID NO: 273, SEQ ID NO: 274, SEQ ID NO: 275, SEQ ID NO: 232, SEQ ID NO: 106, SEQ ID NO: 233 and SEQ ID NO: 276.

2. A modified antisense oligonucleotide between 12 and 30 nucleotides in length that is complementary to a region within nucleotides 1185 to 1216 of SEQ ID NO:1.

3. The oligonucleotide of claim 1 or 2, wherein the modification of the oligonucleotide comprises the incorporation of at least one non-naturally occurring internucleoside linkage, sugar moiety, or nucleobase.

4. The oligonucleotide of claim 3, wherein the at least one non-naturally occurring internucleoside linkage is a phosphothioate internucleoside linkage.

5. The oligonucleotide of claim 4, wherein all of the internucleoside linkages are phosphothioate internucleoside linkages.

6. The oligonucleotide of claim 3, wherein the at least one non-naturally occurring sugar moiety is a bicyclic sugar.

7. The oligonucleotide of claim 3, wherein the at least one non-naturally occurring sugar comprises a 2'-O,4'-C-methylene bridge.

8. The oligonucleotide of claim 3, wherein the at least one non-naturally occurring nucleobase is a 5-methylcytosine.

9. The modified antisense oligonucleotide of claim 1 that is complementary to a region of human connective tissue growth factor (CTGF) mRNA and comprises SEQ ID NO:274.

10. A modified antisense oligonucleotide selected from the group consisting of SEQ ID NO: 105, SEQ ID NO: 230, SEQ ID NO 231, SEQ ID NO: 273, SEQ ID NO: 274, SEQ ID NO: 275, SEQ ID NO: 232, SEQ ID NO: 106, SEQ ID NO: 233 and SEQ ID NO: 276.

11. The modified antisense oligonucleotide of claim 2, wherein the modified antisense oligonucleotide is between 12 and 20 nucleotides in length.

12. A method of treating a CTGF-associated disorder comprising, administering to a subject in need thereof, an effective amount of a modified antisense oligonucleotide, 12 to 30 nucleotides in length, that is complementary to a region within nucleotides 1185 to 1216 of SEQ ID NO: 1, thereby treating the CTGF-associated disorder.

13. The method of claim 12, wherein the CTGF-associated disorder is selected from the group consisting of dermal fibrosis, liver fibrosis, pulmonary fibrosis, renal fibrosis, cardiac fibrosis, ocular fibrosis, scleroderma, surgical scars and adhesions, scars from wounds, scars from burns, restenosis, glomerular sclerosis, osteoarthritis and cancer.

14. The method of claim 13, wherein the cancer is selected from the group consisting of acute lymphoblastic leukemia, dermatofibromas, breast cancer, breast carcinoma desmoplasia, angiolipoma, angioleiomyoma, desmoplastic cancer, prostate cancer, ovarian cancer, colorectal cancer, pancreatic cancer, gastrointestinal cancer, and liver cancer.

\* \* \* \* \*